(12) United States Patent
Bhai

(10) Patent No.: US 7,437,787 B2
(45) Date of Patent: Oct. 21, 2008

(54) LOAD-CELL BASED HOSPITAL BED CONTROL

(75) Inventor: Aziz Ali Bhai, Batesville, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 11/833,311

(22) Filed: Aug. 3, 2007

(65) Prior Publication Data

US 2007/0268147 A1    Nov. 22, 2007

Related U.S. Application Data

(63) Continuation of application No. 11/009,872, filed on Dec. 10, 2004, now Pat. No. 7,253,366.

(60) Provisional application No. 60/615,031, filed on Oct. 1, 2004, provisional application No. 60/599,558, filed on Aug. 9, 2004.

(51) Int. Cl.
    *A61G 7/002* (2006.01)
    *A61G 7/018* (2006.01)
    *A61G 7/05* (2006.01)
    *G01G 19/52* (2006.01)

(52) U.S. Cl. .................. 5/613; 5/615; 5/689; 177/144; 340/666

(58) Field of Classification Search ............ 5/613, 5/615, 689; 177/144, 245; 340/666
See application file for complete search history.

(56) References Cited

U.S. PATENT DOCUMENTS

| | | | |
|---|---|---|---|
| 299,649 A | 6/1884 | Keep et al. | |
| 1,758,546 A | 5/1930 | Wartmann | |
| 1,969,554 A | 8/1934 | Gloudemans | |
| 2,249,645 A | 7/1941 | Applegarth, Sr. | |
| 2,260,715 A | 10/1941 | Ketchen | |
| 2,425,790 A | 8/1947 | Fletcher | |
| 2,430,702 A | 11/1947 | Bohannan | |
| 2,644,332 A | 7/1953 | Ulrich | |
| 2,735,291 A | 2/1956 | Quinn | |
| 2,780,693 A | 2/1957 | McClellan | |
| 2,784,395 A | 3/1957 | Gorby | |
| 2,818,477 A | 12/1957 | Golhofer | |
| 2,819,612 A | 1/1958 | Borgstrom et al. | |
| 2,990,899 A | 7/1961 | DeBella | |
| 3,096,061 A | 7/1963 | Bertell | |
| 3,217,818 A | 11/1965 | Engelsher et al. | |
| 3,325,799 A | 6/1967 | Farris | |

(Continued)

*Primary Examiner*—Randy W Gibson
(74) *Attorney, Agent, or Firm*—Barnes & Thornburg LLP

(57) ABSTRACT

A system for monitoring a patient on a hospital bed includes load cells and a controller for detecting patient movement on, exit from, and impending exit from the hospital bed, including movement across or outside a virtual boundary or region located on the bed. The controller is configured to detect changes in the distribution of patient weight among the load cells. The controller is also configured to accommodate the installation or removal of medical equipment or other tare weights on the bed, head incline adjustment, and bed frame deformation or other changes in the system causing redistribution of weight among the load cells, while minimizing false alarms. A caregiver may select between various patient monitoring modes and remotely monitor patient movement relative to a reference load cell distribution, impending patient exit from the bed and patient exit from the bed. Pressures in an air mattress may be controlled based on signals from the load cells.

17 Claims, 25 Drawing Sheets

U.S. PATENT DOCUMENTS

| | | |
|---|---|---|
| 3,338,323 A | 8/1967 | Swersey |
| 3,360,062 A | 12/1967 | Potter |
| 3,418,847 A | 12/1968 | Nantz |
| 3,439,358 A | 4/1969 | Salmons |
| 3,492,865 A | 2/1970 | Johnson |
| 3,504,540 A | 4/1970 | Pradko et al. |
| 3,512,595 A | 5/1970 | Laimins |
| 3,533,095 A | 10/1970 | Collins |
| 3,589,457 A | 6/1971 | Joos |
| 3,656,478 A | 4/1972 | Swersey |
| 3,657,475 A | 4/1972 | Peronneau et al. |
| 3,712,294 A | 1/1973 | Muller |
| 3,722,611 A | 3/1973 | Tirkkonen |
| 3,741,328 A | 6/1973 | Anderson et al. |
| 3,760,794 A | 9/1973 | Bashan |
| 3,766,344 A | 10/1973 | Nevett |
| 3,773,124 A | 11/1973 | Bullivant |
| 3,781,843 A | 12/1973 | Harrison et al. |
| 3,795,284 A | 3/1974 | Mracek et al. |
| 3,796,208 A | 3/1974 | Bloice |
| 3,826,145 A | 7/1974 | McFarland |
| 3,836,900 A | 9/1974 | Mansfield |
| 3,852,736 A | 12/1974 | Cook et al. |
| 3,876,018 A | 4/1975 | Mracek et al. |
| 3,890,958 A | 6/1975 | Fister et al. |
| RE28,754 E | 3/1976 | Cook et al. |
| 3,961,201 A | 6/1976 | Rosenthal |
| 3,961,675 A | 6/1976 | Siegel |
| 3,972,320 A | 8/1976 | Kalman |
| 3,974,491 A | 8/1976 | Sipe |
| 3,988,790 A | 11/1976 | Mracek et al. |
| 3,991,414 A | 11/1976 | Moran |
| 3,991,746 A | 11/1976 | Hanna |
| 4,006,789 A | 2/1977 | Stulz et al. |
| 4,015,677 A | 4/1977 | Silva et al. |
| 4,020,482 A | 4/1977 | Feldl |
| 4,023,633 A | 5/1977 | Swersey et al. |
| 4,066,506 A | 1/1978 | Levy et al. |
| 4,067,005 A | 1/1978 | Levy et al. |
| 4,121,049 A | 10/1978 | Roeber |
| 4,129,189 A | 12/1978 | Maglecic et al. |
| 4,140,998 A | 2/1979 | Bettle |
| 4,175,263 A | 11/1979 | Triplett et al. |
| 4,179,692 A | 12/1979 | Vance |
| 4,195,287 A | 3/1980 | McCoy et al. |
| 4,228,426 A | 10/1980 | Roberts |
| 4,231,030 A | 10/1980 | Weiss |
| 4,242,672 A | 12/1980 | Gault |
| 4,245,651 A | 1/1981 | Frost |
| 4,263,586 A | 4/1981 | Nicholas |
| 4,264,904 A | 4/1981 | McCoy et al. |
| 4,281,730 A | 8/1981 | Swersey et al. |
| 4,282,412 A | 8/1981 | Florin |
| 4,295,133 A | 10/1981 | Vance |
| 4,298,863 A | 11/1981 | Naitus et al. |
| 4,320,766 A | 3/1982 | Alihanka et al. |
| 4,336,533 A | 6/1982 | Wettach |
| 4,337,726 A | 7/1982 | Czekajewski et al. |
| 4,346,771 A | 8/1982 | Persson et al. |
| 4,348,562 A | 9/1982 | Florin |
| 4,363,368 A | 12/1982 | Paddon et al. |
| 4,411,327 A | 10/1983 | Lockery et al. |
| 4,420,052 A | 12/1983 | Hale |
| 4,426,884 A | 1/1984 | Polchaninoff |
| 4,438,823 A | 3/1984 | Hussels et al. |
| 4,474,185 A | 10/1984 | Diamond |
| 4,482,783 A | 11/1984 | Laimins |
| 4,484,043 A | 11/1984 | Musick et al. |
| 4,487,276 A | 12/1984 | Swersey et al. |
| 4,492,281 A | 1/1985 | Van Allen et al. |
| 4,526,043 A | 7/1985 | Boie et al. |
| 4,536,755 A | 8/1985 | Holzgang et al. |
| 4,539,560 A | 9/1985 | Fleck et al. |
| 4,540,057 A | 9/1985 | Freeman |
| 4,550,793 A | 11/1985 | Giles |
| 4,551,882 A | 11/1985 | Swersey et al. |
| 4,558,757 A | 12/1985 | Mori et al. |
| 4,565,910 A | 1/1986 | Musick et al. |
| 4,573,475 A | 3/1986 | Dukes et al. |
| 4,577,185 A | 3/1986 | Andersen |
| 4,583,084 A | 4/1986 | Henderson et al. |
| 4,584,989 A | 4/1986 | Stith |
| 4,601,356 A | 7/1986 | Muccillo, Jr. |
| 4,629,015 A | 12/1986 | Fried et al. |
| 4,633,237 A | 12/1986 | Tucknott et al. |
| 4,638,307 A | 1/1987 | Swartout |
| 4,649,759 A | 3/1987 | Lee |
| 4,700,180 A | 10/1987 | Vance |
| 4,751,754 A | 6/1988 | Bailey et al. |
| 4,777,944 A | 10/1988 | Green et al. |
| 4,793,428 A | 12/1988 | Swersey |
| 4,796,013 A | 1/1989 | Yasuda et al. |
| 4,803,744 A | 2/1989 | Peck et al. |
| 4,804,052 A | 2/1989 | Griffen |
| 4,805,637 A | 2/1989 | Walthert |
| 4,827,763 A | 5/1989 | Bourland et al. |
| 4,839,512 A | 6/1989 | Speck |
| 4,845,323 A | 7/1989 | Beggs |
| 4,858,622 A | 8/1989 | Osterweil |
| 4,899,840 A | 2/1990 | Boubille |
| 4,907,845 A | 3/1990 | Wood |
| 4,909,338 A | 3/1990 | Vitunic et al. |
| 4,926,951 A | 5/1990 | Carruth et al. |
| 4,934,468 A | 6/1990 | Koerber, Sr. et al. |
| 4,947,152 A | 8/1990 | Hodges |
| 4,947,298 A | 8/1990 | Stephen |
| 4,951,032 A | 8/1990 | Langsam |
| 4,953,244 A | 9/1990 | Koerber, Sr. et al. |
| 4,953,410 A | 9/1990 | Tabota |
| 4,955,947 A | 9/1990 | Hajianpour |
| 4,961,470 A | 10/1990 | Koerber, Sr. |
| 4,967,384 A | 10/1990 | Molinar et al. |
| 4,972,177 A | 11/1990 | Nolan |
| 4,974,692 A | 12/1990 | Carruth et al. |
| 5,003,654 A * | 4/1991 | Vrzalik .................. 5/715 |
| 5,008,654 A | 4/1991 | Callaway |
| 5,010,772 A | 4/1991 | Bourland et al. |
| 5,010,774 A | 4/1991 | Kikao et al. |
| 5,033,563 A | 7/1991 | Brainerd, Jr. et al. |
| 5,044,029 A * | 9/1991 | Vrzalik .................. 5/713 |
| 5,060,174 A | 10/1991 | Gross |
| 5,140,309 A | 8/1992 | Gusakov |
| 5,144,284 A | 9/1992 | Hammett |
| 5,166,679 A | 11/1992 | Vranish et al. |
| 5,170,364 A | 12/1992 | Gross et al. |
| 5,173,977 A | 12/1992 | Carruth et al. |
| 5,183,126 A | 2/1993 | Kellenbach |
| 5,184,112 A | 2/1993 | Gusakov |
| 5,209,126 A | 5/1993 | Grahn |
| 5,232,064 A | 8/1993 | Kroll et al. |
| 5,235,319 A | 8/1993 | Hill et al. |
| 5,253,656 A | 10/1993 | Rincoe et al. |
| 5,268,670 A | 12/1993 | Brasch et al. |
| 5,269,388 A | 12/1993 | Reichow et al. |
| 5,276,432 A | 1/1994 | Travis |
| 5,279,010 A | 1/1994 | Ferrand et al. |
| 5,319,817 A | 6/1994 | Hay et al. |
| 5,353,012 A | 10/1994 | Barham et al. |
| 5,393,935 A | 2/1995 | Hasty et al. |
| 5,393,938 A | 2/1995 | Bumbalough |
| 5,410,297 A | 4/1995 | Joseph et al. |
| D361,462 S | 8/1995 | Newham |
| 5,446,391 A | 8/1995 | Aoki et al. |
| 5,448,996 A | 9/1995 | Bellin et al. |

| | | | | | | |
|---|---|---|---|---|---|---|
| 5,459,452 A | 10/1995 | DePonte | | 6,078,261 A | 6/2000 | Davsko |
| 5,471,198 A | 11/1995 | Newham | | 6,094,762 A | 8/2000 | Viard et al. |
| 5,479,939 A | 1/1996 | Ogino | | 6,111,509 A | 8/2000 | Holmes |
| 5,487,196 A * | 1/1996 | Wilkinson et al. ............. 5/715 | | 6,115,860 A * | 9/2000 | Vrzalik ........................ 5/715 |
| 5,494,046 A | 2/1996 | Cross | | 6,133,837 A | 10/2000 | Riley |
| 5,519,380 A | 5/1996 | Edwards | | 6,147,592 A | 11/2000 | Ulrich et al. |
| RE35,301 E | 7/1996 | Reichow | | 6,166,644 A | 12/2000 | Stroda |
| 5,554,835 A | 9/1996 | Newham | | D436,322 S | 1/2001 | Wajer |
| 5,571,973 A | 11/1996 | Taylot | | 6,180,893 B1 | 1/2001 | Salgo |
| 5,600,108 A | 2/1997 | Newham | | 6,204,767 B1 | 3/2001 | Sparks |
| 5,602,734 A | 2/1997 | Kithil | | 6,208,249 B1 | 3/2001 | Saito et al. |
| 5,623,760 A | 4/1997 | Newham | | 6,208,250 B1 | 3/2001 | Dixon et al. |
| 5,633,627 A | 5/1997 | Newham | | 6,239,706 B1 | 5/2001 | Yoshiike et al. |
| 5,640,145 A | 6/1997 | Newham | | 6,252,512 B1 | 6/2001 | Riley |
| 5,654,694 A | 8/1997 | Newham | | 6,297,738 B1 | 10/2001 | Newham |
| 5,664,270 A | 9/1997 | Bell et al. | | 6,307,476 B1 | 10/2001 | Smith et al. |
| 5,672,849 A | 9/1997 | Foster et al. | | 6,320,510 B2 | 11/2001 | Menkedick et al. |
| 5,699,038 A | 12/1997 | Ulrich et al. | | RE37,467 E | 12/2001 | Brasch et al. |
| 5,715,548 A | 2/1998 | Weismiller et al. | | 6,362,439 B1 | 3/2002 | Reichow |
| 5,717,167 A | 2/1998 | Filing et al. | | 6,362,725 B1 | 3/2002 | Ulrich et al. |
| 5,747,745 A | 5/1998 | Newman | | 6,417,777 B2 | 7/2002 | Fitzgerald et al. |
| 5,760,688 A | 6/1998 | Kasai | | 6,438,776 B2 | 8/2002 | Ferrand et al. |
| 5,767,774 A | 6/1998 | Wright et al. | | 6,441,742 B1 | 8/2002 | Lovely et al. |
| 5,780,781 A | 7/1998 | Berger et al. | | 6,502,048 B1 | 12/2002 | Lichtinger et al. |
| 5,780,798 A | 7/1998 | Hall-Jackson | | 6,544,200 B1 | 4/2003 | Smith et al. |
| 5,796,059 A | 8/1998 | Boon | | 6,583,727 B2 | 6/2003 | Nunome |
| 5,801,339 A | 9/1998 | Boult | | 6,636,820 B2 | 10/2003 | Livingston |
| 5,802,479 A | 9/1998 | Kithil et al. | | 6,646,556 B1 | 11/2003 | Smith et al. |
| 5,802,640 A | 9/1998 | Ferrand et al. | | 6,727,445 B2 | 4/2004 | Cullinan et al. |
| 5,808,552 A | 9/1998 | Wiley et al. | | 6,784,379 B2 * | 8/2004 | Breed et al. ................... 177/144 |
| 5,810,392 A | 9/1998 | Gagon | | 6,784,797 B2 | 8/2004 | Smith et al. |
| 5,815,864 A * | 10/1998 | Sloop ............................ 5/706 | | 6,791,460 B2 | 9/2004 | Dixon et al. |
| 5,823,278 A | 10/1998 | Geringer | | 6,792,342 B2 * | 9/2004 | Breed et al. ................... 701/45 |
| 5,831,221 A | 11/1998 | Geringer et al. | | 6,819,254 B2 | 11/2004 | Riley |
| 5,844,488 A | 12/1998 | Musick | | 6,822,571 B2 | 11/2004 | Conway |
| 5,846,206 A | 12/1998 | Bader | | 7,100,439 B2 | 9/2006 | Carlucci |
| 5,859,390 A | 1/1999 | Stafford et al. | | 7,126,065 B2 | 10/2006 | Petrucelli |
| 5,861,581 A | 1/1999 | Evans et al. | | 7,253,366 B2 | 8/2007 | Bhai |
| 5,861,582 A | 1/1999 | Flanagan et al. | | 2001/0001235 A1 | 5/2001 | Menedick et al. |
| 5,869,788 A | 2/1999 | Gordon et al. | | 2001/0001237 A1 | 5/2001 | Stroda et al. |
| 5,879,309 A | 3/1999 | Johnson et al. | | 2001/0015292 A1 | 8/2001 | Salgo |
| 5,906,016 A | 5/1999 | Ferrand et al. | | 2002/0067273 A1 | 6/2002 | Jaues et al. |
| 5,933,083 A | 8/1999 | Sobczynski et al. | | 2002/0070867 A1 | 6/2002 | Conway et al. |
| 5,941,836 A | 8/1999 | Friedman | | 2002/0080037 A1 | 6/2002 | Dixon et al. |
| 5,945,914 A | 8/1999 | Holmes et al. | | 2002/0189924 A1 | 12/2002 | Cullinan et al. |
| 5,957,838 A | 9/1999 | Rantala | | 2002/0196148 A1 | 12/2002 | Nunome |
| 5,990,799 A | 11/1999 | Boon et al. | | 2003/0063010 A1 | 4/2003 | Smith et al. |
| 5,999,100 A | 12/1999 | Wright et al. | | 2003/0073936 A1 | 4/2003 | Raisanen |
| 6,025,782 A | 2/2000 | Newham | | 2003/0090383 A1 | 5/2003 | Conway |
| 6,036,660 A | 3/2000 | Toms | | 2003/0114736 A1 | 6/2003 | Reed et al. |
| D424,650 S | 5/2000 | Reichow | | 2003/0197614 A1 | 10/2003 | Smith et al. |
| 6,067,019 A | 5/2000 | Scott | | 2004/0046668 A1 | 3/2004 | Smith et al. |
| 6,075,464 A | 6/2000 | Cloutier et al. | | 2006/0028350 A1 | 2/2006 | Bhai |
| 6,078,253 A | 6/2000 | Fowler | | | | |

* cited by examiner

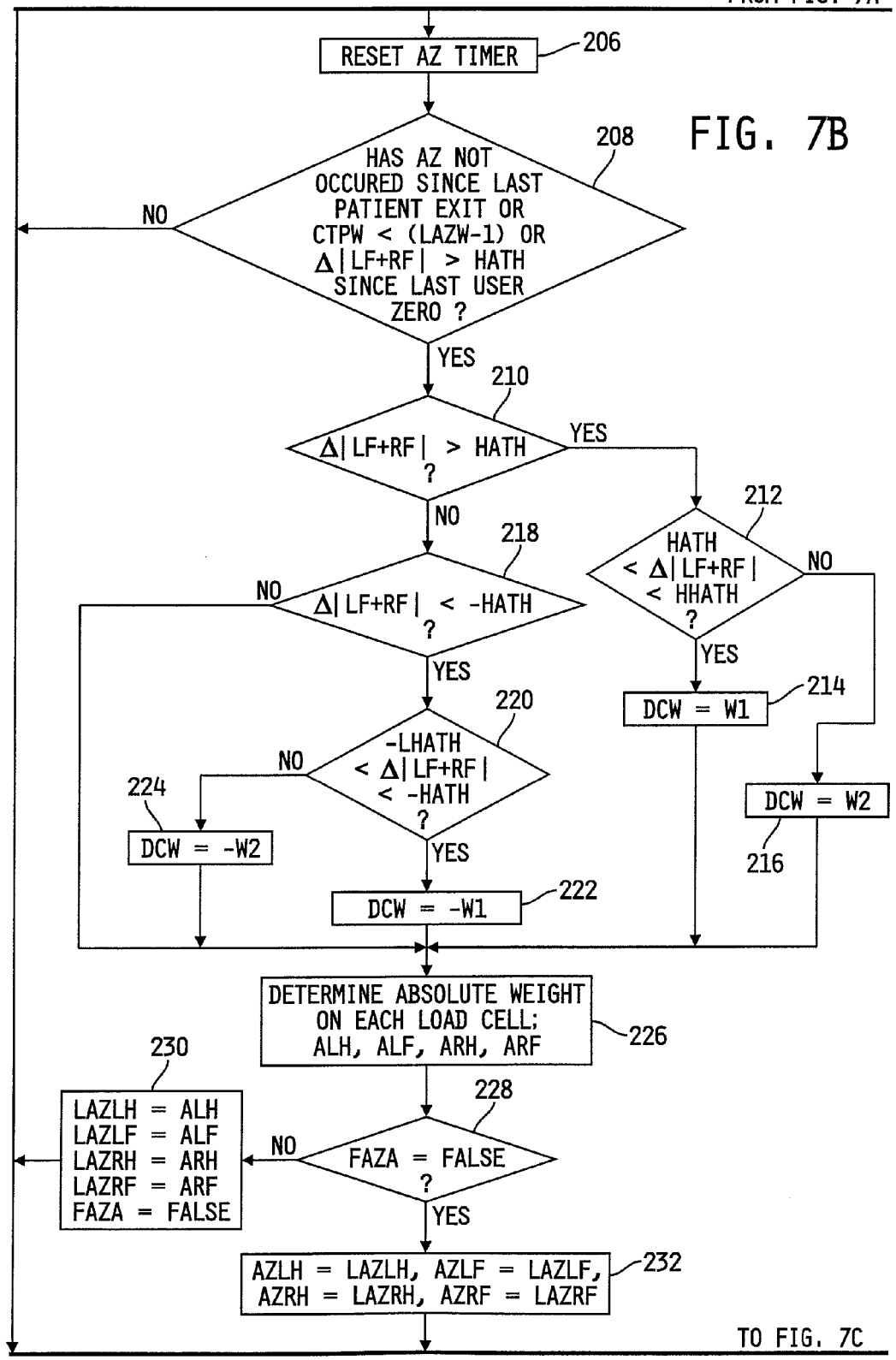

LOAD-CELL BASED HOSPITAL BED CONTROL

CROSS-REFERENCE TO RELATED U.S. PATENT APPLICATIONS

This patent application is a continuation of U.S. application Ser. No. 11/009,872, which was filed Dec. 10, 2004 and issued as U.S. Pat. No. 7,253,366 on Aug. 7, 2007 and which claimed priority to and the benefit of U.S. Provisional Patent Application Ser. No. 60/599,558, filed Aug. 9, 2004, and U.S. Provisional Patent Application Ser. No. 60/615,031, filed Oct. 1, 2004, the disclosures of which are each incorporated herein by reference.

FIELD OF THE INVENTION

This invention relates generally to systems for monitoring and detecting movement of a mass on a platform, and more specifically to methods and systems for detecting patient movement on, exit from, or impending exit from a patient support system such as a hospital bed.

BACKGROUND

When a patient is required to stay in a hospital bed at a hospital or other patient care facility, it is desirable for a caregiver to be able to monitor the presence, absence, and movement of the patient on the bed platform, generally a mattress, and to monitor the patient's activity level. Caregivers are generally responsible for a number of patient-related activities, examples of which include monitoring the presence or absence of patients on their hospital beds and/or monitoring patient movement relative to their hospital beds.

One system for monitoring patient movement on a hospital bed is disclosed by U.S. Pat. No. 5,276,432, issued Jan. 4, 1994, to Travis. The disclosed system calculates the center of gravity of a patient within a two-dimensional Cartesian coordinate-based region defined relative to the patient-supporting surface of the bed mattress. The center of gravity of the patient relative to the region is determined using data from load cells coupled to the hospital bed frame. Patient movement relative to the region is detected by monitoring movement of the center of gravity of the patient, and by determining the location of the patient's center of gravity relative to the region.

Alternative methods and systems for monitoring patient movement on, exit from and/or impending exit from, a hospital bed are desirable.

SUMMARY

The present invention may comprise one or more of the features recited in the appended claims and/or one or more of the following features or combinations thereof. A system for monitoring a patient on a patient support, such as a hospital bed or stretcher having a support surface, may comprise a plurality of load cells positioned to weigh the support surface and the patient supported thereon. In one exemplary embodiment, four such load cells may be mounted at or near each of the four corners of the support, one at each right and left side at or near the head of the support and one at each right and left side at or near the foot of the support. Output signals of the load cells, which may typically be voltage or current level outputs, may be digitized for processing by a control system computer.

Various algorithms may utilize various combinations of the load cell output signals to determine the weight of the patient on the support surface, exit of the patient from the support surface, impending exit of the patient from the support surface and/or movement of the patient relative to reference load cell distribution values.

One such algorithm, for example, may be configured to determine when the patient is in process of exiting the support surface. When, for example, the sum of output signals of all four cells is substantially less than, e.g., by 30 pounds to 60 pounds, the established weight of the patient, this may be indicative that the patient has transferred at least some of the patient's total weight off the support surface onto some other support surface or structure that supports the missing weight.

Another algorithm, for example, may determine when a patient's movement on the support surface exceeds any of a number of predetermined load cell thresholds. A collection of weight distribution threshold percentages for each of the four cells RH, LH, RF and LF is stored in memory and continually compared against the current load cell values after arming of the system. When the distribution of weight among two or three of the four cells changes by more than one of the corresponding stored collection of weight distribution threshold percentages as a result of excessive patient movement subsequent to the system being armed, an alarm is triggered.

Yet another algorithm, for example, will determine when a patient is about to exit the support surface. A collection of load cells thresholds for each of the four cells RH, LH, RF and LF is stored in memory, and the current load cell values are compared to selected portions of the load cell threshold collection. When the measured distribution of weight among the four cells RH, LH, RF and LF exceeds a set of load cell thresholds forming the collection of load cell thresholds as a result of impending patient exit from the support surface, an alarm is triggered.

The above briefly described algorithms of the system do not determine the center of gravity of a patient. Nor do the algorithms determine the actual position of a patient relative to a reference position. Nor do the algorithms require a measured length or width of the support surface. Nor do the algorithms determine or use any information relating to the physical locations of the various load cells relative to a reference position, or any information relating to distances between such load cells. The actual locations of the various load cells are arbitrary, and the locations of the load cells shown in the illustrated embodiments are provided only by way of example. The locations of the load cells may therefore be different for different applications.

The briefly described algorithms monitor the distribution of patient weight supported by each of the four cells RH, LH, RF and LF, and compare the resulting load cell weights to empirically determined and/or model-based collections of load cell threshold data. Changes in patient weight distribution among two, three or four of the load cells relative to the one or more collections of load cell threshold data are then used in a decision process to detect excessive patient movement and/or impending exit from, and/or exit from, the support surface. The algorithms accomplish this without reference to a patient center of gravity, an actual patient position relative to a reference position or a coordinate axis, actual locations of one or more of the load cells relative to a reference position or distance between any such load cells.

These and other features of the present invention will become more apparent from the following description of the illustrated embodiments.

BRIEF DESCRIPTION OF THE DRAWINGS

FIGS. 7A-7C show a flowchart illustrating an exemplary embodiment of a software routine for executing the PM Off State that forms part of the state machine of FIG. 5.

DESCRIPTION OF THE ILLUSTRATIVE EMBODIMENTS

Figure 1A:
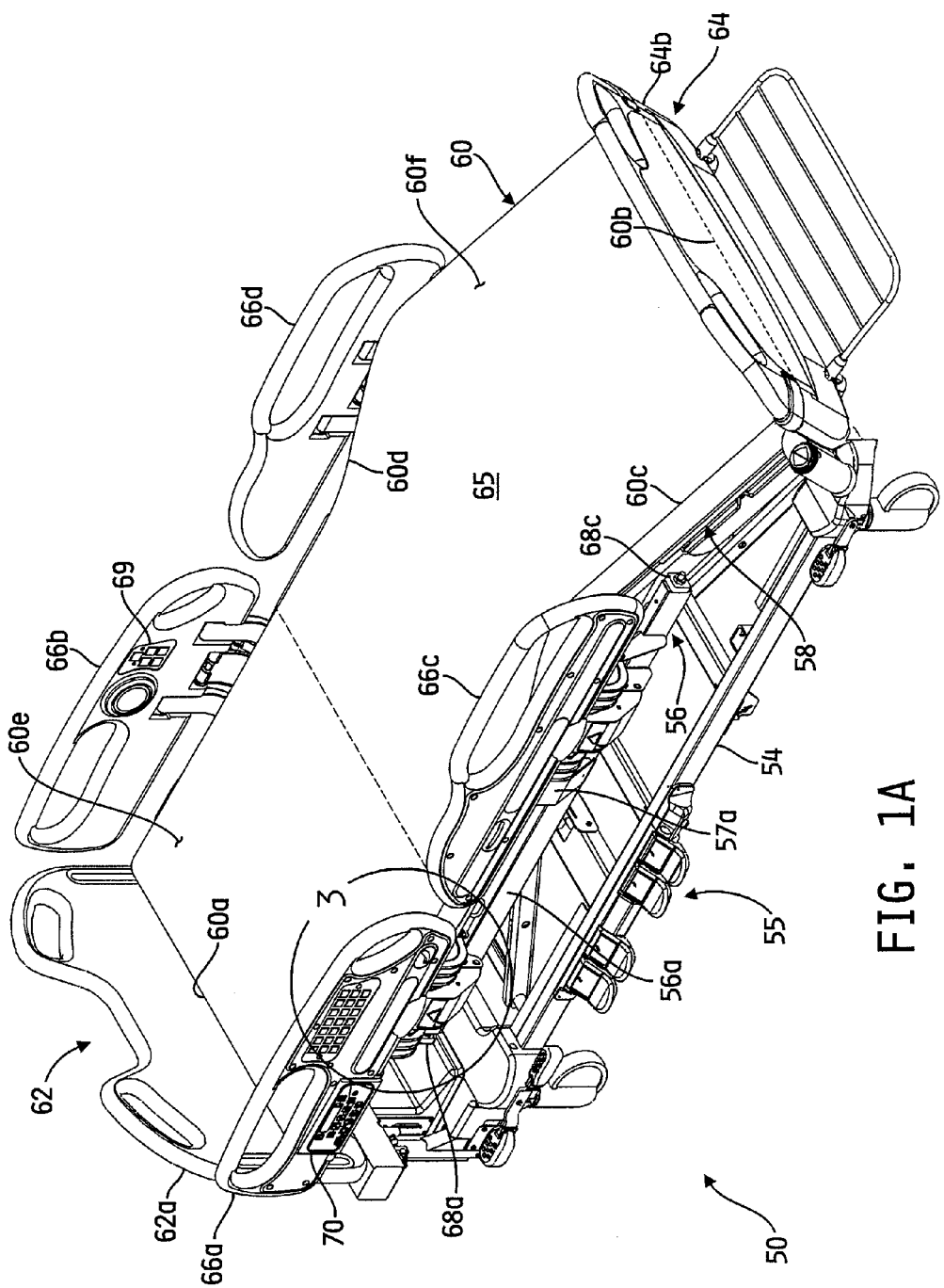
FIG. 1A is a perspective view of a hospital bed including an exemplary embodiment of a system for monitoring patient movement on, exit from, and impending exit from, the bed.

For the purposes of promoting an understanding of the principles of the invention, reference will now be made to one or more illustrative embodiments shown in the drawings and specific language will be used to describe the same. It will nevertheless be understood that no limitation of the scope of the invention is thereby intended.

Figure 1B:
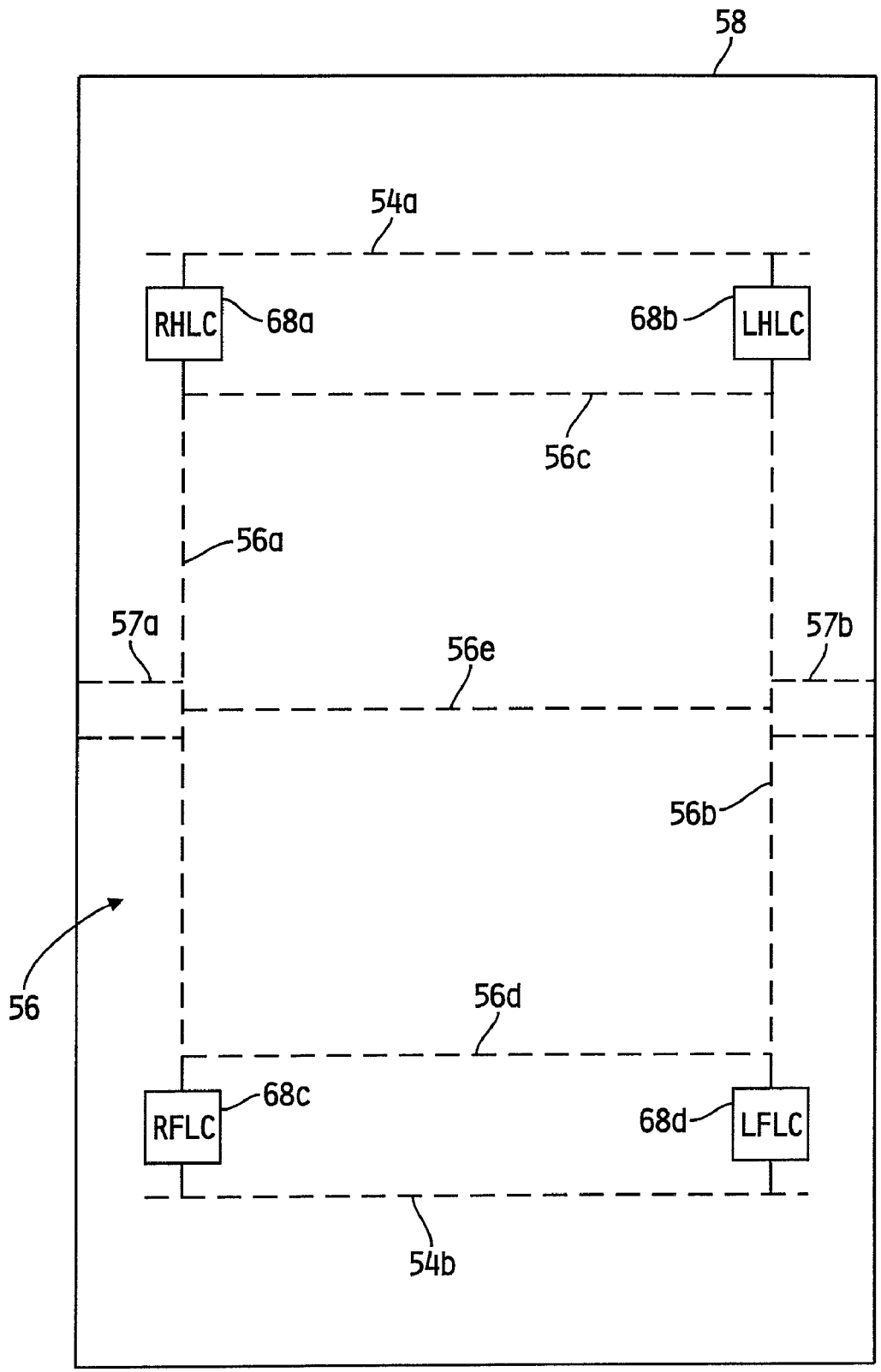
FIG. 1B is a block diagram illustrating exemplary locations of a number of load cells relative to the bed of FIG. 1A.
Figure 1C:
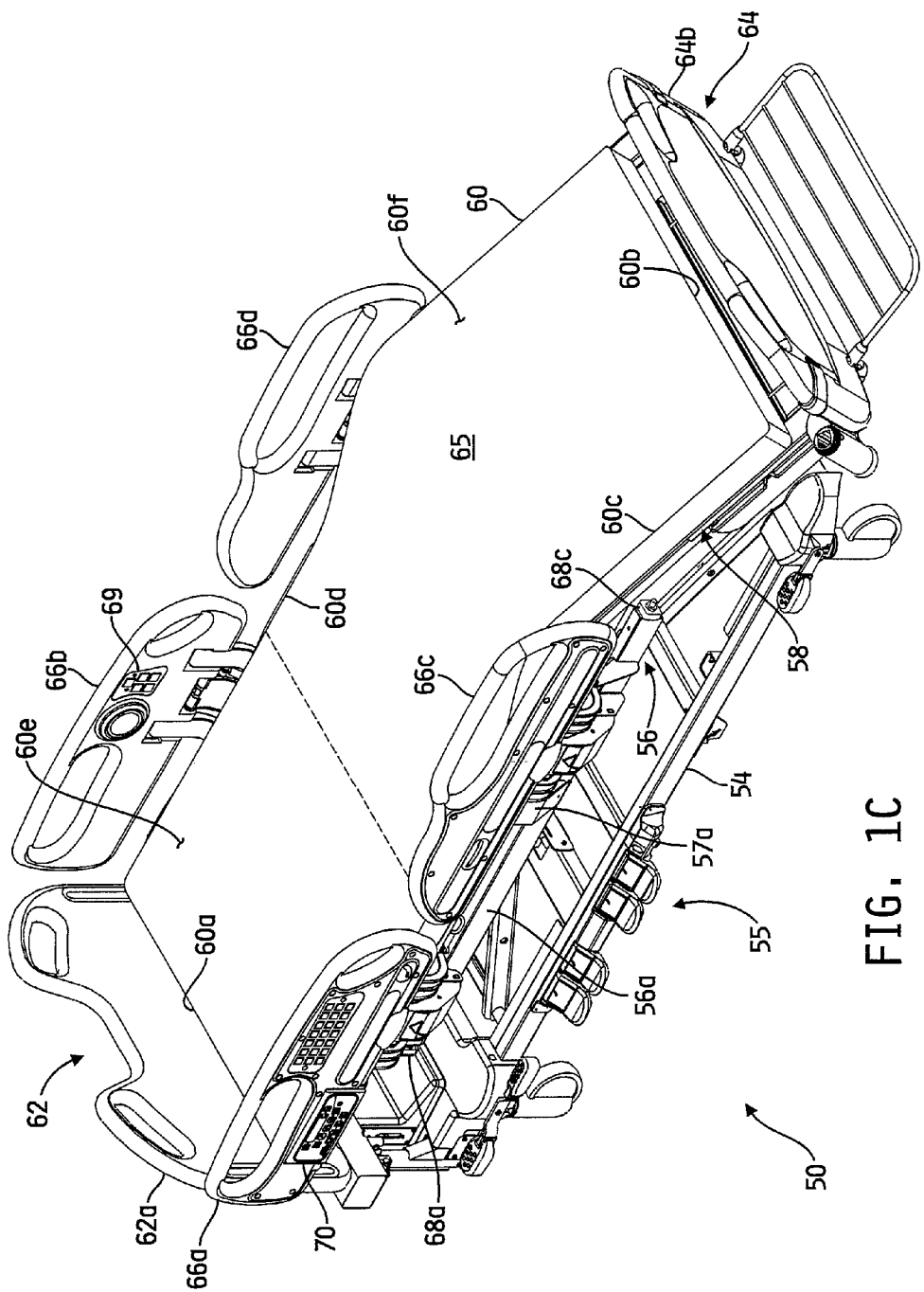
FIG. 1C is a perspective view illustrating the hospital bed of FIG. 1A with the foot end of the bed shown in an extended position.

Referring now to FIGS. 1A-1C, one illustrative embodiment of a hospital bed 50 is shown. The bed 50 is implemented in the context of a hospital bed and patient monitoring apparatus generally of the type described in U.S. Pat. No. 6,208,250, issued Mar. 27, 2001, and entitled Patient Position Detection Apparatus for a Bed, which is assigned to the assignee of the present invention, and the disclosure of which is incorporated herein by reference. In the exemplary embodiment shown and described herein, the hospital bed 50 may illustratively be a VersaCare® hospital bed, which is commercially available from Hill-Rom Company, Inc. of Batesville, Ind. It will be appreciated, however, that this implementation and the illustrated embodiment is provided only by way of example, and that the concepts illustrated and described herein are applicable to other patient support systems, including for example, but not limited to, stretchers, wheelchairs, or other patient-supporting apparatus. Any such other systems utilizing the concepts illustrated and described herein are contemplated by this disclosure.

The exemplary hospital bed 50 includes a stationary base 54 coupled to a weigh frame 56 that is mounted via frame members 57a and 57b to an adjustably positionable mattress support frame or deck 58 configured to support a conventional foam mattress 60. The mattress 60 defines a patient support surface 65 bounded by a head end 60a positioned adjacent to a headboard 62 mounted to the mattress support frame 58 at a head end 62 of the bed 50, a foot end 60b positioned adjacent to a footboard 64b mounted to the mattress support frame 58 at a foot end 64 of the bed 50, a left side 60c and a right side 60d. A pair of siderails 66a and 66c are mounted to the mattress support frame 58 adjacent to one side 60c of the mattress 60, and another pair of siderails 66b and 66d are mounted to the mattress support frame 58 adjacent to the opposite side 60d of the mattress 60. The siderail 66a supports a patient monitoring control panel 70, and the siderail 66b supports a mattress position control panel 70. The bed 50 is generally configured to adjustably position the mattress support 58 relative to the base 54.

Conventional structures and devices may be provided to adjustably position the mattress support 58, and such conventional structures and devices may include, for example, linkages, drives, and other movement members and devices coupled between base 54 and the weigh frame 56, and/or between weigh frame 56 and mattress support frame 58. Control of the position of the mattress support frame 58 and mattress 60 relative to the base 54 or weigh frame 56 is provided, for example, by a patient control pendant (not shown), a mattress position control panel 69, and/or a number of mattress positioning pedals 55. The mattress support frame 58 may, for example, be adjustably positioned in a general incline from the head end 62 to the foot end 64 or vice versa. Additionally, the mattress support 58 may be adjustably positioned such that the head end 60a of the mattress 60 is positioned between minimum and maximum incline angles, e.g., 0-65 degrees, relative to horizontal or bed flat, and the mattress support 58 may also be adjustably positioned such that the thigh area 60*f* of the mattress 60 is positioned between minimum and maximum bend angles, e.g., 0-35 degrees, relative to horizontal or bed flat. Those skilled in the art will recognize that the mattress support frame 58 or portions thereof may be adjustably positioned in other orientations, and such other orientations are contemplated by this disclosure.

A number of load cells are positioned between the weigh frame 56 and the base 54, wherein each load cell is configured to produce a voltage or current signal indicative of a weight impressed on that load cell from the weigh frame 56 relative to the base 54. In the illustrated embodiment, four such load cells are positioned between the weigh frame 56 and the base 54; one each near a different corner of the bed 50. Two such load cells 68*a* and 68*c* are shown in FIG. 1A, and all four are shown in FIG. 1B. Some of the structural components of the bed 50 will be designated hereinafter as "right", "left", "head" and "foot" from the reference point of an individual lying on the individual's back on the support surface 65 of the mattress with the individual's head oriented toward the head end 62 of the bed 50 and the individual's feet oriented toward the foot end 64 of the bed 50. For example, the weigh frame 56 illustrated in FIG. 1B includes a head end frame member 56*c* mounted at one end to one end of a right side weigh frame member 56*a* and at an opposite end to one end of a left side frame member 56*b*. Opposite ends of the right side weigh frame member 56*a* and the left side weigh frame member 56*b* are mounted to a foot end frame member 56*d*. A middle weigh frame member 56*e* is mounted at opposite ends to the right and left side weigh frame members 56*a* and 56*b* respectively between the head end and foot end frame members 56*c* and 56*d*. The frame member 57*a* is shown mounted between the right side frame member 56*a* and the mattress support frame 58, and the frame member 57*b* is shown mounted between the left side frame member 56*b* and the mattress support frame 58. It will be understood that other structural support is provided between the weigh frame member 56 and the mattress support frame 58, although only the frame members 57*a* and 57*b* are shown in FIGS. 1A-1C for ease of illustration.

A right head load cell (RHLC) 68*a* is illustratively positioned near the right head end of the bed 50 between a base support frame 54*a* secured to the base 54 near the head end 62 of the bed and the junction of the head end frame member 56*c* and the right side frame member 56*a*, as shown in the block diagram of FIG. 1B. A left head load cell (LHLC) 68*b* is illustratively positioned near the left head end of the bed 50 between the base support frame 54*a* and the junction of the head end frame member 56*c* and the left side frame member 56*b*, as illustrated in FIGS. 1A-1C and 3. A right foot load cell (RFLC) 68*c* is illustratively positioned near the right foot end of the bed 50 between a base support frame 54*b* secured to the base 54 near the foot end 64 of the bed 50 and the junction of the foot end frame member 56*d* and the right side frame member 56*a*, as shown in the block diagram of FIG. 1B. A left foot load cell (LFLC) 68*d* is illustratively positioned near the left foot end of the bed 50 between the base support frame 54*b* and the junction of the foot end frame member 56*d* and the left side frame member 56*b*, as illustrated in FIGS. 1A-1C. It should be noted that in FIGS. 1A and 1C, the base support frame 54*b* coupled to the left foot load cell 68*d* is not shown so that the exemplary position of the load cell 68*d* relative to the weigh frame 56, and to the bed 50 generally, can be seen. In the exemplary embodiment illustrated in FIG. 1B, the four corners of the mattress support frame 58 are shown extending beyond the four corners of the weigh frame 56, and hence beyond the positions of the four load cells 68*a*-68*d*.

In the illustrated embodiment, each of the load cells 68*a-d* are weight sensors of the type having resistive strain gauges coupled to a deflectable block (not shown), and structurally couple the weigh frame 56 to the base 54. It will be appreciated, however, that other weight detection devices may alternatively be used, wherein such alternative devices may be or include, but are not limited to, linear variable displacement transducers (LVDTs) and/or other weight detection devices operable in accordance with known capacitive, inductive, or other physical principles. In any case, all such alternative weight detection devices are contemplated by this disclosure.

As shown in FIG. 1C, one exemplary embodiment of the hospital bed 50 includes a foot end 64 that may be moved between a retracted position, as shown in FIG. 1A, and an extended position, as shown in FIG. 1C. The extended position of foot end 64 may be used, for example, to accommodate varying patient sizes and/or to provide a support surface between the foot end 60*b* of the mattress 60 and the footboard 64*b* to accommodate placement thereon of medical or other equipment.

Figure 2:
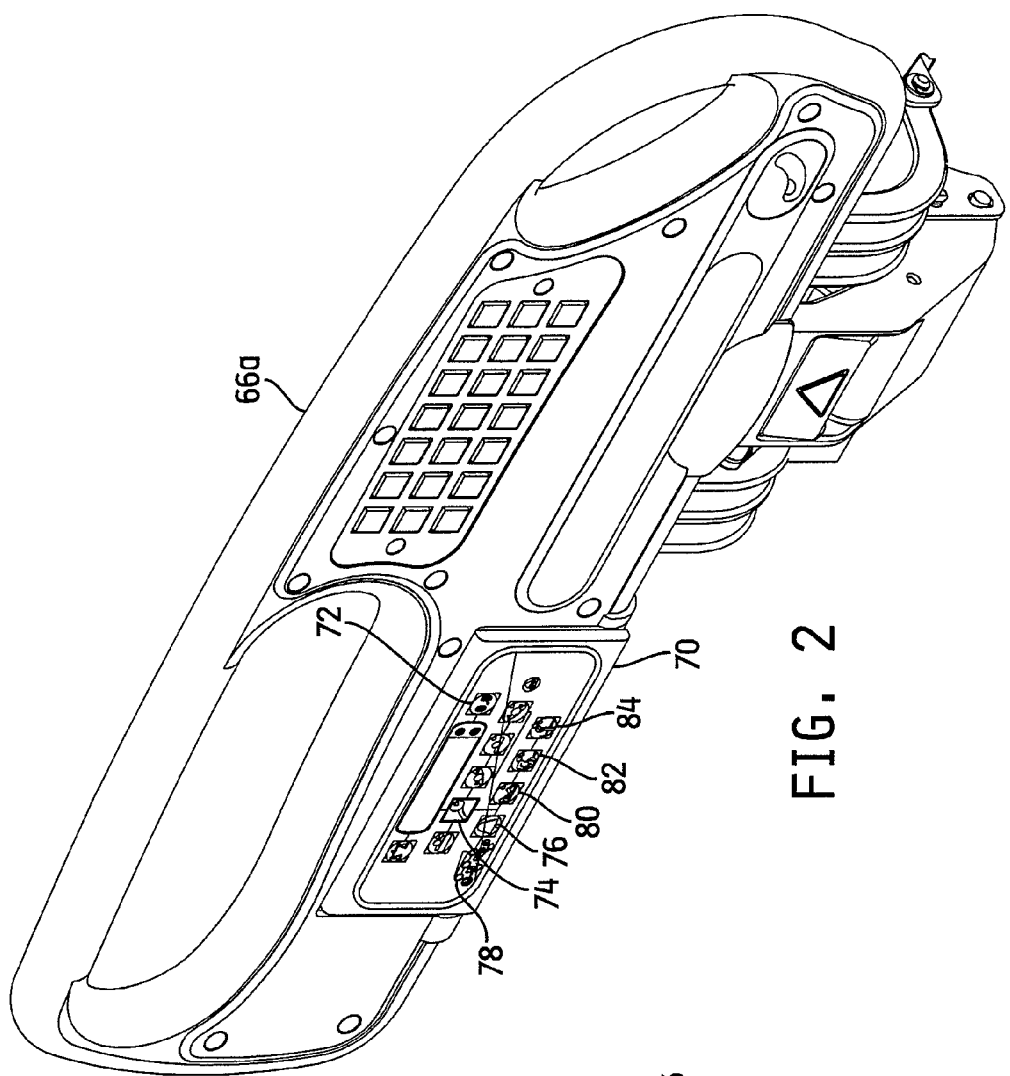
FIG. 2 is a perspective view of one of the siderails of the bed shown in FIG. 1A having a control and display panel mounted thereto.

Referring to FIG. 2, details of one exemplary control panel 70 mounted to the siderail 66*a* of the bed 50 of FIGS. 1A-1C is shown. The control panel 70 includes various user-interface components including, for example, a zero select switch 72, an enable or key switch 74, a volume control switch 76, a volume strength indicator 78, a movement mode switch 80, an exit mode switch 82 and an out-of-bed mode switch 84. The zero select switch 72 may be actuated to calibrate an empty bed weight; i.e., with out a patient on the mattress 60, and the enable or key switch 74 is used to enable various patient monitoring functions as will be described in greater detail hereinafter. The volume control switch 76 may be actuated to control the volume of a local alarm; i.e., an audible, visual and/or other alarm (not shown) mounted to or near the bed 50, and the volume strength indicator 78 may, for example, include a number, e.g., 3, of visual indicators, e.g., LED's, that are selectively activated to indicate a volume level of the local alarm. The mode switches 80-84 may be individually actuated to select between various patient monitoring modes. For example, actuation of the movement mode switch 80 selects a patient movement monitoring mode that monitors certain patient movement within the bed 50. Actuation of the exit mode switch 82 selects a patient exit, which may also be referred to as a bed exit, monitoring mode that monitors impending exit of the patient from the bed 50, and actuation of the out-of-bed mode switch 84 selects an out-of-bed (OOB) monitoring mode that monitors when at least a portion of the patient's weight is not supported by the weigh frame 56, thereby indicating that the patient is exiting, or has exited, the bed 50. Further details relating to the operation of each of these patient monitoring modes will be described in greater detail hereinafter. The control panel 70 illustrated in FIG. 2 includes additional switches and other components that provide for monitoring and control of other features of the bed 50.

Figure 3:
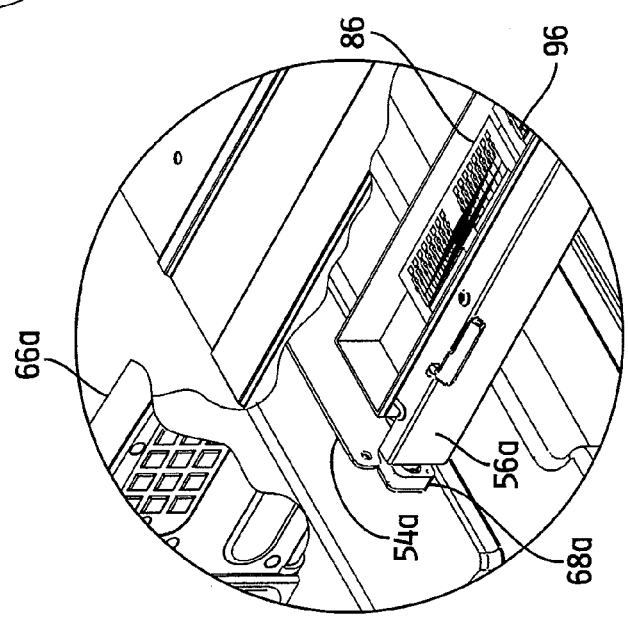
FIG. 3 is a partial cutaway view of the circled portion 3 of FIG. 1A illustrating control circuitry and one of the load cells carried by the bed.
Figure 4:
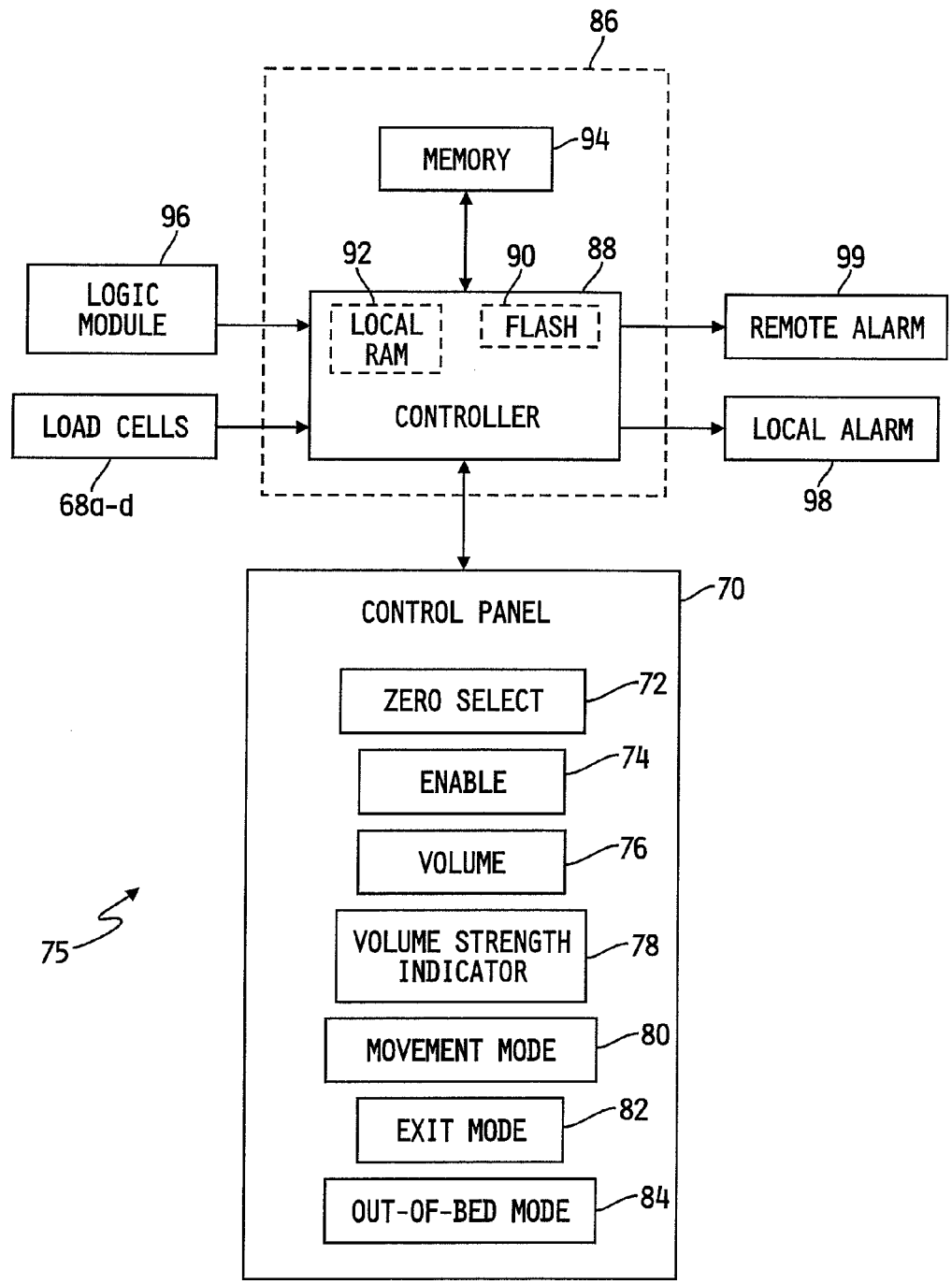
FIG. 4 is a block diagram of one exemplary embodiment of a monitoring system for monitoring patient movement on, exit from, and impending exit from, the bed illustrated in FIGS. 1A-3.

Referring now to FIG. 3, the right side frame member 56*a* of the weigh frame 56 includes a housing mounted thereto adjacent to the base support frame 54*a*. The housing is configured to carry a processor module 86 and a logic module 96 electrically coupled thereto. In the exemplary embodiment, the processor module 86 forms part of a patient monitoring control system and includes a number of executable software algorithms for controlling operation of the system, and one illustrative embodiment of such a patient monitoring system 75 is shown in FIG. 4. The patient monitoring system 75 includes the processor module 86 electrically coupled to the logic module 96, the load cells 68a-68d, the control panel 70, a local alarm 98 (mounted to or near the bed 50) and a remote alarm 99. The remote alarm 99 is located near a caregiver or other patient monitoring individual, and is controlled by the processor module 86 to alert the remote caregiver or other patient monitoring individual via an audible and/or visual or other alarm (not shown) of certain patient movement activities as will be described in greater detail hereinafter.

The processor module 86 includes a microprocessor-based controller 88 having a Flash memory unit 90 and a local RAM memory unit 92. The module 86 further includes an auxiliary memory unit 94, which may be an EEPROM or other conventional memory unit that is electrically connected to the controller 88. The logic module 96 and load cells 68a-68d are electrically connected to the controller 88, and in the exemplary embodiment the logic module 96 is configured to continually determine a height of the bed 50 via one or more conventional sensors and to supply the bed height information to the controller 88. Alternatively, the controller 88 may be operable to determine the height of the bed 50 via any one or more conventional techniques. In any case, the controller 88 is also electrically connected to the local alarm 98 and to the remote alarm 99, and the controller 88 is configured to control operation of such alarms 98 and 99 in a conventional manner. The control panel 70 is also electrically connected to the controller 88 to communicate information from the various switches and other input devices 72-76 and 80-84 from the control panel 70 to the controller 88, and to communicate information from the controller 88 to the volume strength indicator 78.

Figure 5:
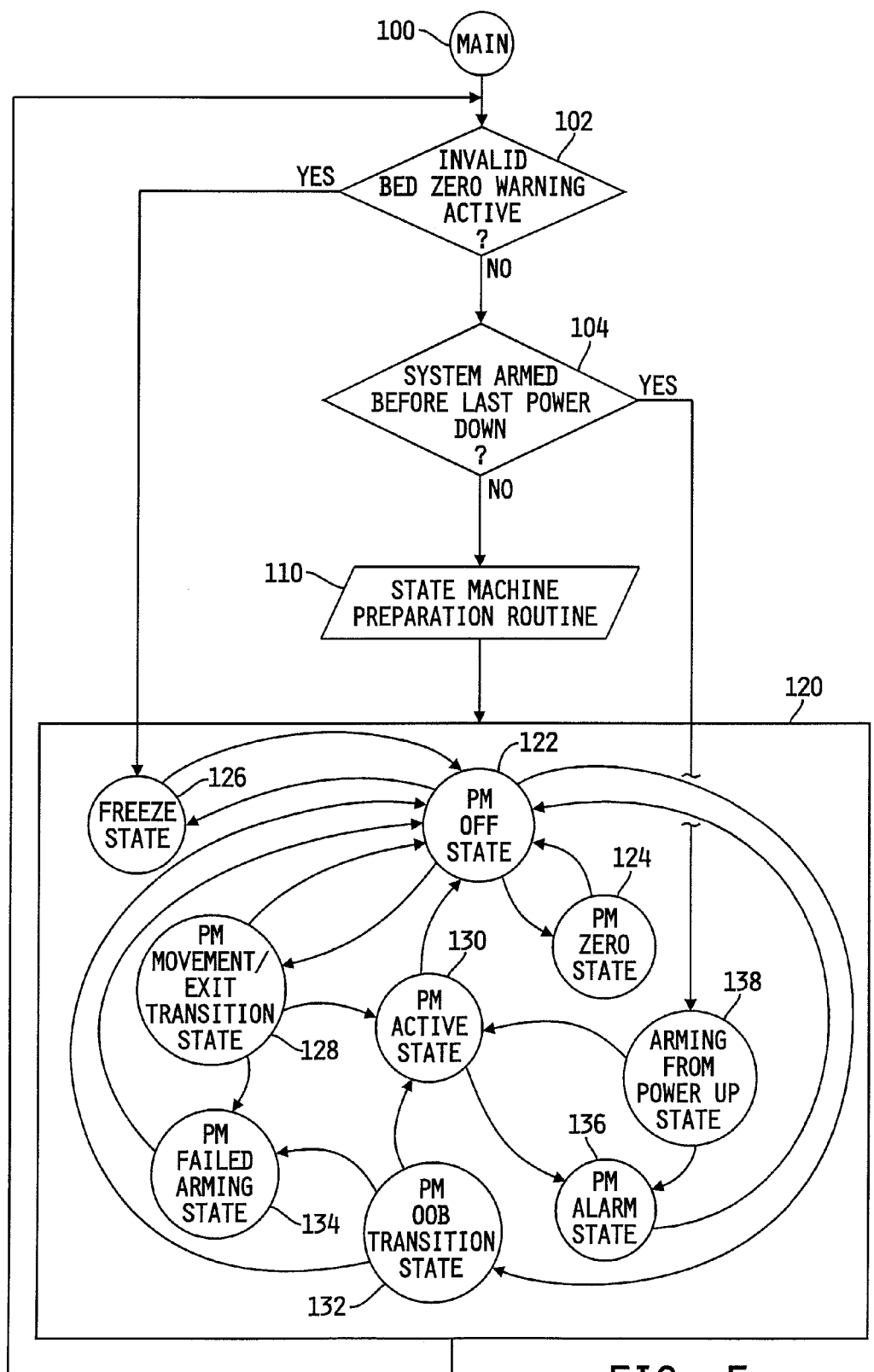
FIG. 5 is a combined flowchart and state diagram illustrating one exemplary embodiment of a software algorithm for monitoring patient movement on, exit from, and impending exit from, the bed illustrated in FIGS. 1A-3.

In the illustrated embodiment, the Flash memory 90 of the processor module 86 includes a number of software algorithms and other data that are executable by the controller 88 to monitor patient movement relative to a reference load cell distribution, impending exit from the mattress 60 and/or exit from the mattress 60. An exemplary main software algorithm 100 for managing such functions is illustrated in FIG. 5 in the form of a combined flowchart and state machine 120. The software algorithm 100 is executed periodically by the controller 88, e.g., once every 200 ms, to monitor patient movement relative to a reference load cell distribution, impending exit from the mattress 60 and/or exit from the mattress 60. Referring to FIG. 5, the software algorithm 100 begins at step 102 where the controller 88 is operable to determine whether an invalid bed zero warning is active upon power up, wherein an invalid bed zero warning indicates that the zero reference weight of the bed 50, e.g., the total weight impressed upon the weigh frame 56 without a patient supported by the mattress 60, may not be current or accurate. If, at step 102, the controller 88 determines that an invalid bed zero warning is active upon power up, algorithm execution advances to a Freeze State 126 of the state machine 120. The controller 88 is operable in the Freeze State 126 to wait until a bed weight zeroing process is activated as will be described below. If, at step 102, the controller 88 instead determines that an invalid bed zero warning is not active upon power up, execution of the algorithm 100 advances to step 104 where the controller 88 is operable to determine whether the patient monitoring system 75 was armed, i.e., whether one of the patient monitoring modes was active, before the last power down of the system 75. The system 75 is operable to save the current data to the memory unit 94 at power down, and to recall such data from the memory unit 94 upon subsequent power up so that the controller 88 may make the determination illustrated in step 104.

The patient monitoring modes include a patient movement (PM) mode wherein the system 75 is operable to monitor movement of a patient on the mattress 60 by monitoring weight distribution among two or three of the four load cells 68a-68b relative to a predefined set of PM load cell threshold data, a patient exit (PE) mode wherein the system 75 is operable to monitor impending exit from the mattress 60 by monitoring weight distribution of the four load cells relative to a predefined set of PE load cell threshold data, and a patient out-of-bed (OOB) mode wherein the system 75 is operable to monitor exit of the patient from the mattress 60 by monitoring the patient weight distributed over the four load cells relative to an armed patient weight, wherein the armed weight corresponds to the patient weight distributed over the four load cells when the patient monitoring mode was armed as will be described in greater detail hereinafter. In any case, if the controller 88 determines at step 104 that the system 75 was not armed before the last system power down, execution of the algorithm 100 advances to step 110 where the controller 88 is operable to execute a state machine preparation routine. If, at step 104, the controller 88 instead determines that the system 75 was armed before the last system power down, execution of the algorithm 100 advances to an Arming From Power Up Transition State 138 of the state machine 120 where the patient weight is processed to determine whether it is contained within a defined armed range prior to advancing to the PM Active State 130 of the state machine 120 to resume operation of the patient monitoring mode that was active at the last system power down.

After executing the state machine preparation routine at step 110, execution of the algorithm 100 advances to the state machine 120. In the first execution of the algorithm 100, the state machine 120 is started at the PM Off State 122. In further executions of the algorithm 100, the state machine 120 will be entered from step 110 at its current operational state. In addition to the operating and transition states just described, the state machine 120 further includes a PM Movement/Exit Transition State 128 that is selected for operation following the PM Off State 122 when either a request for Patient Monitoring (PM) Mode or Patient Exit (PE) Mode is received via the control panel switch 80 or 82 respectively. From the PM Movement/Exit Transition State 128, the state machine 120 advances to the PM active state 130 where the controller 88 is operable to actively monitor patient activity pursuant to the PM mode or PE mode respectively. The state machine 120 also includes a PM OOB Transition State 132, that is similar to the PM Movement/Exit Transition State 128 and that is selected for operation following the PM Off State 122 when a request for out-of-bed (OOB) mode is received via the control panel switch 84. From the PM OOB Transition State 132, the state machine 120 advances to the PM active state 130 where the controller 88 is operable to actively monitor patient activity pursuant to the OOB mode.

From either of the PM Movement/Exit Transition state 128 or the PM OOB Transition State 132, the state machine 120 advances to a PM Failed Arming State 134 if either of the transition states 128 or 132 failed the arming function; i.e., failed to arm the system 75 by determining a total patient weight. From the PM Failed Arming state 134, the state machine 120 advances back to the PM Off State where the patient may be repositioned relative to the mattress 60, followed by selection of the PM, PE or OOB mode.

From either of the PM Active state 130 or the Arming from Power Up State 138, the state machine 120 advances to a PM Alarm State 136 if any alarm conditions are met in the PM Active State 130 or the patient weight arming conditions are not met in the Arming from Power Up State 138. From the PM Alarm State 136, the state machine 120 advances to the PM Off State 122 where the alarm condition may be remedied and/or the patient may be repositioned relative to the mattress 60 before re-selecting the PM or PE mode. The state machine 120 further includes a PM Zero State 124 that is selected to compute a new zero weight bed reference upon actuation of a predefined combination of the switches forming part of the control panel 70 as will be described below.

Figure 6:
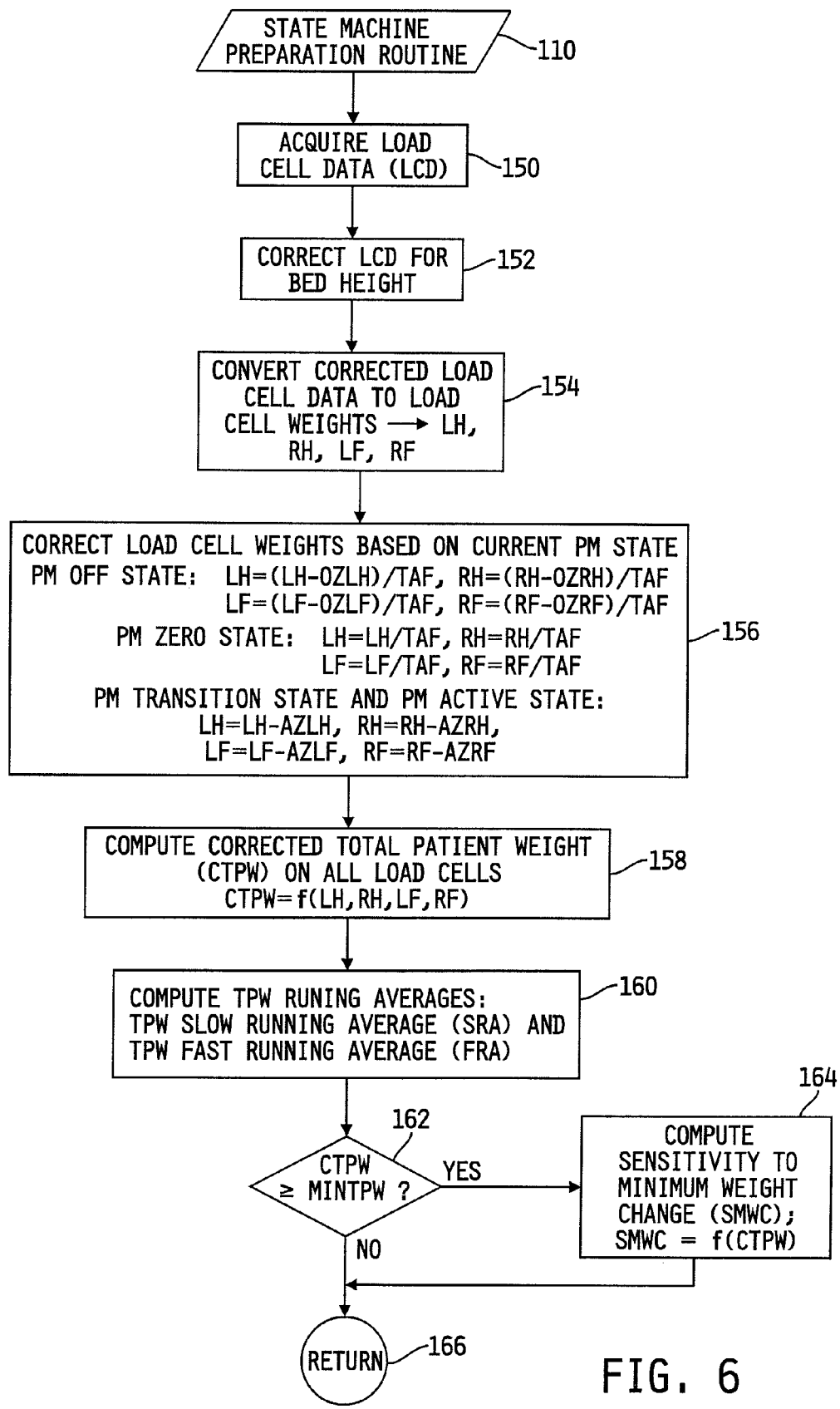
FIG. 6 is a flowchart illustrating an exemplary embodiment of the state machine preparation routine forming part of the algorithm of FIG. 5.

Referring now to FIG. 6, a flowchart is shown of one illustrative embodiment of the state machine preparation routine called by step 112 of the algorithm 100 of FIG. 5. In the illustrated embodiment, the state machine preparation routine begins at step 150 where the controller 88 is operable to acquire new load cell data, LCD, by sampling the signals produced by the load cells 68a-68d. Thereafter at step 152, the controller 88 is operable to correct the load cell data, LCD, as a function of the current bed height. In the illustrated embodiment, the various structures and mechanisms used to raise and lower the height of the mattress support frame 58 relative to the base 54 to cause the weights measured by the load cells 68a-68d to vary as a function of bed height. In this embodiment, the logic module 96 is coupled to one or more sensors from which the logic module is operable to determine bed height in a known manner, and the logic module 96 supplies the bed height information to the process module 86. Alternatively, the controller 88 may be operable to determine the height of the bed 50 via any one or more conventional techniques. In any case, the memory unit 90 illustratively includes a bed height conversion function in the form of a lookup table or other conversion function mapping the bed height information to load cell signal correction information. In one embodiment, for example, the lookup table maps discrete bed height values to corresponding offset values, and the offset value corresponding to the current bed height is then used to correct the load cell data, LCD, by adding the offset value to the values produced by two diagonally opposed pairs of the load cells 68a-68d, and subtracting the offset value from the values produced by the remaining two diagonally opposed pairs of the load cells 68a-68d. Those skilled in the art will recognize other techniques for correcting the signals or values produced by the load cells 68a-68d as a function of bed height, and such other techniques are intended to fall within the scope of claims appended hereto.

Following step 152, the controller 88 is operable at step 154 of the state machine preparation routine to convert the corrected load cell data signals to load cell weight values. Hereinafter, the term "RH" may be used to identify the bed height-corrected weight value produced by the right head load cell 68a, the term "LH" may be used to identify the bed height-corrected weight value produced by the left head load cell 68b, the term "RF" may be used to identify the bed height-corrected weight value produced by the right foot load cell 68c, and the term "LF" may be used to identify the bed height-corrected weight value produced by the left foot load cell 68d. In the illustrated embodiment, the load cell signals produced by the load cells 68a-68d are analog current or voltage signals, and the amplitudes of these analog signals are converted via analog-to-digital inputs of the controller 88 to corresponding discrete, raw "count" values. The controller 88 is then operable at step 152 to add or subtract an offset count value to or from the various discrete, raw count values, as just described, to produce bed height-corrected count values for each of the load cells 68a-68d. At step 154, the controller 88 then multiplies the corrected count values of each the load cell by a predefined conversion constant to convert the corrected count values of each load cell to a corresponding weight value, LH, LF, RH and RF.

Following step 154, the controller 88 is operable at step 156 to correct the load cell weight values, LH, RH, LF and RF based on the current PM State of the state machine 120. For example, if the state machine 120 is currently in the PM Off State 122, the controller 88 is operable to correct the load cell weight values by subtracting tare weights in the form of original zero weight (OZ) values, and then by correcting these weight difference values by a trend angle, or reverse trend angle, factor, TAF. In one embodiment, the controller 88 is operable to determine a trend angle or reverse angle, $\alpha$, corresponding to the angle of incline or decline of the entire mattress 60 from the head end 62 of the bed 50 to the foot end 64 of the bed 50, as a function of bed height difference between the head end 62 and foot end 64 of the bed 50. In this embodiment, the logic module 96 supplies the bed height information to the processor module 86, and the controller 88 is operable to determine the trend angle, $\alpha$, as a known function of the bed height difference between the head end 62 and foot end 64 of the bed 50. Alternatively, the controller 88 may be configured to determine a via conventional techniques. In any case, with the trend angle, $\alpha$, determined, the controller 88 is then operable to compute the trend angle factor according to the relationship TAF=$\cos \alpha$. As illustrated in step 156, the controller 88 is thus operable to correct the load cell weight values when the state machine 120 is in the PM Off State 122 according to the equations LH=(LH−OZLH)/TAF, RH=(RH−OZRH)/TAF, LF=(LF−OZLF)/TAF and RF=(RF−OZRF)/TAF.

If, at step 156, the state machine 120 is instead in the PM Zero State 124, the controller 88 is operable to correct the load cell weight values by the trend angle, or reverse trend angle, factor, TAF. As illustrated in step 156, the controller 88 is operable to correct the load cell weight values when the state machine 120 is in the PM Zero State 124 according to the equations LH=LH/TAF, RH=RH/TAF, LF=LF/TAF and RF=RF/TAF.

If, at step 156, the state machine 120 is instead in either of the PM Movement/Exit Transition state 128 or the PM Active State 130, the controller 88 is operable to correct the load cell weight values by tare weights in the form of auto zero (AZ) weight values. As illustrated in step 156, the controller 88 is operable to correct the load cell weight values when the state machine 120 is in the PM Movement/Exit Transition State 128 or the PM Active State 130 according to the equations LH=LH−AZLH, RH=RH−AZRH, LF=LF−AZLF and RF=RF−AZRF.

Following step 156, the controller 88 is operable to compute a corrected total patient weight, CTPW, corresponding to a total bed weight impressed upon the load cells 68a-68d by a patient. In one embodiment, the controller 88 is operable to execute step 156 by computing the total patient weight, CTPW, as an average of the sum of the corrected load cell weight values, or CTPW=(LH+RH+LF+RF)/4. It may also be desirable to further correct CTPW, as a function of the trend angle or reverse trend angle, $\alpha$, when CTPW is determined from load cell weight values when the state machine 120 is in either the PM Movement/Exit Transition State 128 or the PM Active State 130. In such cases, the controller 88 may further be operable at step 158 to compute CTPW=CTPW/$\cos\alpha$.

Following step 158, the controller 88 is operable at step 160 to compute a number of total patient weight running averages using any one or more conventional sample averaging techniques. In the illustrated embodiment, for example, the controller 88 is operable at step 160 to compute a total patient weight slow running average, SRA, and a total patient weight fast running average, FRA, using conventional averaging techniques, although other sample averaging techniques may be used to provide other patient weight running average values. At step 162, the controller 88 is operable to determine whether the corrected total patient weight, CTPW, is greater than a minimum total patient weight threshold, MINTPW. The minimum total patient weight threshold, MINTPW, may be selected to fit the particular application, and one example value of MINTPW may be, but should not be limited to, 50 lbs. If the controller 88 determines at step 162 that CTPW is greater than MINTPW, execution of the state machine preparation routine advances to step 164 where the controller 88 is operable to compute a sensitivity to minimum weight change, SMWC, as a function of the corrected total patient weight, CTPW, wherein the minimum weight change may result from adding weight to the support surface 65 of the mattress 60 and/or to the region of the mattress support frame 58 between the end 60b of the mattress and the foot end 64 of the bed 50 as illustrated in FIG. 1C. The sensitivity to minimum weight change is used, as will be described in detail hereinafter, to determine a maximum amount of weight change in the patient movement (PM) mode that will be tolerated before temporarily disabling the PM mode until the change in weight settles.

In one embodiment, for example, the controller 88 is operable to execute step 164 by computing SMWC according to the equation SMWC=MWCHBNR+(CTPW−MINTPW)*WCHS, where SMWC is the sensitivity to minimum weight change, MWCHBNR is a minimum weight change before new reference value, e.g., 5 lbs., CTPW is the corrected total patient weight, MINTPW is the minimum total patient weight threshold and WCHS is a weight change sensitivity value, e.g., 0.05. One example implementation of this equation may thus result in SMWC=5+(CTPW−50)*0.05, although other values of MWCHBNR, MINTPW and WCHS may be used. In any case, execution of the state machine preparation routine advances from step 164 and from the "NO" branch of step 162 to step 166 where algorithm execution is returned to step 110 of the main algorithm 100 of FIG. 5.

Figure 7A:
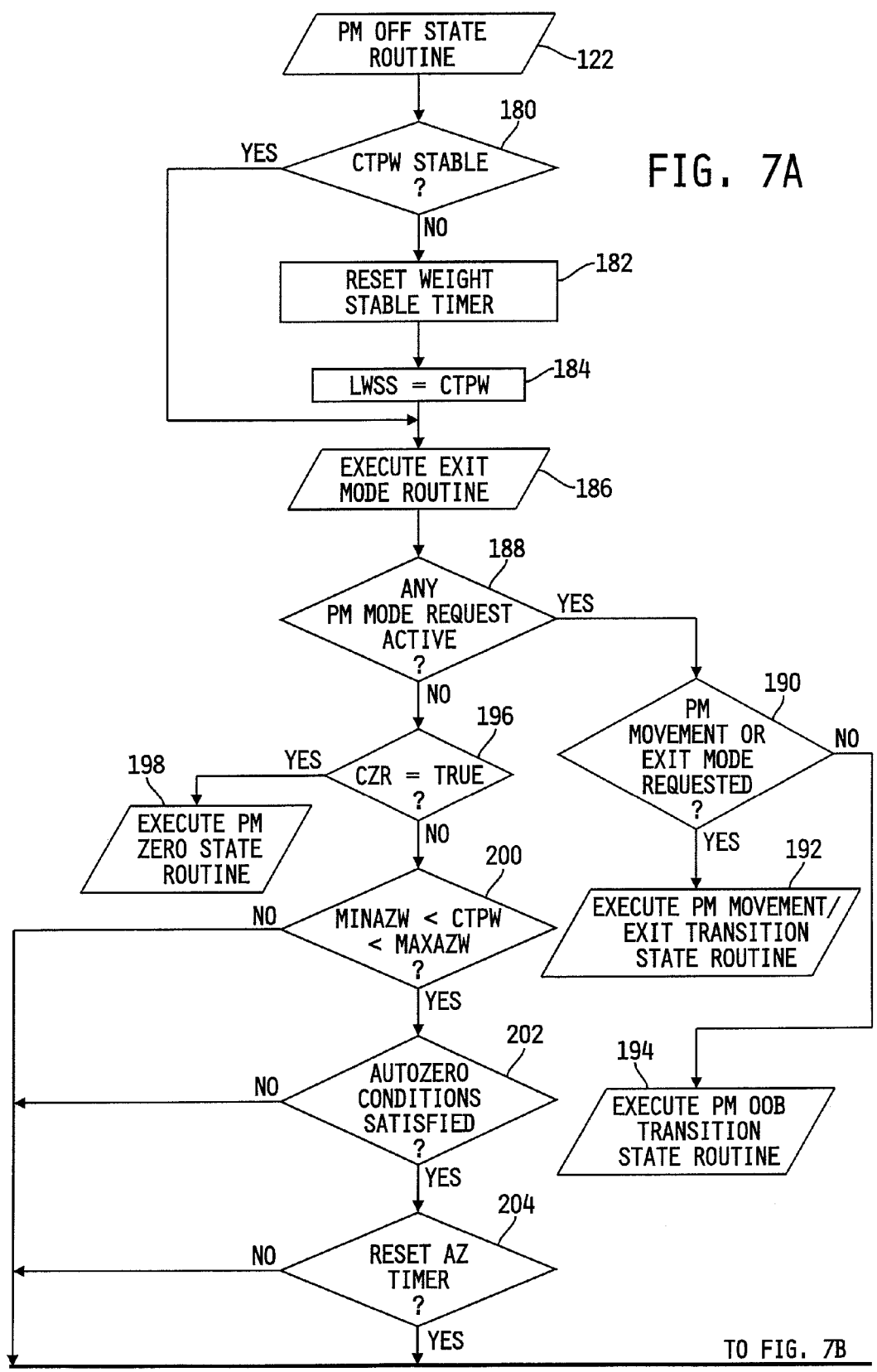
Figure 7C:
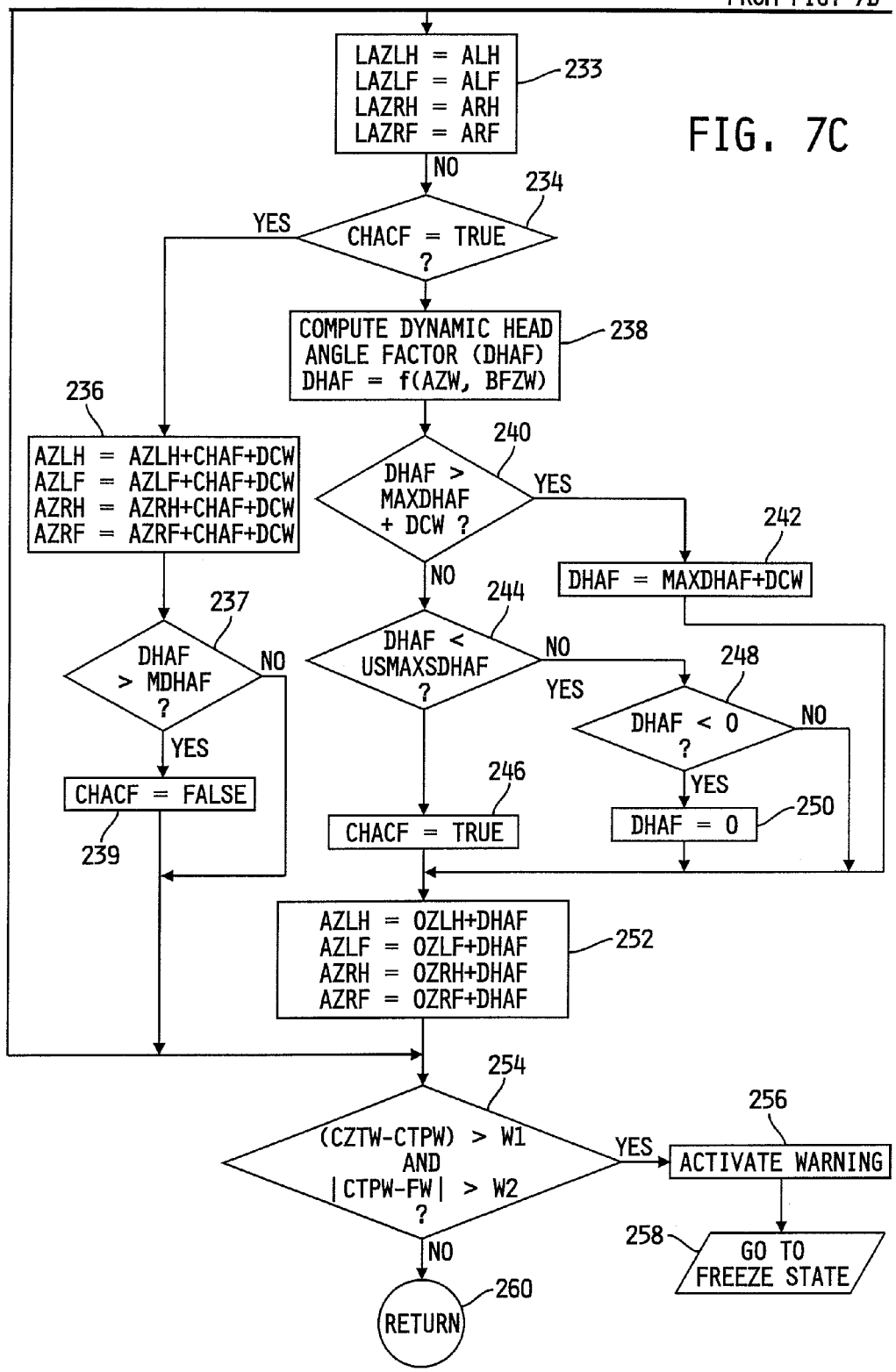

Following completion of the state machine preparation routine at step 110, execution of the algorithm 100 advances to the current state of the state machine 120. One such state may be, for example, the PM Off State 122. Referring now to FIGS. 7A-7C, a flowchart is shown of one illustrative embodiment of a software algorithm or routine for executing the PM Off State 122 of the state machine 120. The PM Off State routine begins at step 180 where the controller 88 is operable to determine whether the corrected total patient weight, CTPW, is stable. In one embodiment, the controller 88 is operable at step 180 to determine whether CTPW is stable by comparing CTPW to a sum and difference of a last weight settling snapshot, LWSS, and an arming weight settle constant, AWSC, wherein the last weight settling snapshot corresponds to the total weight impressed upon the load cells 68a-68d at the most recent determination that CTPW was stable. Specifically, the controller 88 is operable in the illustrated embodiment to determine that CTPW is unstable if CTPW>(LWSS+AWSC) OR CTPW<(LWSS−AWSC). If the controller 88 determines at step 180 that either of these conditions is met, execution of the routine advances to step 182 where the controller 88 is operable to reset a weight stable timer and capture a new weight reference snap shot. Thereafter at step 184, the controller 88 is operable to set the last weight settling snapshot, LWSS, to the corrected total patient weight, CTPW.

Execution of the PM Off State routine advances from the "YES" branch of step 180, which is indicative of CTPW satisfying neither of the above inequalities and therefore being considered to be stable, and from step 184 to step 186 where the controller 88 is operable to execute the Exit Mode routine, which will be described in detail hereinafter, to determine whether the patient weight is contained within a safe arming zone of the mattress 60. Thereafter at step 188, the controller 88 is operable to determine whether any patient monitoring mode requests; i.e., the patient movement (PM) mode, patient exit (PE) exit mode or patient out-of-bed (OOB) mode, are active. If so, execution of the PM Off State routine advances to step 190 where the controller 88 is operable to determine whether the patient monitoring mode request corresponds to either of the patient movement (PM) or patient exit (PE) monitoring modes. If so, the operating state of the state machine 120 moves to the PM Movement/Exit Transition State 128 and the controller 88 is operable at step 192 to execute a PM Movement/Exit Transition State routine, one example of which will be described below with reference to FIGS. 10A-10B. If, on the other hand, the controller 88 determines at step 190 that the patient monitoring mode request corresponds to the patient out-of-bed (OOB) monitoring mode, the operating state of the state machine 120 moves to the PM OOB Transition State 132 of the state machine 120 and the controller 88 is operable at step 194 to execute a PM OOB Transition State routine similar to the PM Movement/Exit Transition State routine, one embodiment of which will be described below with reference to FIGS. 10A-10B.

Figure 10A:
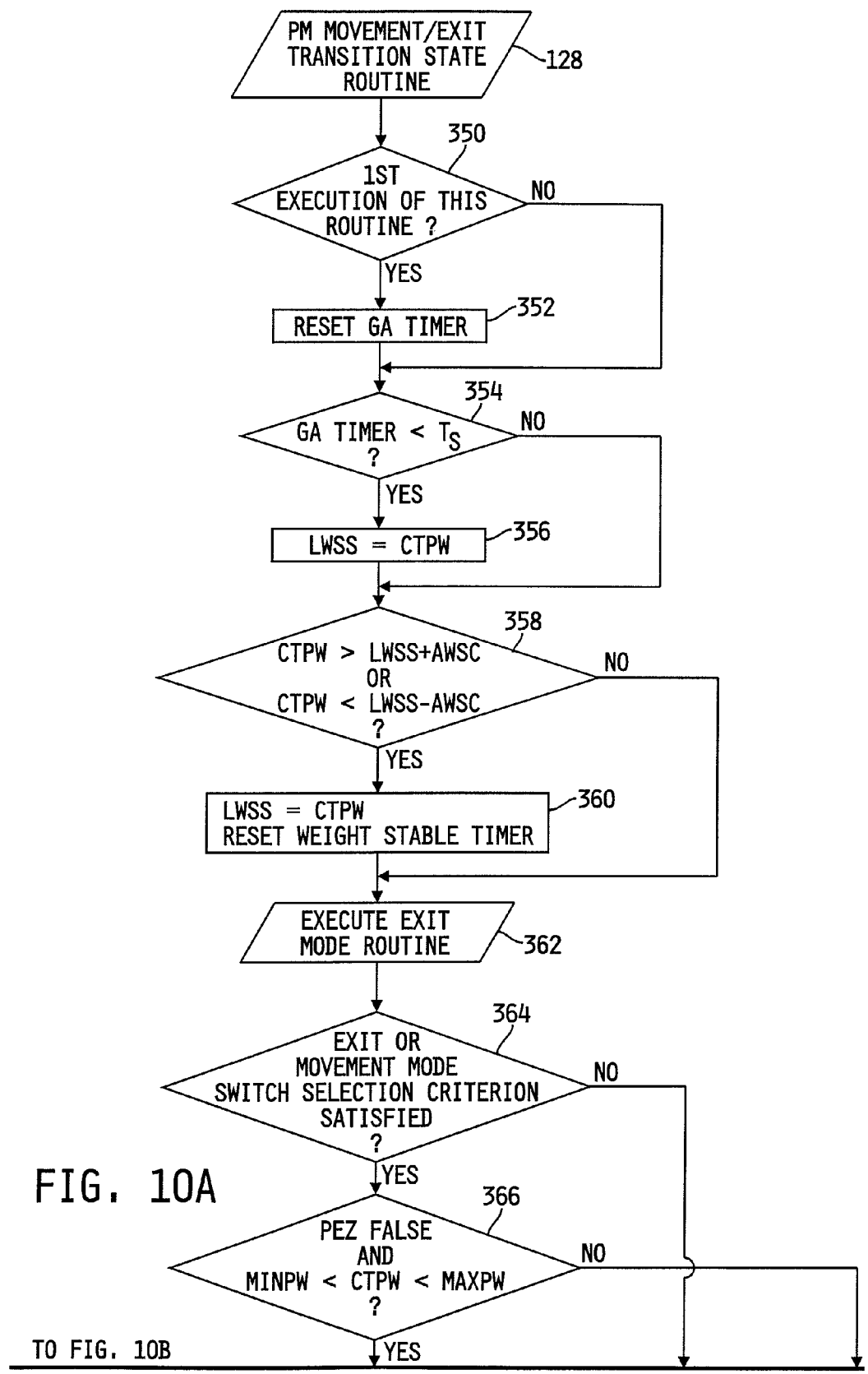
FIGS. 10A-10B show a flowchart illustrating an exemplary embodiment of a software routine for executing the PM Movement/Exit Transition State that forms part of the state machine of FIG. 5.
Figure 10B:
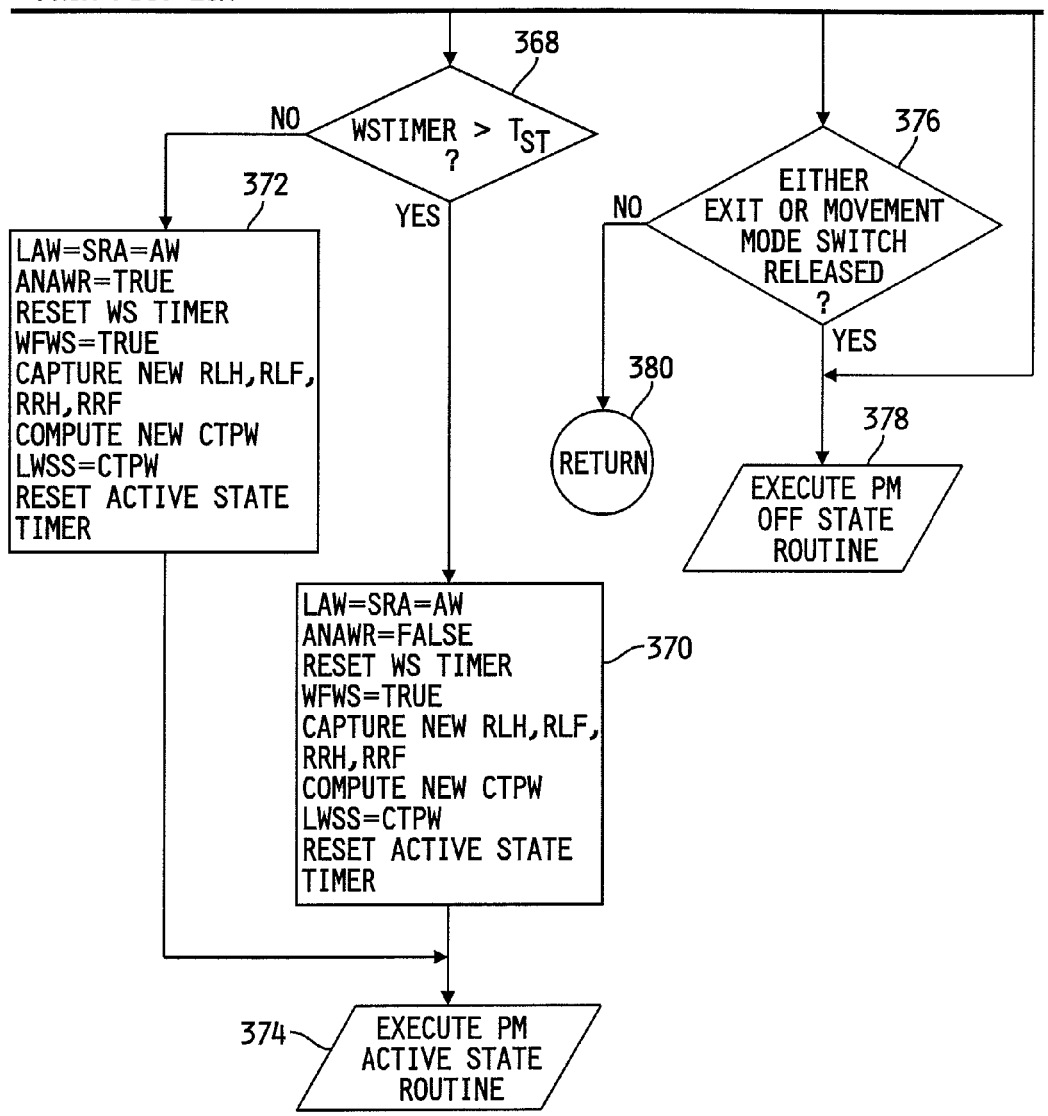

In the illustrated embodiment, the PM OOB Transition State routine may be identical to the PM Movement/Exit Transition State routine illustrated in FIGS. 10A-10B with the exception that step 362 is omitted and the Exit mode routine is therefore not executed to determine whether the patient weight is within the safe arming zone of the mattress 60. In all other respects, the PM OOB Transition State routine in the illustrated embodiment is identical to the PM Movement/Exit Transition State routine of FIGS. 10A-10B. A flowchart and description of the details such a PM OOB Transition State routine would thus be repetitious of the PM Movement/Exit Transition State routine of FIGS. 10A-10B, and is accordingly omitted from this document for brevity.

Returning to the PM Off State routine of FIGS. 7A-7C, execution of this routine advances from the "NO" branch of step 188 to step 196 where the controller 88 is operable to determine whether a common zero request flag, CZR, is active. This flag is set when a user pushes the enable switch 74 and thereafter pushes the zero select switch 72, thereby manually requesting zeroing of the bed weight. If the controller 88 determines at step 196 that CZR is "true", the operating state of the state machine 120 moves to the PM Zero State 124 and the controller 88 is operable at step 198 to execute a PM Zero State routine to zero the bed weight, and one example of such a PM Zero State routine will be described below with reference to FIG. 8.

Execution of the PM Off State routine advances from the "NO" branch of step 196 to step 200 where the controller 88 is operable to determine whether the corrected total patient weight, CTPW, is between a minimum auto-zero weight value, MINAZW, and a maximum auto-zero weight value, MAXAZW. When the state machine 120 is in the PM Off State the controller 88 executes steps 200 and beyond of the PM Off State routine to determine whether to perform an auto-zeroing process, or an automatic bed zeroing. MINAZW may be in the range of −4 to −5 lbs., and MAXAZW may be in the range of 4-5 lbs., although it will be understood that these values are provided only by way of example, and that MINAZW and MAXAZW may take on any desired values. The auto-zeroing process of steps 200 and beyond is conducted because the weight distribution between the load cells 68a-68d may have shifted since the last bed zeroing event. Such a shift may have occurred for any number of reasons including, for example, a visitor sits on the corner of the bed for a brief time period, someone leans against one of the siderails 66a-66d, medical monitoring equipment may have been briefly stored on the mattress 60 or between the end 60b of the mattress 60 and the foot end 64 of the bed 50, or the like. In any of these cases, the total bed weight after one or more such occurrences may remain at or near the zeroed bed weight, but the distribution of the weight between the various load cells 68a-68d may have shifted significantly. Such weight shifting between the load cells 68a-68d may compromise subsequent calculations made by the system 75, and it is accordingly desirable to carry out an auto-zeroing process whenever the state machine 120 is in the PM Off State 122 and conditions indicate that auto-zeroing is desirable.

In any case, if the controller 88 determines at step 200 that CTPW does not fall between MINAZW and MAXAZW, CTPW is too high to consider auto-zeroing and execution of the routine advances to step 254 for execution of a warning algorithm. If, on the other hand, the controller 88 determines at step 200 that CTPW falls between MINAZW and MAXAZW, the controller 88 is thereafter operable at step 202 to determine whether the auto-zero weight conditions are satisfied. In one embodiment, the controller 88 is operable at step 202 to determine whether the auto-zero weight conditions are satisfied by determining whether a patient exiting zone flag, PEZ, is false, thereby indicating that the patient is within the safe arming zone of the mattress, or whether the corrected total patient weight, CTPW is greater than a minimum auto-zero trigger weight, MINAZTW, or that CTPW is less than a maximum auto-zero trigger weight, MAXAZTW. As examples, MINAZTW may be in the range of −4 to −5 lbs., e.g., −4.1 lbs., and MAXAZTW may be in the range of 4-5 lbs., e.g., 4.1 lbs., although it will be understood that these values are provided only by way of example, and that MINAZTW and MAXAZTW may take on any desired values. In any case, if the controller 88 determines at step 202 that any of these conditions is met, execution of the routine advances to step 204 where the controller 88 is operable to determine whether an auto-zero (AZ) timer should be reset. If, on the other hand, the controller 88 determines at step 202 that none of the foregoing conditions are met, the weight conditions for auto-zeroing are not satisfied and execution of the routine advances to step 254 for execution of a warning algorithm.

Generally, it is not desirable to reset the auto-zero timer and to therefore avoid executing an auto-zeroing process if it appears that CTPW has not shifted recently. In one embodiment of step 204, if the current state of the auto-zero timer indicates that sufficient time, e.g., 700 ms, has elapsed since the last time an auto-zero was considered, if the bed 50 has not been articulated within a sufficient time period, e.g., 1 second, and if CTPW has been stable within a specified weight window, e.g., +/−2.5 lbs., for a specified time period, e.g., 1 second, the auto-zero timer is reset. If all of these conditions are not satisfied in this exemplary embodiment, execution of the routine advances to step 254 for execution of a warning algorithm. If, however, all of these conditions are satisfied in the exemplary embodiment of step 204, execution of the routine advances to step 206 where the controller 88 resets the auto-zero timer.

Following step 206, the controller 88 is operable at step 208 to determine whether an auto-zero has not occurred since the last patient exit from the bed 50, whether the corrected total patient weight, CTPW, is less by a pound than the last auto-zero weight, LAZW, and whether the change in the absolute sum of LF and RF since the bed 50 was last zeroed by the user is greater than a head angle threshold value, HATH. Generally, the angle of the head section 60e of the mattress relative to horizontal will affect the weight distribution among the load cells 68a-68d. It is accordingly desirable to account for the possibility that that head 60e of the mattress 60 may positioned at some angle other than what is was the last time a bed weight zeroing process was executed. In the illustrated embodiment, a change of the angle of the head section 60e of the mattress 60 from zero to maximum head section elevation, e.g., 65 degrees, may significantly change the distribution of weight between the head end load cells 68a and 68b and the foot end load cells 68c and 68. This can be detected by monitoring a change in the absolute value of the weight impressed upon the foot end load cells 68c and 68d. In this embodiment, the head angle threshold value, HATH, is chosen to be slightly less than one-half of this value, e.g., 8 lbs., since the head section 60e may have been at an elevated position during the last bed zeroing process. In any case, if none of the conditions of step 208 are satisfied, it is unlikely that the head section 60e of the mattress 60 has moved since the last bed zeroing event, and execution of the routine advances to step 254 for execution a warning algorithm. If, however, the controller 88 determines that any of the conditions of step 208 are satisfied, it is likely that the head section 60e of the mattress 60 has moved since the last bed zeroing event and steps 210-224 are then executed to determine an appropriate head angle weight compensation value.

At step 210, the controller 88 tests the change in the absolute sum of LF and RF against the head angle threshold value, HATH, to determine if the head angle has increased since the last bed zeroing event. If the change in the absolute sum of LF and RF exceeds HATH, the head angle has increased since the last bed zeroing event and execution of the routine advances to step 212 where the controller 88 is operable to determine whether the difference in the absolute sum of LF and RF is between the head angle threshold value, HATH, e.g., 8 lbs., and a higher head angle threshold, HHATH, e.g., 12 lbs. If so, a dynamic compensation weight, DCW, which will be added to the bed zero weight at the end of the auto-zeroing process, is assigned a first weight value, W1, e.g., 2 lbs., at step 214. If not, the dynamic compensation weight, DCW, is assigned a second greater weight value, W2, e.g., 3 lbs., at step 216.

If, at step 210, the controller 88 determines that a change in the absolute sum of LF and RF is not greater than HATH, execution of the routine advances to step 218 where the controller 88 tests the change in the absolute sum of LF and RF against the negative of the head angle threshold value, HATH, to determine if the head angle has decreased since the last bed zeroing event. If the change in the absolute sum of LF and RF is less than −HATH, the head angle has decreased since the last bed zeroing event and execution of the routine advances to step 220 where the controller 88 is operable to determine whether the difference in the absolute sum of LF and RF is between the negative head angle threshold value, −HATH, e.g., −8 lbs., and a lower head angle threshold, −LHATH, e.g., −12 lbs. If so, a dynamic compensation weight, DCW, which will be added to the bed zero weight at the end of the auto-zeroing process, is assigned a negative first weight value, −W1, e.g., −2 lbs., at step 222. If not, the dynamic compensation weight, DCW, is assigned a second lesser negative weight value, −W2, e.g., −3 lbs., at step 224. It will be understood that while numerical values are given above for parameters such as HATH, HHATH, LHATH, W1 and W2, such numerical values are provided only by way of example and each of these parameters may alternatively be assigned different values.

Execution of the PM Off State algorithm advances from steps 214, 216, 222 and 224, as well as from the "NO" branch of step 218, to step 226 where the controller 88 is operable to determine the absolute weight on each of the load cells 68a-68d, resulting in the absolute weight values ALH, ALF, ARH and ARF. In the illustrated embodiment, the ALH, ALF, ARH and ARF values are determined from values obtained during the state machine preparation routine of FIG. 6, although these values may be updated at step 226 by taking new weight measurements. In any case, the controller 88 is operable following step 226 at step 228 to determine whether a first auto-zero attempt flag, FAZA, is "false." If not, this is the first execution of step 228 and a set of last auto-zero weight variables may not be updated. Execution of the routine accordingly advances from the "NO" branch of step 228 to step 230 where the controller updates the last auto-zero weight variables with the current absolute weight values by setting LAZLH=ALH, LAZLF=ALF, LAZRH=RH and LAZRF=ARF. The controller 88 is also operable at step 230 to set FAZA="false" so that the next execution of step 228 results in the routine advancing to step 232. Execution of the routine advances from step 230 to step 254 for execution of a warning algorithm.

At step 232, the controller 88 is operable to set current auto-zero weight values to the last auto-zero weight values by setting AZLH=LAZLH, AZLF=LAZLF, AZRH=LAZRH and AZRF=LAZRF. Thereafter at step 233, the controller 88 is operable to again update the last auto-zero weight variables with the current absolute weight values by setting LAZLH=ALH, LAZLF=ALF, LAZRH=RH and LAZRF=ARF. Thereafter at step 234, the controller 88 is operable to determine whether a constant head angle correction factor flag, CHACF, is "true." If so, this indicates that a significant positive shift exists between the head end load cells 68a-68b and the foot end load cells 68c-68d, and that the sum of LH and RH are thus greater than their bed flat values. The constant head angle correction flag, CHACF, is reset ("false") when a significant positive shift exists between the foot end load cells 68c-68d and the head end load cells 68a-68b, and the sum of LF and RF are thus greater than their bed flat values. In any case, execution of the routine advances from the "YES" branch of step 234 to step 236 where the current auto-zero weight values, AZLH, AZLF, AZRH and AZRF, are computed each as a sum of its current value, a constant head angle factor, CHAF, and the dynamic head angle factor, DCW. The constant head angle factor, CHAF, is a constant weight value indicative of added bed weight due to raising of the head section 60e of the mattress 60, and an example value may be 5.0 lbs., although it will be understood that other values may be used. Following step 236, execution of the routine advances to step 237 where the controller 88 is operable to determine whether the dynamic head angle factor, DHAF, is greater than a minimum dynamic head angle factor, MDHAF, e.g., 5. If so, the controller 88 is operable thereafter at step 239 to set the constant head angle correction flag, CHACF, to "false." From step 239, and from the "NO" branch of step 237, execution of the routine advances to step 254 for execution of a warning algorithm.

If, at step 234, the constant head angle correction flag, CHACF, is "false, a significant positive shift does not exist between the head end load cells 68a-68b and the foot end load cells 68c-68d, and execution of the routine advances to step 238 where the controller 88 is operable to compute a dynamic head angle factor, DHAF, as a function of auto-zero weights, AZW, and bed flat zero weights, BFZW. In one embodiment, DHAF=[(AZLF−BFLF)+(AZRF−BFRF)−(AZRH−BFRH)−(AZLH−BFLH)]/4, where BFLH, BFLF, BFRH and BFRF correspond to bed flat LH, LF, RH and RF values determined during a bed flat zero request as will be described hereinafter with respect to FIG. 8. In any case, execution of the routine advances from step 238 to step 240 where the controller 88 is operable to compare the dynamic head angle factor, DHAF, to the sum of a maximum dynamic head angle factor value, MAXDHAF, and the current value of the dynamic compensation weight, DCW. If the controller 88 determines at step 240 that DHAF>MAXDHAF+DCW, execution of the routine advances to step 242 where the controller is operable to clamp the value of the dynamic head angle factor, DHAF, to MAXDHAF+DCW. In one embodiment, MAXDHAF is chosen to correspond to a maximum of 45 degree head section angle relative to horizontal.

If, at step 240 the controller 88 determines that DHAF is not greater than MAXDHAF+DCW, execution of the routine advances to step 244 where the controller 88 is operable to determine whether the dynamic head angle factor, DHAF, is less than an unsafe maximum dynamic head angle factor, USMAXDHAF. If so, the controller 88 is operable thereafter at step 246 to set the constant head angle correction flag, CHACF, to "true." If not, the controller 88 is operable at steps 248 and 250 to clamp DHAF at zero if DHAF is less than zero.

Execution of the PM Off State routine advances from steps 246 and 250, and from the "NO" branch of step 248, to step 252 where the controller 88 is operable to update current values of the auto-zero weights, AZLH, AZLF, AZRH and AZRF, each as a sum of corresponding ones of the individual original zero weights, OZLH, OZLF, OZRH and OZRF, and the dynamic head angle factor, DHAF. Following step 252, the controller 88 is operable at step 254 to execute a warning algorithm by comparing a difference between a common zero total weight, CZTW, and the corrected total patient weight, CTPW, to a first weight value, and to compare an absolute difference between the corrected total patient weight, CTPW, and the frame weight, FW, i.e., the weight of the mattress support frame 58 (see FIG. 9), to a second weight value, W2. If, at step 254 the controller determines that (CZTW−CTPW)>W1 AND abs(CTPW−FW)>W2, the controller 88 activates a warning mechanism, e.g., visual or audible alarm, at step 256 and thereafter at step 258 goes to the Freeze State 126 of the state machine 120 until the warning condition is addressed. Alternatively, the controller 88 may wait or delay for some timer period before activating the warning mechanism at step 256. In any case, if both of these conditions are not met at step 254, execution of the PM Off State routine advances to the return step 260. In one embodiment, W1=4.5 lbs., W2=19 lbs., although other values may be used. The warning algorithm of step 254 is intended to detect removal of the mattress 60, as it activates a warning only if the corrected total patient weight, CTPW, has decreased by at least 4.5 lbs. and the difference between CTPW and FW is more than 19 lbs. (the mattress may add at least 25 lbs. to the frame weight).

Figure 8:
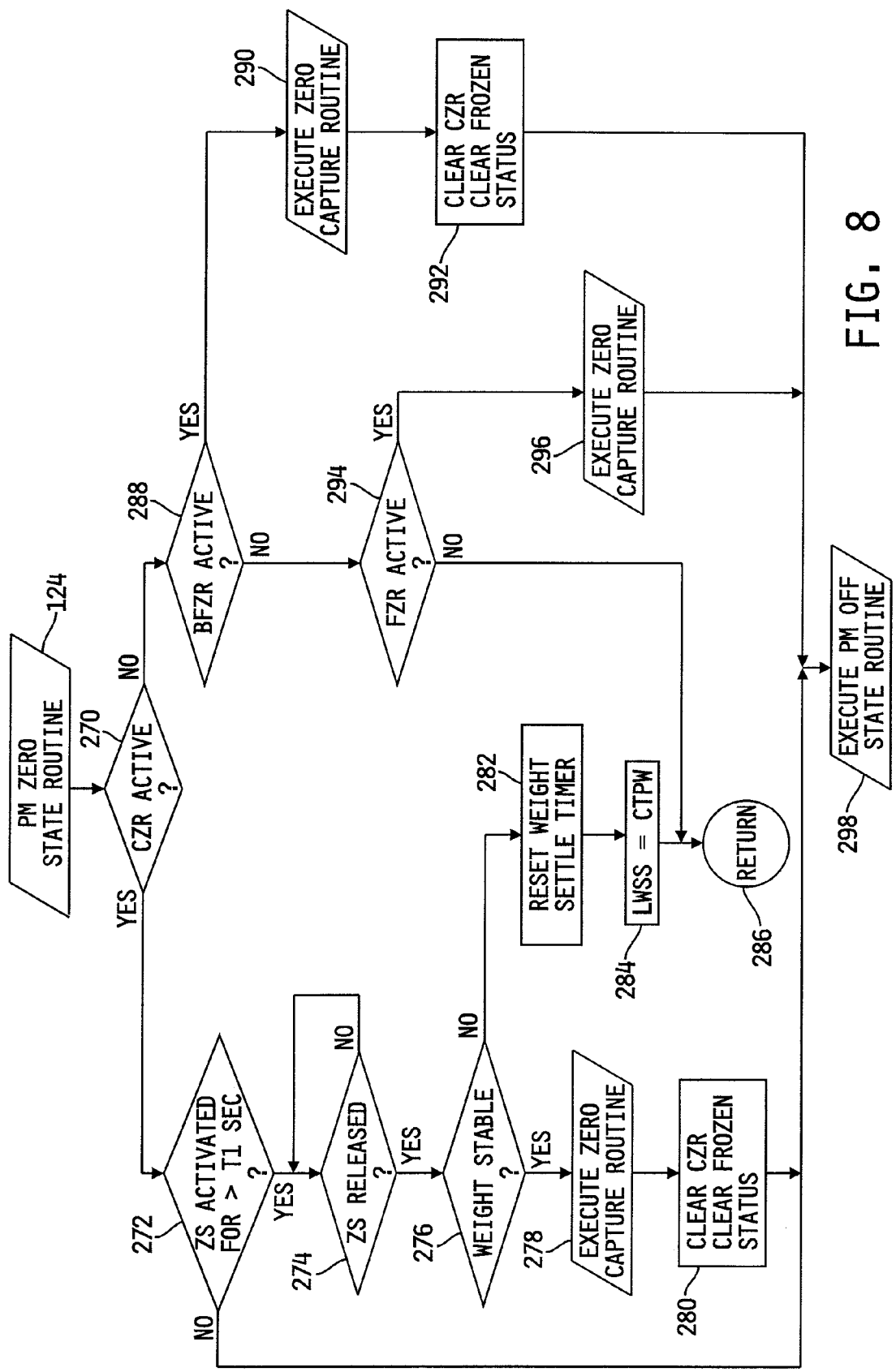
FIG. 8 is a flowchart illustrating an exemplary embodiment of a software routine for executing the PM Zero State that forms part of the state machine of FIG. 5.

Referring now to FIG. 8, a flowchart is shown illustrating an exemplary embodiment of a software routine for executing the PM Zero State 124 of the state machine 120 of FIG. 5. The PM Zero State routine begins at step 270 where the controller 88 is operable to determine whether the routine was called pursuant to a common zero request, CZR. A common zero request, CZR, is made manually via pressing a specified combination of the switches forming part of the control panel 70 (FIG. 2). In one embodiment, for example, a common zero request is made by pressing the enable switch 74 for at least 0.5 seconds and then releasing the enable switch 74, followed by pressing the zero select switch 72 for at least 0.5 seconds. It will be appreciated that other combinations of switches and switch activation scenarios may be used to activate a common zero request, and any such other switch combinations and/or switch activation scenarios are intended to fall within the scope of the appended claims. For example, the zero switch hold time may be a function of the corrected total patient weight, CTPW, slow running average, SRA, or fast running average, FRA, such that the time required for the zero select switch 72 to be pressed in order to complete a common zero request is a function of patient weight. In one embodiment, the zero switch hold time may be directly proportional to patient weight so that longer zero switch hold times are required as patient weight increases, although other functional relationships between the zero switch hold time and the patient weight may be used.

If, at step 270, the controller 88 determines that a common zero request, CZR, is active, execution of the routine advances to steps 272 and 274 where the controller 88 is operable to verify that the zero switch 72 was activated for T1 seconds, e.g., T1=0.5 seconds, and thereafter released. If so, the controller 88 is operable at step 276 to determine whether the weight impressed upon the load cells 68a-68d is stable using one or more of the techniques described hereinabove with respect to the PM Off State. If the controller 88 determines at step 276 that the weight is not stable, the controller 88 is thereafter operable at steps 282 and 284 to reset the weight stable timer and set the last weight settling snapshot, LWSS, equal to the corrected total patient weight, CTPW. Execution of the PM Zero State routine advances from step 284 to a return step 286.

If, at step 276 the controller 88 determines that the weight has been stable for a specified time period, execution of the routine advances to step 278 where the controller 88 executes a zero capture routine. An exemplary embodiment of the zero capture routine will be described below with respect to FIG. 9. Following execution of the zero capture routine at step 278, the controller 88 is operable to clear the common zero request, CZR, and clear any frozen status in case the PM Zero State routine was called when the state machine 120 was in the Freeze State 126.

If, at step 270, the controller 88 determines that a common zero request, CZR, is not active, execution of the PM Zero State routine advances to step 288 to determine whether a bed flat zero request, BFZR, is active. A bed flat zero request, BFZR, is made manually via pressing a specified combination of the switches forming part of the control panel 70. In one embodiment, for example, a bed flat zero request, BFZR, is made by pressing the volume switch 76 for at least 3.0 seconds, followed by pressing the OOB mode switch 84, and then releasing either the OOB mode switch 84 or the volume switch 76 if that is also pressed. It will be appreciated that other combinations of switches and switch activation scenarios may be used to activate a bed flat zero request, and any such other switch combinations and/or switch activation scenarios are intended to fall within the scope of the appended claims.

If, at step 288, the controller 88 determines that a bed flat zero request, BFZR, is active, execution of the routine advances to step 290 where the controller 88 executes the zero capture routine, an exemplary embodiment of which will be described below with respect to FIG. 9. Following execution of the zero capture routine at step 290, the controller 88 is operable at step 292 to clear the bed flat zero request, BFZR, and clear any frozen status in case the PM Zero State routine was called when the state machine 120 was in the Freeze State 126.

If, at step 288, the controller 88 determines that a bed flat zero request, BFZR, is not active, execution of the PM Zero State routine advances to step 294 to determine whether a frame zero request, FZR, is active. A frame zero request, FZR, is made manually via pressing a specified combination of the switches forming part of the control panel 70. In one embodiment, for example, a frame zero request, FZR, is made by pressing the volume switch 76 for at least 3.0 seconds, followed by pressing the Exit mode switch 82 for at least 10.0 seconds, and then releasing either the Exit mode switch 82 or the volume switch 76 if that is also pressed. It will be appreciated that other combinations of switches and switch activation scenarios may be used to activate a frame zero request, and any such other switch combinations and/or switch activation scenarios are intended to fall within the scope of the appended claims.

If, at step 294, the controller 88 determines that a frame zero request, FZR, is active, execution of the routine advances to step 296 where the controller 88 executes the zero capture routine, an exemplary embodiment of which will be described below with respect to FIG. 9. It will be understood that since the zero capture routine is executed at step 296 for the purpose of obtaining a frame zero weight, the mattress 60 will naturally be removed from the mattress support frame 58 prior to step 296. Thereafter, the mattress 60 may be returned to the mattress support frame 58. If, at step 294, the controller 88 determines that the frame zero mode, FZR, is not active, execution of the routine advances to the return step 286. Following steps 280, 292 and 296, as well as the "NO" branch of step 272, execution of the PM Zero State routine advances to step 298 where the state machine 120 advances to the PM Off State 122, and controller 88 is thus operable to execute the PM Off State routine of FIGS. 7A-7C.

Figure 9:
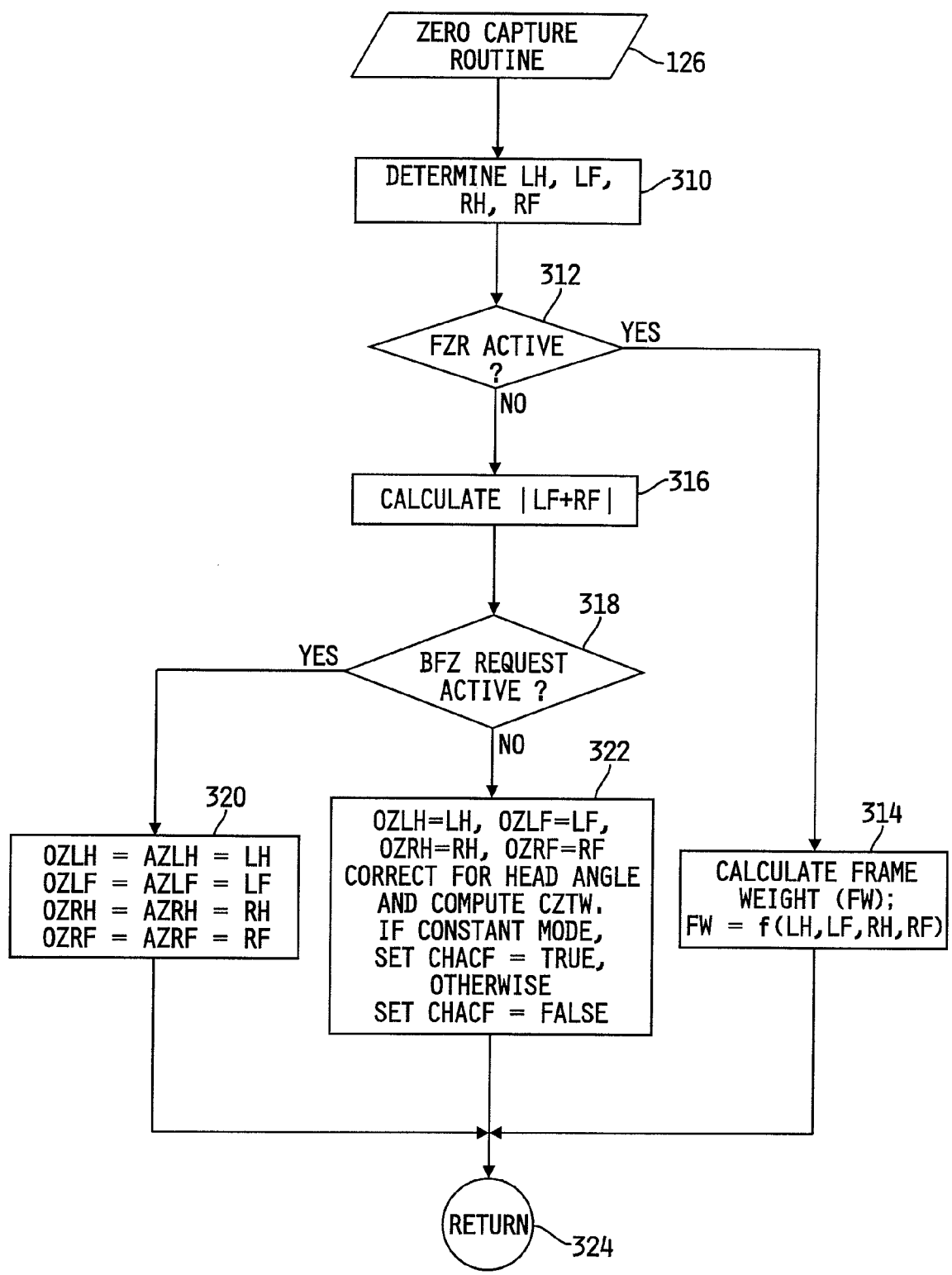
FIG. 9 is a flowchart illustrating an exemplary embodiment of the zero capture software routine called by the PM Zero State routine of FIG. 8.

Referring now to FIG. 9, a flowchart is shown illustrating an exemplary embodiment of the zero capture software routine called at steps 278, 290 and 296 of the PM Zero State routine of FIG. 8. The zero capture routine begins at step 310 where the controller 88 is operable to determine current load cell weight values, LH, LF, RH and RF. Thereafter at step 312, the controller 88 is operable to determine whether a frame zero request, FZR, is active. If so, execution of the routine advances to step 314 where the controller 88 is operable to calculate the frame weight, FW, as a known function of LH, LF, RH and RF. If, at step 312, the controller 88 determines that a Frame zero request, FZR, is not active execution of the routine advances to step 316 where the controller 88 is operable to calculate an absolute value of the sum of LF and RF. Thereafter at step 318, the controller 88 is operable to determine whether a bed flat zero (BFZ) request is active. If so, execution of the routine advances to step 320 where the controller 88 is operable to set original zero (OZ) values and auto zero (AZ) values for each of the load cells 68a-68d to current values of LH, LF, RH and RF, e.g., OZLH=AZLH=LH, OZLF=AZLF=LF, OZRH=AZRH=RH and OZRF=AZRF=RF. If, at step 318, the controller 88 determines that a bed flat zero (BFZ) request is not active, a common zero request must be active and execution of the routine advances to step 322 where the controller 88 is operable to set original zero (OZ) values for each of the load cells 68a-68d to current values of LH, LF, RH and RF, e.g., OZLH=LH, OZLF=LF, OZRH=RH and OZRF=RF, and correct these original zero values for head angle as described hereinabove with respect to the auto-zeroing portion of the PM Off State routine of FIGS. 7A-7C. If the head angle correction was dynamic and is entering the constant mode, set the constant head angle correction flag, CHACF, to "true". If, on the other hand, the head angle correction was constant and is entering the dynamic mode, set CHACF to "false." In either case, the controller is also at step 322 to compute a common zero total weight, CZTW, as described hereinabove with respect to the auto-zeroing portion of the PM Off State routine of FIGS. 7A-7C. Following any of the steps 314, 320 and 322, execution of the routine advances to step 324 where the zero capture routine is returned to its calling routine.

Referring now to FIGS. 10A-10B, a flowchart is shown of one illustrative embodiment of a software algorithm or routine for executing the PM Movement/Exit Transition State 128 of the state machine 120. The PM Movement/Exit Transition State routine begins at step 350 where the controller 88 is operable to determine whether the current execution of step 350 constitutes the first execution of the PM Movement/Exit Transition routine. If so, execution of the routine advances to step 352 where the controller 88 is operable to reset a general active (GA) timer. Execution of the routine advances from step 352, and from the "NO" branch of step 350, to step 354 where the controller 88 is operable to determine whether the GA timer is less than a settling time, $T_S$. If so, execution of the routine advances to step 356 where the controller 88 is operable to set the last weight settling snapshot, LWSS, equal to the corrected total patient weight, CTPW. Steps 354 and 356 allow $T_S$ seconds between capturing of new load cell data before the weight stability check will continue. In one embodiment, $T_S$=140 ms, although $T_S$ may alternatively be set at other desired values.

Execution of the PM Movement/Exit Transition State routine advances from step 356, and from the "NO" branch of step 354, to step 358 where the controller 88 is operable to compare the corrected total patient weight, CTPW, to a sum of, and a difference between, the last weight settling snapshot, LWSS, and an arming weight settle constant, AWSC. In the illustrated embodiment, if the controller 88 determines at step 358 that CTPW>LWSS+AWSC AND CTPW<LWSS− AWSC, this is an indication that the weight on the mattress 60 is unstable and execution of the routine advances to step 360 where the controller 88 is operable to set LWSS equal to CTPW and to reset the weight stable timer.

Execution of the PM Movement/Exit Transition State routine advances from step 360, and from the "NO" branch of step 358, to step 362 where the controller 88 is operable to execute the exit mode routine to determine whether the patient is within the safe arming zone of the mattress 60. Thereafter at step 364, the controller 88 is operable to determine whether the patient exit (PE) or patient movement (PM) mode switch enable time is satisfied. In one embodiment of the system 75, the mode switches 80-84 must be depressed for at least a selected time period, e.g., 0.5 seconds, and then released to successively activate a patient monitoring mode. It will be appreciated that combinations of switches and/or different switch activation scenarios may be used to activate the various patient monitoring modes, and any such other switch combinations and/or switch activation scenarios are intended to fall within the scope of the appended claims.

In any case, if the controller 88 determines at step 364 that either of the patient exit (PE) or patient movement (PM) modes have been successfully selected, execution of the routine advances to step 366. If not, the selected switch has not been depressed long enough before release and execution of the routine thus advances to step 376 where the controller 88 is operable to make this determination. If, at step 376, the controller 88 determines that the selected mode switch has been released before successfully selecting the patient exit (PE) mode or the patient movement (PM) mode, then the selected mode was not successively activated and execution of the routine advances to step 378 where the state machine 120 moves to the PM Off State 122 and the controller 88 is thus operable to execute the PM Off State routine of FIGS. 7A-7C. If the controller 88 determines at step 376 that the selected switch has not been released, then execution of the routine advances to the return step 380.

At step 366, the controller 88 has determined that one of the patient exit (PE) or patient movement (PM) modes have been successfully selected and the controller 88 is operable to determine whether execution of the exit mode routine at step 362 determined that the patient is within the safe arming zone of the mattress 60. If so, the patient exiting zone flag, PEZ, was set equal to "false" by the exit mode algorithm. The controller 88 is further operable at step 366 to determine whether the corrected total patient weight, CTPW, is between a minimum patient weight, MINPW, and a maximum patient weight, MAXPW. In one embodiment, for example, MINPW=50 lbs. and MAXPW=500 lbs., although these values are provided only by way of example and other values of MINPW and MAXPW. For example, MINPW may be set to a value greater than 50 lbs., or may be set to a value less than 50 lbs. to accommodate lighter-weight patients such as toddlers and/or infants. Likewise, MAXPW may be set to a value less than 500 lbs., or may be set to a value greater than 500 lbs. to accommodate bariatric patients. In any case, if the controller 88 determines that all three of the conditions are met, i.e., that the patient is in the safe arming zone of the mattress 60, CTPW>MINPW and CTPW<MAXPW, execution of the routine advances to step 368 where the controller 88 is operable to compare the weight settling timer to a predefined settling time, $T_{ST}$, e.g., 5 seconds.

If the weight settling timer is greater than $T_{ST}$, indicating that the weight has been stable for at least $T_{ST}$, execution of the routine advances to step 370 where the controller 88 is operable to set a last armed weight, LAW, and an armed weight, AW, equal to the total patient weight slow running average, SRA, to set the acquire new arming weight request flag, ANAWR, to "false", to reset the weight settling (WS) timer, to set a waiting for weight settling flag, WFWS, to "true", to capture new reference load cell values, RLH, RLF, RRH and RRF, and compute a new corrected total patient weight, CTPW, from RLH, RLF, RRH and RRF as described hereinabove, to set the last weight settling snapshot, LWSS, to the new corrected total patient weight, CTPW, and to reset an active state timer. If, at step 368 the controller 88 determines that the weight has not been stable for at least $T_{ST}$, execution of the routine advances to step 372 where the controller 88 is operable to set the last armed weight, LAW, and the armed weight, AW, equal to the total patient weight slow running average, SRA, to set the acquire new arming weight request flag, ANAWR, to "true", to reset the weight settling timer, set a waiting for weight settling flag, WFWS, to "true", to capture new reference load cell values, RLH, RLF, RRH and RRF, and compute a new corrected total patient weight, CTPW, from RLH, RLF, RRH and RRF as described hereinabove, to set the last weight settling snapshot, LWSS, to the new corrected total patient weight, CTPW, and to reset an the active state timer. Alternatively, the controller 88 may be operable at either of steps 370 and 372 to set the last armed weight, LAW, and/or the armed weight, AW, equal to the total patient weight fast running average, FRA, or corrected total patient weight, CTPW. It will be noted that the armed weight, AW, differs from the last armed weight, LAW. The armed weight value, AW, is an armed weight value used by the out-of-bed (OOB) mode routine, as will be described in detail hereinafter with respect to FIG. 19, and may change during execution of the PM Exit/Movement Transition State routine as just described and/or during execution of the PM Active State routine as will be described in detail with respect to FIGS. 11A-11C. The last armed weight value, LAW, on the other hand, changes whenever weight greater than the sensitivity to minimum weight change value, SMWC, or less than −SMWC, is added to the bed 50. In any case, execution of the PM Movement/Exit Transition State routine advances from either of the steps 370 and 372 to step 374 where the state machine 120 moves to the PM Active State 150 and the controller 88 thus executes a PM Active State routine, an example of which will be described with respect to FIGS. 11A-11C.

The PM Movement/Exit Transition State 128 just described is thus operable to ensure that the patient weight is between specified minimum and maximum patient weight values, and to ensure that the patient is within the safe arming zone of the mattress 60, when the patient movement (PM) or patient exit (PE) mode is activated. If these conditions are met and the patient movement (PM) or patient (PE) is successfully activated, the system 75 is armed and the state machine moves to the PM Active State, thereby indicating that one of the patient monitoring modes is currently active with a patient supported by the mattress 60. It should be noted that the arming conditions are not dependent on other bed-related parameters such as head angle or elevation, leg elevation, or the like. In fact, as long as the foregoing arming conditions are met, the PE or PM patient monitoring modes will be enabled regardless of whether the head section of the bed is elevated anywhere between bed flat, i.e., horizontal, and the maximum head elevation angle, e.g., 65 degrees, and/or regardless of whether the leg section is elevated anywhere between its minimum and maximum leg elevation angles. Moreover, when the system is armed as just described pursuant to enablement of either the PE mode or the PM mode, the head section may thereafter be articulated to any elevation between bed flat at the maxim head elevation angle without activating a patient exit alarm or a patient movement alarm. Likewise, the leg section may thereafter be articulated anywhere between its two extreme elevations without triggering a patient exit alarm or patient movement alarm. In an alternate embodiment, it is desirable to distinguish between patient articulation of the head section and/or the leg section after the system is armed. In this embodiment, the system may be configured to allow such head section and/or leg section articulation is executed via the control panel 70, but to activate an alarm if such head section and/or leg section articulation is executed via a patient control pendant.

Figure 11A:
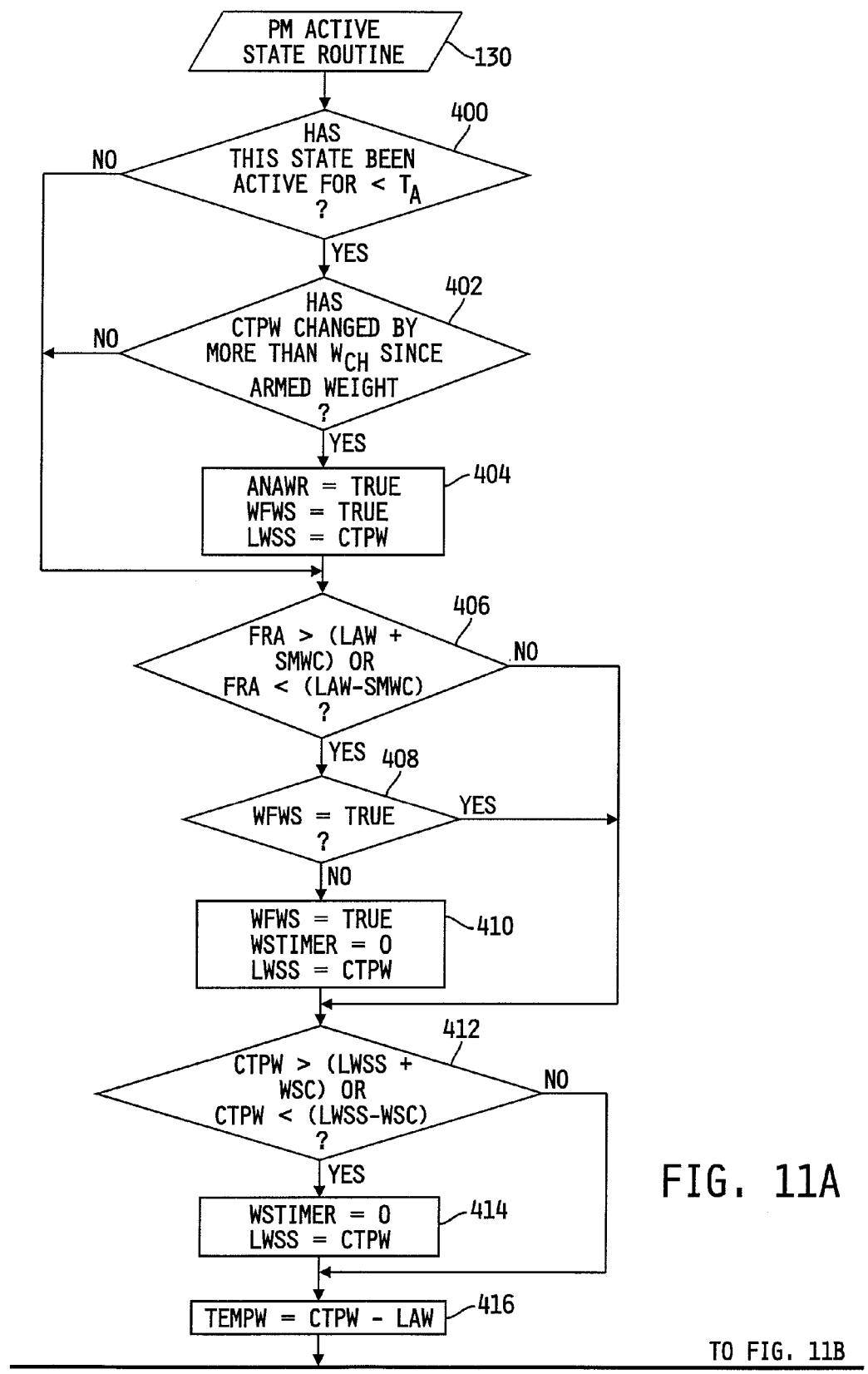
FIGS. 11A-11C show a flowchart illustrating an exemplary embodiment of a software routine for executing the PM Active State that forms part of the state machine of FIG. 5.
Figure 11B:
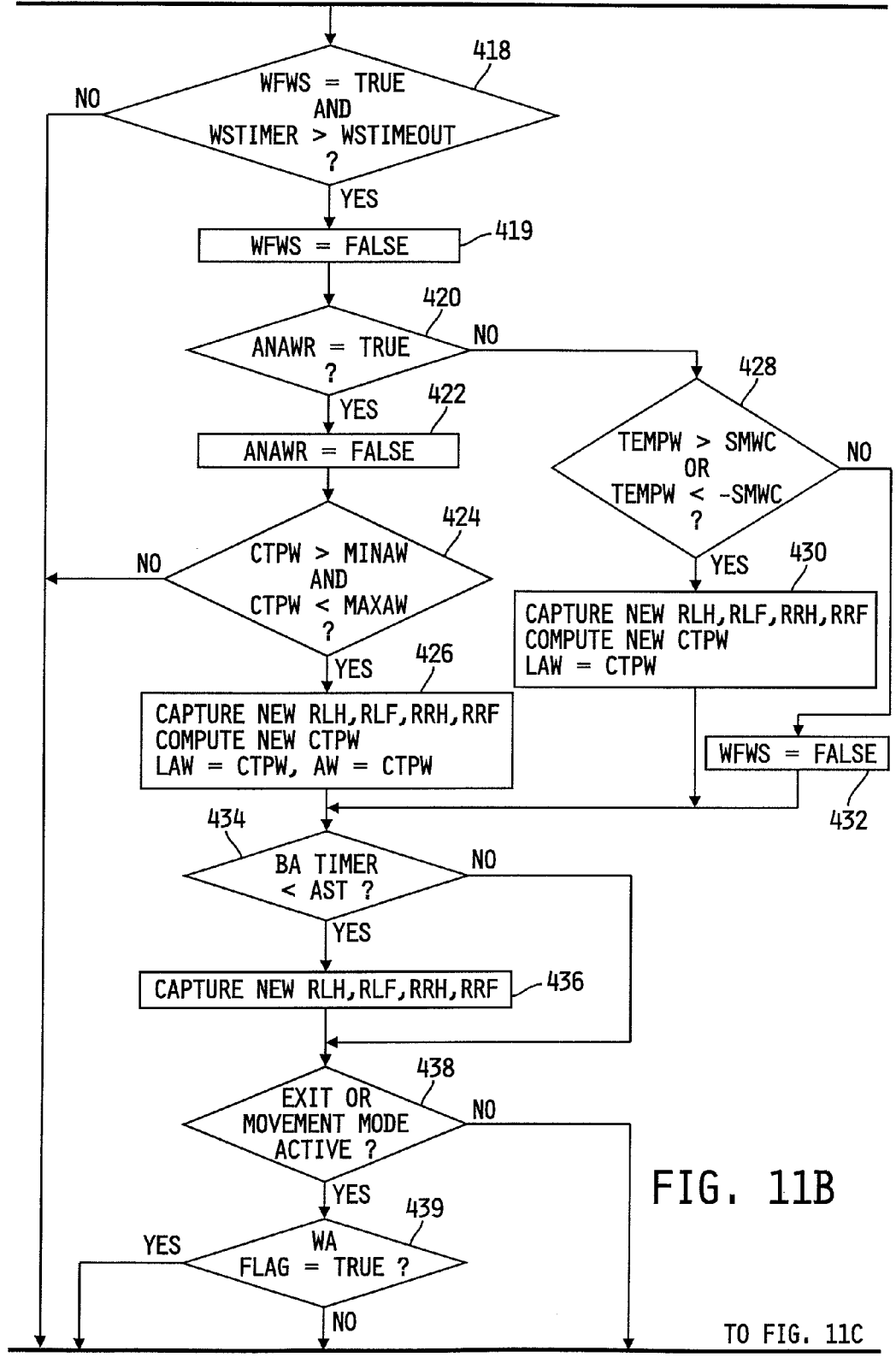
Figure 11C:
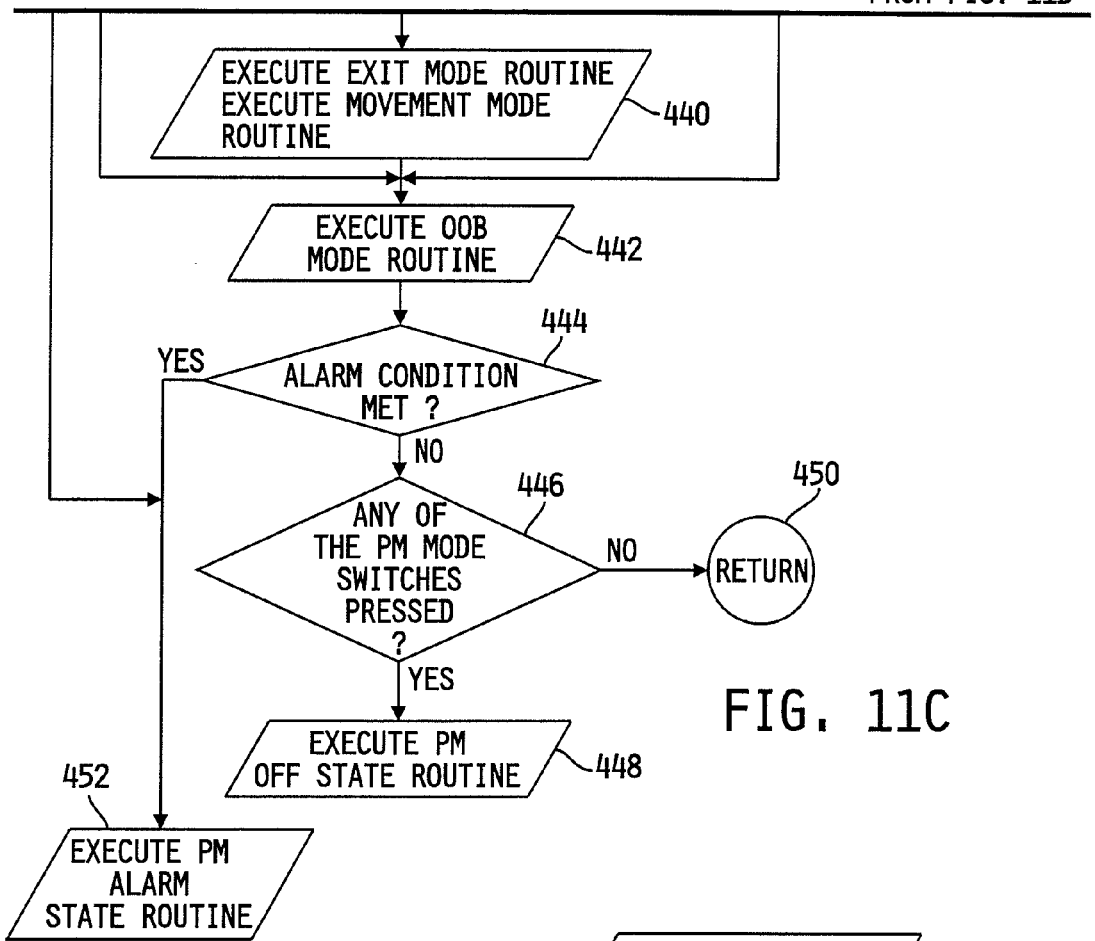

Referring now to FIGS. 11A-11C, a flowchart is shown of one illustrative embodiment of a software algorithm or routine for executing the PM Active State 130 of the state machine 120. The PM Active State routine begins at step 400 where the controller 88 is operable to determine whether the PM Active State has been active for less than an active time, $T_A$, e.g., 3 seconds. If so, execution of the routine advances to step 402 where the controller 88 is operable to determine whether the corrected total patient weight, CTPW, has changed by more than a weight change value, $W_{CH}$, since the armed weight, AW, was established when system 75 was armed pursuant to the PM Movement/Exit Transition State 128 (see FIGS. 10A-10B). The weight change value, $W_{CH}$, is, in one embodiment, set to a weight value above which may be typical of someone leaning against and applying some additional weight to the weigh frame 56 or other structure coupled to the weigh frame 56, e.g., an armrail 66a-66d. In any case, if the controller 88 determines at step 402 that CTPW has changed by more than $W_{CH}$ since the armed weight, AW, was established, execution of the routine advances to step 404 where the controller 88 is operable to set the acquire new armed weight request flag, ANAWR, to "true", to set the waiting for weight settling flag, WFWS, to "true" and to set the last weight settling snapshot, LWSS, equal to the corrected total patient weight, CTPW.

Execution of the PM Active State routine advances from step 404, and from the "NO" branches of steps 400 and 402, to step 406 where the controller 88 is operable to compare the total patient weight fast running average, FRA, to a sum and difference of the last armed weight, LAW, and the sensitivity to minimum weight change value, SMWC, established by the state machine preparation routine of FIG. 6. If the controller 88 determines at step 406 that FRA>(LAW+SMWC) or FRA<(LAW−SMWC), this indicates that the bed weight has increased sufficiently to warrant verification that weight was added to or removed from the weigh frame 56. Thus if the total patient weight fast running average, FRA, exceeds (LAW+SMWC) or falls below (LAW−SMWC), execution of the routine advances to step 414 where the controller 88 is operable to reset the weight settling timer and to set the last weight settling snapshot, LWSS, equal to the current corrected total patient weight, CTPW. Alternatively, the controller 88 may be operable at step 406 to compare the total patient weight slow running average, SRA, or corrected total patient weight, CTPW, to the sum and difference of the last armed weight, LAW, and the sensitivity to minimum weight change value, SMWC.

Execution of the PM Active State routine advances from step 414, and from the "NO" branch of step 412, to step 416 where the controller 88 is operable to compute a temporary weight value, TEMPW as a difference between the corrected total patient weight, CTPW, and the last armed weight, LAW. Thereafter at step 418, the controller 88 is operable to determine whether the bed weight has stabilized by testing the status of the waiting for weight settling flag, WFWS, and the status of the weight settling timer. If, at step 418, the controller 88 determines that WFWS is "true" and the weight settling timer has timed out, execution of the routine advances to step 419 where the controller 88 is operable to set WFWS to "false." Otherwise, execution of the routine advances to step 452 where the state machine 120 moves to the PM Alarm State where the controller 88 is operable to execute a PM Alarm State routine of the type illustrated in FIG. 12

Execution of the PM Active State routine advances from step 419 to step 420 where the controller 88 is operable to determine the status of the acquire new arming weight request flag, ANAWR. If the controller 88 determines at step 420 that ANAWR is "true", execution of the routine advances to steps 422, 424 and 426 where the controller 88 is operable to capture new reference load cell values, compute a new corrected total patient weight, CTPW, and determine a new armed weight. In the illustrated embodiment, the controller 88 is operable to accomplish this by first setting ANAWR to "false" at step 422, and then capturing new reference load cell values, RLH, RLF, RRH and RRF, and computing a new corrected total patient weight, CTPW, from RLH, RLF, RRH and RRF as described hereinabove, and setting the last armed weight, LAW, and the Armed weight, AW, to the current corrected total patient weight, CTPW at step 426, if CTPW is determined at step 424 to be between a minimum armed weight, MINAW, and a maximum armed weight, MAXAW. If the controller 88 determines at step 424 that CTPW is not between MINAW and MAXAW, however, execution of the routine advances to step 452 where the state machine 120 moves to the PM Alarm State where the controller 88 is operable to execute a PM Alarm State routine of the type illustrated in FIG. 12.

If, at step 420, the controller 88 determines that the acquire new armed weight request flag, ANAWR is "false", execution of the routine advances to step 428 where the controller 88 is operable to compare the temporary weight value, TEMPW, determined at step 416 to the sensitivity to minimum weight change value, SMWC. TEMPW represents a difference between the current corrected total patient weight, CTPW, and the last armed weight value, LAW, and if this difference value exceeds SMWC in either direction the controller 88 determines that a sufficient amount of weight has been added to or removed from the weigh frame 56 to require new total patient weight information. Thus, if the controller 88 determines at step 428 that TEMPW>SMWC OR TEMPW<−SMWC, execution of the routine advances to step 430 where the controller 88 is operable to capture new reference load cell values, RLH, RLF, RRH and RRF, to compute a new corrected total patient weight, CTPW, from RLH, RLF, RRH and RRF as described hereinabove, and to set the last armed weight, LAW, equal to the newly computed corrected total patient weight, CTPW. If, on the other hand, the controller 88 determines at step 428 that TEMPW falls between −SMWC and SMWC, this is an indication that the bed weight has stabilized but not enough weight has been added to or removed from the weigh frame 56 to justify calculation of a new corrected total patient weight, CTPW. In this case, execution of the routine thus advances to step 432 where the controller 88 is operable to set the waiting for weight settling flag, WFWS, to "false."

Execution of the PM Active State routine advances from steps 426, 430 and 432 to step 434 where the controller 88 is operable to determine whether a bed articulation timer is less than an articulation stabilized time, AST. If so, the bed 50 is either articulating or has articulated in the last second or so, and the controller 88 is thus operable at step 436 to capture new reference load cell values, RLH, RLF, RRH and RRF.

Execution of the PM Active State routine advances from step 436, and from the "NO" branch of step 434, to step 438 where the controller 88 is operable to determine whether either of the patient exit (PE) and patient movement (PM) modes are currently active. If either of these modes is currently active, execution of the routine advances to step 439 where the controller 88 is operable to determine the status of a weight added flag, WA. If the weight added flag, WA, is "false", execution of the routine advances to step 440 where the controller 88 is operable to execute an exit mode routine and a movement mode routine, examples of which will be described in greater detail hereinafter with respect to FIGS. 13-18. Execution of the routine advances from step 440, and from the "NO" branch of step 439, to step 442 where the controller 88 is operable to execute an out-of-bed (OOB) mode routine, one example of which will be described in greater detail hereinafter with respect to FIG. 19. Thereafter at step 444, the controller 88 is operable to determine whether an alarm condition is met (is active) as a result of execution of either of the exit mode routine, the movement mode routine or the out-of-bed mode routine. If so, execution of the PM Active State routine advances to step 452 where the state machine 120 moves to the PM Alarm State 136. If, at step 444, the controller 88 determines that no alarm conditions are currently active, execution of the routine advances to step 446 where the controller 88 is operable to determine whether any of the PM mode switches 80-84 have been pressed. If not, execution of the routine advances to a return step 450. If, at step 446, the controller 88 determines that at least one of the PM mode switches 80-84 has been pressed, or some other predefined combination of switches has been pressed, execution of the routine advances to step 448 where the state machine 120 moves to the PM Off State, and the controller 88 is operable to execute a PM Off State routine of the type illustrated in FIGS. 7A-7C.

The PM Active State 130 just described is thus operable to monitor addition of weight to, and/or removal of weight from, the weigh frame 56, and to call appropriate ones of the patient monitoring modes. If sufficient weight is added to, or removed from, the weigh frame 56 during the PM Active mode, a new corrected total patient weight is then computed. As will become more apparent hereinafter, the patient exit (PE) and patient movement (PM) modes will continue to monitor patient movement after the system 75 is armed either pursuant to selecting PE mode or PM mode, without activating an alarm if further weight, less than 30 lbs., for example, is added to the bed regardless of the total patient weight on the bed prior to adding the further weight, as long as CTPW is between MINPW and MAXPW. Likewise, the patient exit (PE) and patient movement (PM) modes will continue to monitor patient movement after the system 75 is armed either pursuant to selecting PE mode or PM mode, without activating an alarm if further weight, less than 30 lbs., for example, is added to the bed after determining a bed zero weight, as long as CTPW, determined as a function of the bed zero weight, is between MINPW and MAXPW.

Figure 12:
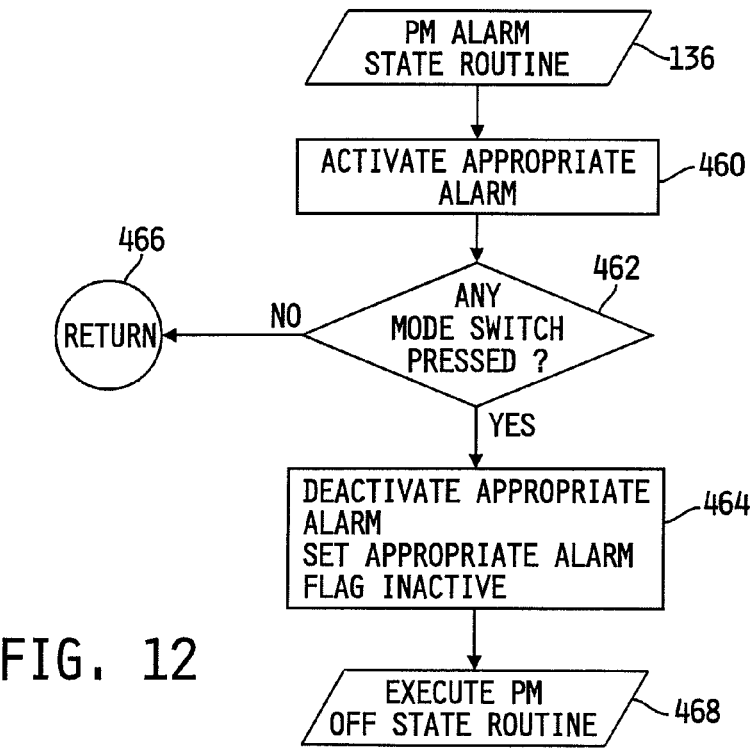
FIG. 12 is a flowchart illustrating an exemplary embodiment of a software routine for executing the PM Active State that forms part of the state machine of FIG. 5.

Referring now to FIG. 12, a flowchart is shown of one illustrative embodiment of a software algorithm or routine for executing the PM Alarm State 136 of the state machine 120. The PM Alarm State routine begins at step 460 where the controller 88 is operable to activate an appropriate alarm. Either one or both of the local alarm 98 and the remote alarm 99 may be flagged for activation, and the controller 88 is accordingly operable at step 460 to activate any alarm or alarms that are currently flagged for activation. Thereafter at step 462, the controller 88 is operable to determine whether any of the patient monitoring mode switches 80-84 have been pressed to thereby deactivate any active alarms. If not, execution of the routine advances to the return step 466. If, however, the controller 88 determines at step 462 that any of the patient monitoring mode switches 80-84 have been flagged for activation, execution of the routine advances to step 464 where the controller 88 is operable to deactivate either, or both, of the alarms 98 and 99, and to set an appropriate one, or both, of the alarms flags to an inactive state. Thereafter at step 468, the state machine 120 moves to the PM Off State, and the controller 88 is operable to execute a PM Off State routine of the type illustrated in FIGS. 7A-7C.

Figure 13:
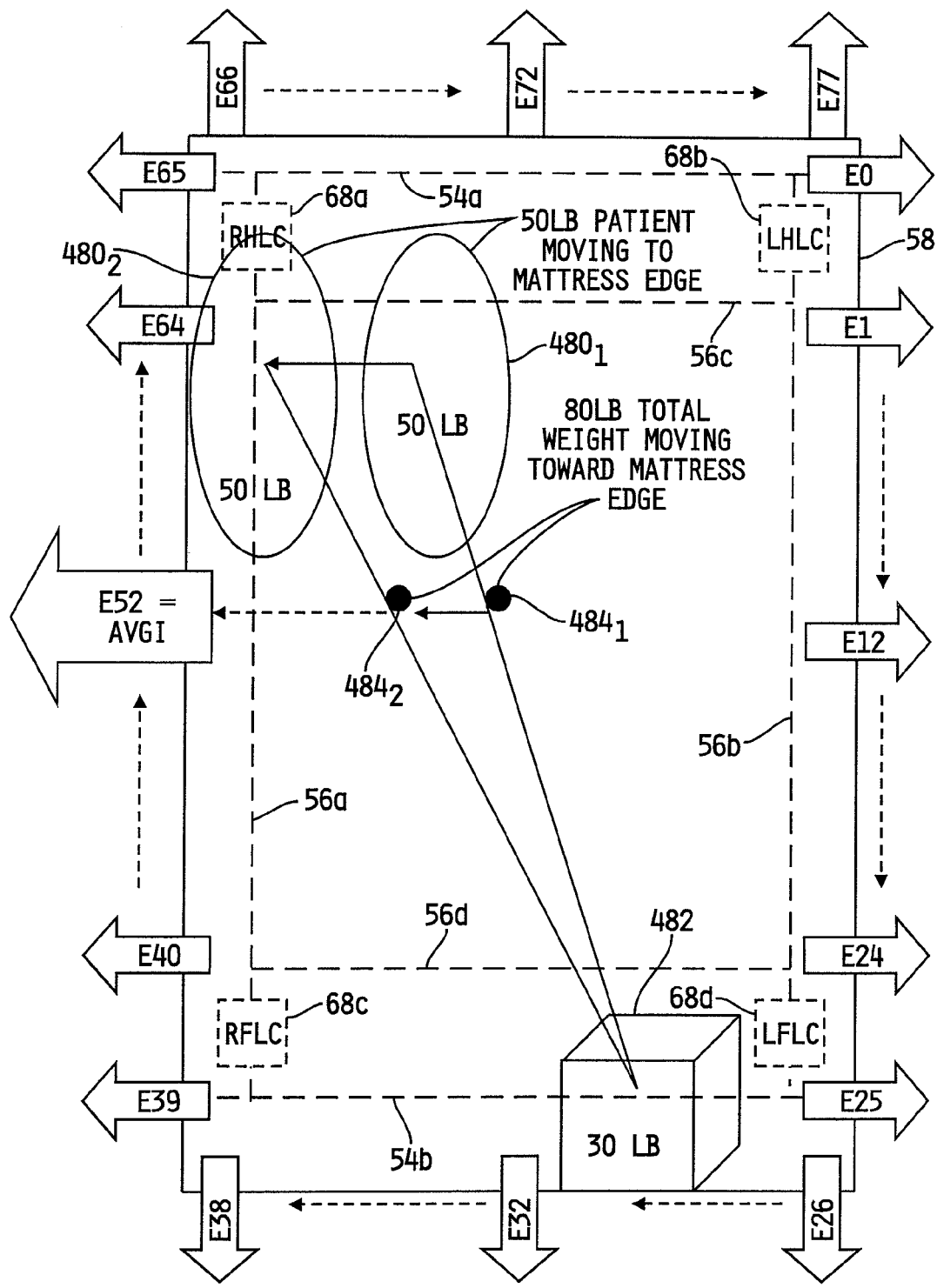
FIG. 13 is a block diagram illustrating one example construction of an exit condition threshold table for use by a patent exit routine called by the PM Active STATE software routine of FIGS. 11A-11C.

In one exemplary embodiment of the system 75, the controller 88 is configured, pursuant to the patient exit (PE) mode of the PM Active State 130, to determine impending exit by the patient from the mattress 60 by comparing the current distribution of the patient's weight over the four load cells 68a-68d to a predefined collection of load cell exit threshold data. In the illustrated embodiment, this predefined collection of load cell exit data is provided in the form of a table of a number of sets of load cell exit threshold values, although the collection of load cell exit data may alternatively be provided in the form of one or more equations, graphs, charts or the like. Referring now to FIG. 13, a diagram of the bed 50 is shown illustrating one example implementation and construction of such a table of load cell exit threshold values. In this example, empirical load cell threshold data is established by discretely moving a predefined calibration weight, e.g., 100 lbs., about a periphery of the mattress 60 or mattress support frame 58 and recording the corresponding readings, LH, LF, RF, RH, of the four load cells 68a-68d into an exit condition threshold table. Each such reading corresponds to a set of exit condition threshold values, LHTN, LFTN, RFTN and RHTN, normalized to the predefined calibration weight, and above which defines an exit condition at the current location for the predefined calibration weight. The exit condition threshold table may be sized to contain any number of sets of exit condition threshold values, wherein the total number of such sets used to populate the table will typically be dependent upon the resolution requirements of the system 75.

In the example illustrated in FIG. 13, the exit condition threshold table is populated with 78 such sets of exit condition threshold values, E0-E77 defined about the periphery of the mattress support frame 58. Each set of normalized exit condition threshold values, LHTN, LFTN, RFTN and RHTN, may be provided in the form of individual weight values, e.g., lbs., percentage of the total weight on each of the load cells 68a-68d, ratios of load cell weights relative to each other or to an armed weight, or the like. The following Table 1 illustrates a portion of an example exit condition threshold table wherein each set of normalized exit condition threshold values, LHTN, LFTN, RFTN and RHTN, is provided in the form of individual weight values. The example exit condition threshold table illustrated in Table 1 is populated with a total of 78 sets of exit condition threshold values (although only 10 such sets are shown) obtained by discretely moving a 100 lb. calibration weight, CW, in approximately equally-spaced location increments along the perimeter of the mattress support frame 58, approximately 2.5 inches from each of the sides and approximately one foot from each of the head and foot ends, and recording the corresponding weight values or weight percentages impressed upon each of the load cells 68a-68d. It will be understood, however, that the data represented in Table 1, along with the particular manner in which it is generated, is provided only by way of example, and that Table 1 may alternatively be generated using other data types, other predefined calibration weight values, other equally-spaced or non-equally-spaced location increments, other spacings between the calibration weight and the sides and/or ends of the mattress support frame 58, and/or different total number of sets of exit condition threshold values. Any such alternate implementation of the exit condition threshold table, graph, chart or one or more mathematical equations, is contemplated by this disclosure.

TABLE 1

| Exit Location | LHTN (lbs.) | LFTN (lbs.) | RFTN (lbs.) | RHTN (lbs.) |
|---|---|---|---|---|
| E0 | 92 | 15 | −48 | 41 |
| E1 | 88 | 19 | −44 | 37 |
| E2 | 84 | 24 | −40 | 33 |
| E3 | 79 | 29 | −36 | 29 |
| E4 | 75 | 33 | −32 | 24 |
| E5 | 71 | 38 | −28 | 20 |
| E6 | 66 | 42 | −24 | 17 |
| E7 | 62 | 46 | −20 | 13 |
| . | . | . | . | . |
| . | . | . | . | . |
| . | . | . | . | . |
| E76 | 83 | 54 | −41 | 10 |
| E77 | 87 | 59 | −45 | 5 |

Figure 14A:
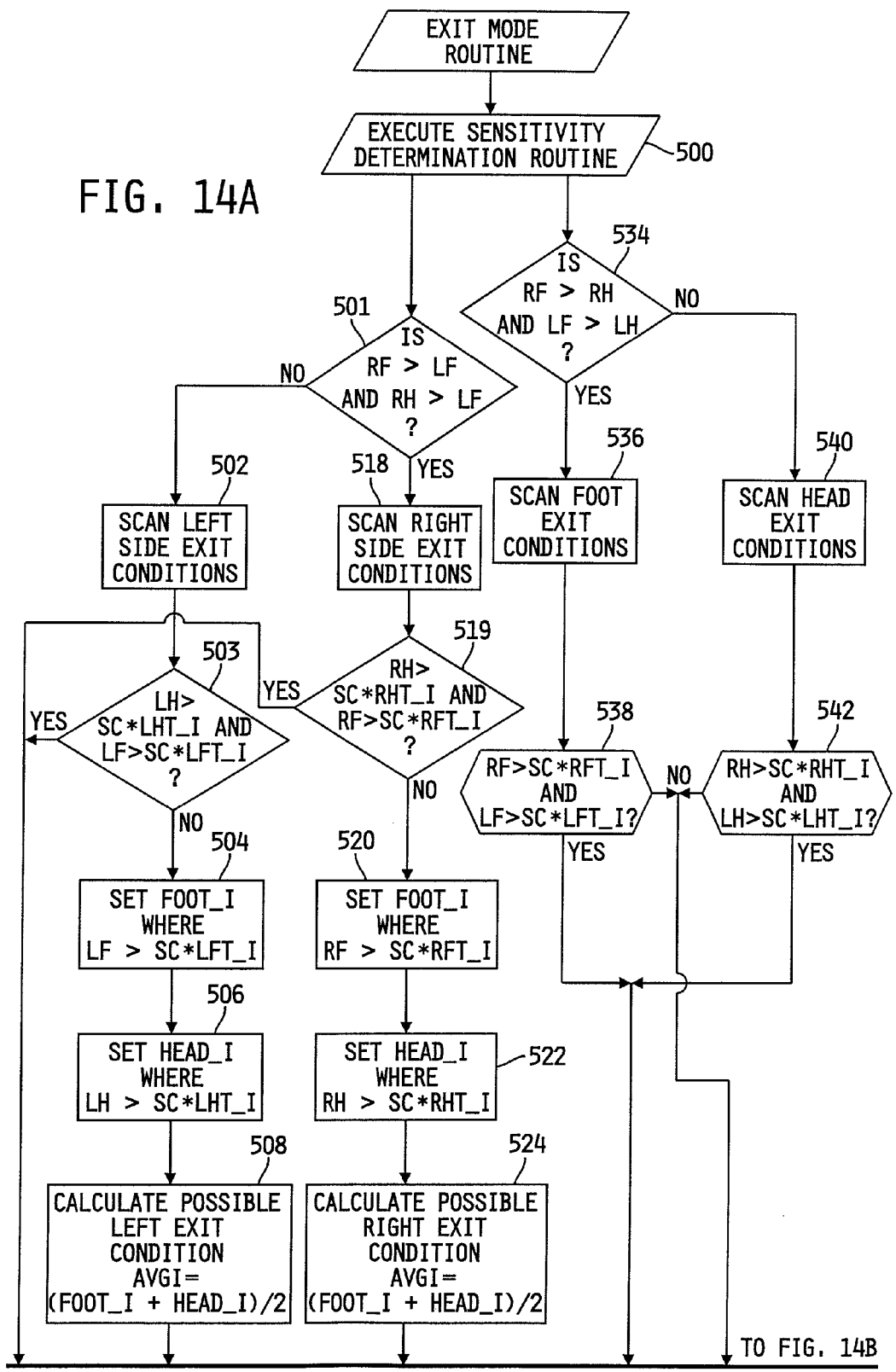
FIGS. 14A-14C show a flowchart illustrating an exemplary embodiment of the exit mode routine called by the PM Active State software routine of FIGS. 11A-11C.
Figure 14B:
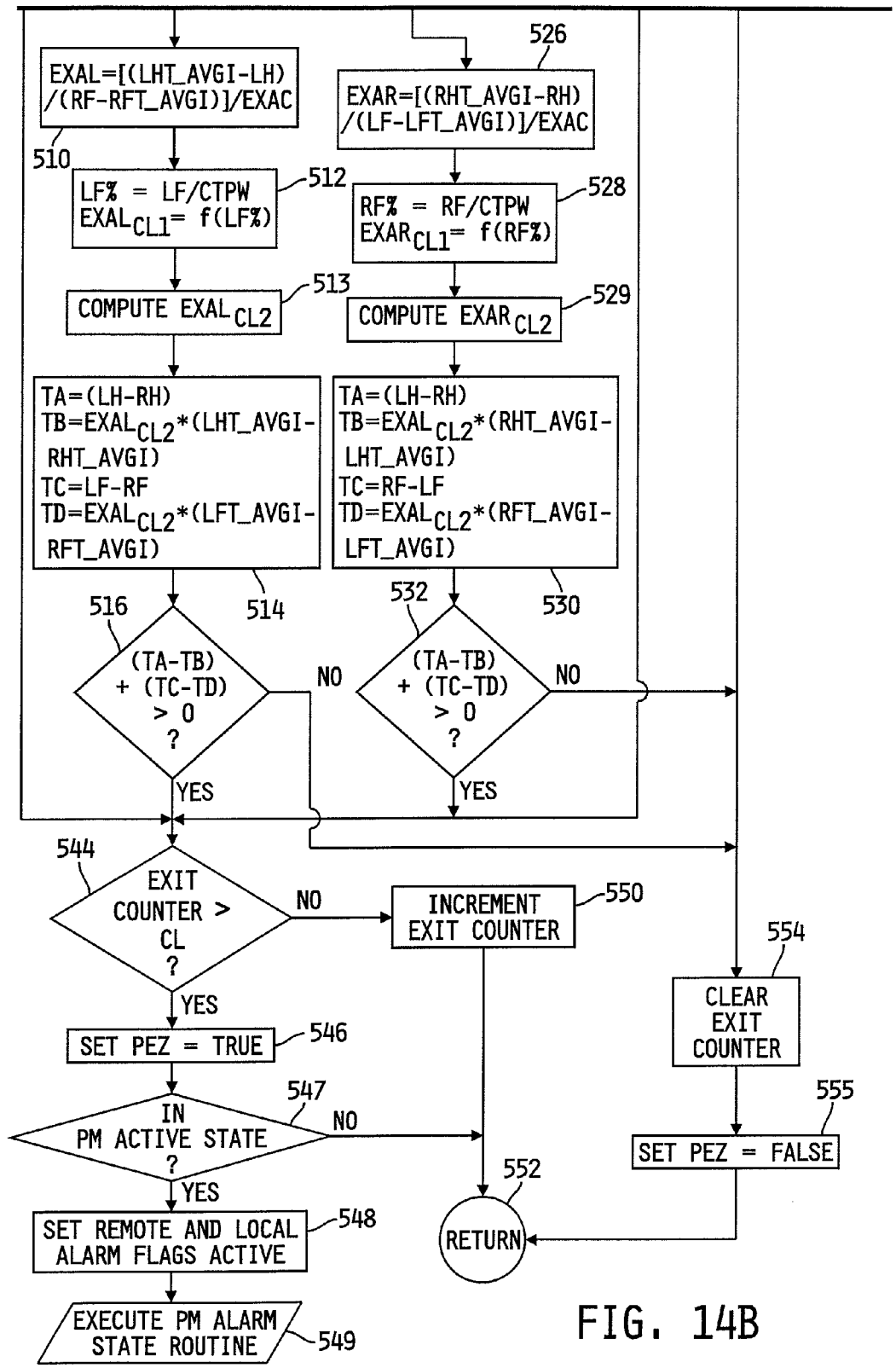
Figure 14C:
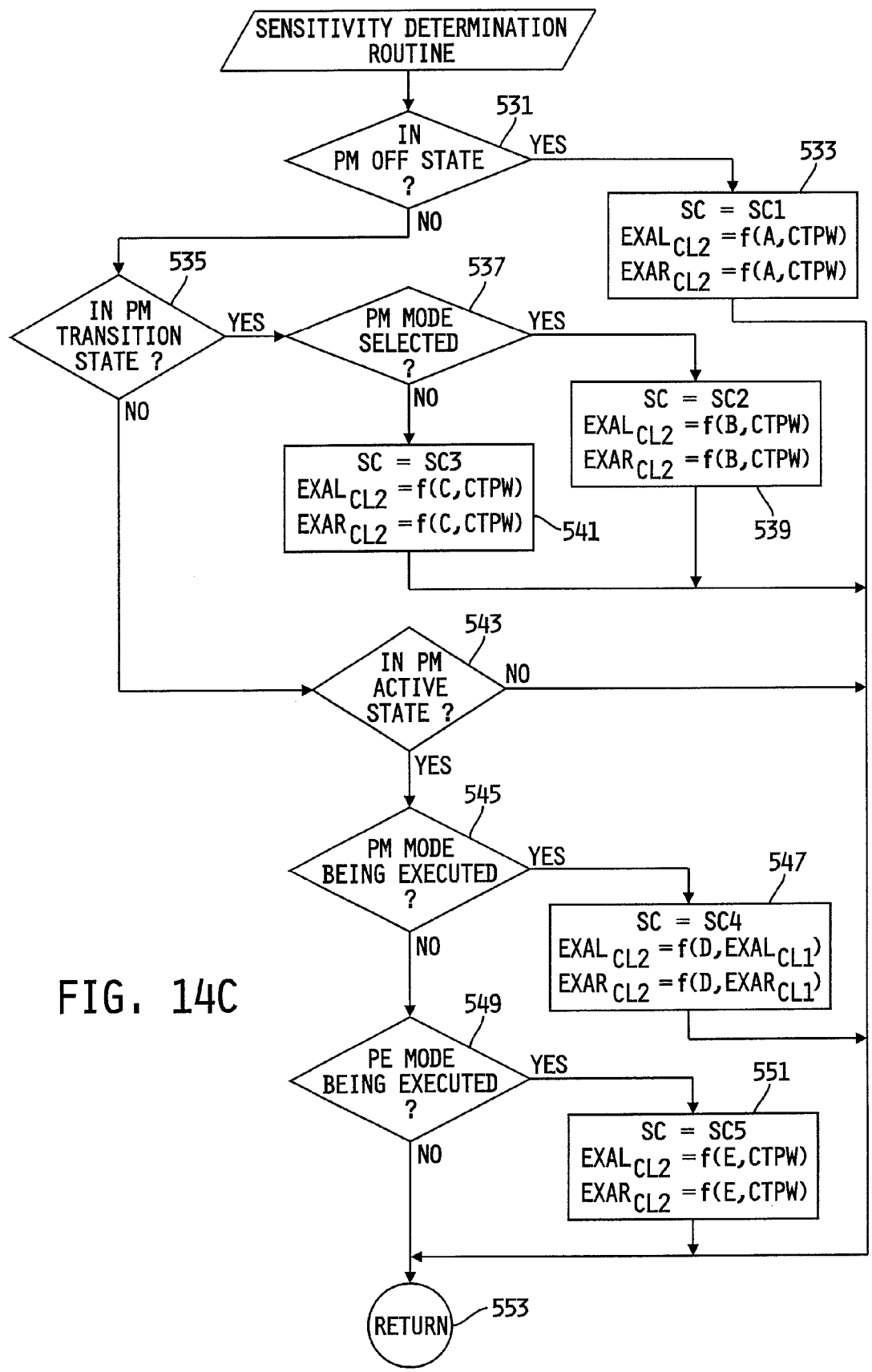

Referring now to FIGS. 14A-14C, a flowchart is shown of one illustrative embodiment of a software algorithm or routine for executing the exit mode routine called by step 186 of the PM Off State routine of FIGS. 7A-7C, by step 362 of the PM Exit/Movement Transition State routine of FIGS. 10A and 10B and by step 452 of the PM Active State routine of FIGS. 11A-11C. In the illustrated embodiment, the exit mode algorithm or routine is configured to implement two different decision criteria. One such decision criterion eliminates one side 60c or 60d and either the head end 60a or foot end 60b of the mattress 60, and scans the remaining side and end for current load cell data. The controller 88 compares for each selected side and end the current load cell values, LH, LF, RF, and/or RH, for that side or end with corresponding computed exit condition threshold values, LHT, LFT, RFT, and RHT, to determine whether an exit condition is met. The exit condition threshold values, LHT, LFT, RFT, and RHT, are computed by multiplying the normalized exit condition threshold values, LHTN, LFTN, RFTN and RHTN, in the exit condition threshold table, e.g., Table 1, by a ratio of the corrected total patient weight, CTPW, and the calibration weight, CW.

A second decision criterion implements a "difference formula" that is applied only to the selected side 60c or 60d of the mattress 60. As illustrated by example in FIG. 13, a total weight $484_{1,2}$ of 80 lbs. may result from the sum of a 50 lb. patient $480_{1,2}$ supported by the mattress 60 and a 30 lb. static weight 482, e.g., in the form of medical equipment or other stationary weight, supported by the mattress support frame 58 between the foot end 60b of the mattress 60 and the foot end 64 of the bed 50. It will be understood that the static weight 482 may alternatively be supported by the mattress 60, the mattress support frame 58, and/or the footboard 64b. In any case, the first decision criterion reacts to movement of the total weight on the mattress 60, and does not distinguish between the moving patient weight and stationary, static weight 482. Thus, if the 50 lb. patient $480_{1,2}$ moves from a first position $480_1$ on the mattress 60 to a second position $480_2$ adjacent to the right edge 60c of the mattress 60, e.g., at E64, the first decision criterion will detect only movement of the combined 80 lbs. of weight $484_{1,2}$ from a first position $484_1$ to a second position $484_2$ toward E52 which is not near the edge of the mattress 60. Consequently, the first decision criterion may not detect actual impending exit from the bed 50 of a lightweight patient when a sufficient static weight 482 is also impressed on the mattress 60, mattress support frame 58 and/or footboard 64b, as illustrated by example in FIG. 13. This phenomenon becomes more pronounced as the patient weight nears the static weight. The second decision criterion using the aforementioned "difference formula" is accordingly implemented to account for non-moving weight that may be included in the total patent weight as illustrated by example in FIG. 13. It will be appreciated that the difference formula may alternatively be configured to account for static weight positioned at or around the head end 62 of the bed 50, or at or around any other particular location of the mattress, and any such modifications to the software algorithms and/or routines described herein to accommodate such alternative positioning of the static weight 482 are contemplated by this disclosure. In any case, however, it will be noted that the controller 88 is at no time operable to compute an actual position of the patient $480_{1,2}$, the static weight 482, or the combined weight $484_{1,2}$ relative to a reference position. Rather, the scenario illustrated in FIG. 13 with respect to the patient $480_{1,2}$, the static weight 482, and the combined weight $484_{1,2}$ is provided only by way of example to illustrate a patient exit scenario that the PE mode routine of FIGS. 14A and 14B is designed to address.

Referring again to FIGS. 14A and 14B, the exit routine begins at step 500 where the controller 88 is operable to execute a sensitivity determination routine. The exit mode routine illustrated in FIGS. 14A-14B may be called during any of several operating states of the state machine 120. It is desirable to configure the sensitivity of the exit mode routine differently depending upon which of the operating states of the state machine 120 calls the exit mode routine, and the sensitivity determination routine is accordingly operable to scale the sensitivity of the first and second decision criteria to the current values of the load cell weight values.

Referring to FIG. 14C, one illustrative embodiment of the sensitivity determination routine of step 500 is shown. In the illustrated embodiment, the sensitivity determination routine begins at step 531 where the controller 88 is operable to determine whether the state machine 120 is currently in the PM Off State 122. If so, execution of the routine advances to step 533 where the controller 88 is operable to set a scale factor, SC, to a first scale factor value, SC1. The scale factor, SC, scales the sensitivity of the first decision criterion of the exit mode algorithm to current load cell weight values, as will be described in greater detail hereinafter. In any case, the controller 88 is further operable at step 533 to define equations for a second left side exit adjust clamp value, $EXAL_{CL2}$ and also for a second right side exit adjust clamp value, $EXAR_{CL2}$. In the illustrated embodiment, $EXAL_{CL2}$ and $EXAR_{CL2}$ are generally defined as a function of one or more constants, represented by the constant vector, A, and the corrected total patient weight. In one specific embodiment, $EXAL_{CL2}=EXAR_{CL2}=A1$ when $CTPW>W_{TH}$, and otherwise $EXAL_{CL2}=EXAR_{CL2}=A2$, where A1 and A2 are constants, and $W_{TH}$ is a threshold weight value, e.g., 40 lbs. $EXAL_{CL2}$ and $EXAR_{CL2}$ scale the sensitivity of the second decision criterion of the exit mode algorithm to current load cell weight values, as will be described in greater detail hereinafter. It will be appreciated that $EXAL_{CL2}$ and $EXAR_{CL2}$ may alternatively be defined according to other functions of A and CTPW, and/or according to functions of additional or different parameters, without detracting from the scope of the claims appended hereto. In any case, if the controller 88 determines at step 531 that the state machine 120 is not currently in the PM Off State 122, execution of the routine advances to step 535 where the controller 88 is operable to determine whether the state machine 120 is currently in the PM Movement/Exit Transition State 128.

If, at step 535, the controller 88 determines that the state machine 120 is currently in the PM Movement/Exit Transition State 128, execution of the routine advances to step 537 where the controller 88 is operable to determine whether the PM mode or the PE mode has been selected in the PM Movement/Exit Transition State 128. If the patient movement (PM) mode has been selected, execution of the routine advances to step 539 where the controller 88 is operable to set the scale factor, SC, to a second scale factor value, SC2. The controller 88 is further operable at step 539 to define equations for the second left side exit adjust clamp value, $EXAL_{CL2}$ and also for the second right side exit adjust clamp value, $EXAR_{CL2}$. In the illustrated embodiment, $EXAL_{CL2}$ and $EXAR_{CL2}$ are generally defined as a function of one or more constants, represented by the constant vector, B, and the corrected total patient weight. In one specific embodiment, $EXAL_{CL2}=EXAR_{CL2}=B1$ when $CTPW>W_{TH}$, and otherwise $EXAL_{CL2}=EXAR_{CL2}=B2$, where B1 and B2 are constants, and $W_{TH}$ is a threshold weight value, e.g., 40 lbs. It will be appreciated that $EXAL_{CL2}$ and $EXAR_{CL2}$ may alternatively be defined according to other functions of B and CTPW, and/or according to functions of additional or different parameters, without detracting from the scope of the claims appended hereto. In any case, if the controller 88 determines step 537 that the PE mode was instead selected in the PM Movement/Exit Transition State 128, execution of the routine advances to step 541 where the controller 88 is operable to set the scale factor, SC, to a third scale factor value, SC3. The controller 88 is further operable at step 541 to define equations for the second left side exit adjust clamp value, $EXAL_{CL2}$ and also for the second right side exit adjust clamp value, $EXAR_{CL2}$. In the illustrated embodiment, $EXAL_{CL2}$ and $EXAR_{CL2}$ are generally defined as a function of one or more constants, represented by the constant vector, C, and the corrected total patient weight. In one specific embodiment, $EXAL_{CL2}=EXAR_{CL2}=C1$ when $CTPW>W_{TH}$, and otherwise $EXAL_{CL2}=EXAR_{CL2}=C2$, where C1 and C2 are constants, and $W_{TH}$ is a threshold weight value, e.g., 40 lbs. It will be appreciated that $EXAL_{CL2}$ and $EXAR_{CL2}$ may alternatively be defined according to other functions of C and CTPW, and/or according to functions of additional or different parameters, without detracting from the scope of the claims appended hereto. It will be further appreciated that any two or more of SC1, SC2 and SC3 may have identical values or they may instead all have different values. Likewise, any two or more of the constant vectors A, B and C may contain identical constant values, or they may instead all contain different constant values. In any case, if the controller 88 determines at step 535 that the state machine 120 is not current in the PM Movement/Exit Transition State 128, execution of the routine advances to step 543 where the controller 88 is operable to determine whether the state machine 120 is currently in the PM Active State 130.

If, at step 543, the controller 88 determines that the state machine 120 is currently in the PM Active State 130, execution of the routine advances to step 545 where the controller 88 is operable to determine whether the PM mode is being executed in the PM Active State 128. If so, execution of the routine advances to step 547 where the controller 88 is operable to set the scale factor, SC, to a fourth scale factor value, SC4. The controller 88 is further operable at step 547 to define equations for the second left side exit adjust clamp value, $EXAL_{CL2}$ and also for the second right side exit adjust clamp value, $EXAR_{CL2}$. In the illustrated embodiment, $EXAL_{CL2}$ is generally defined as a function of one or more constants, represented by the constant vector, D, and as a function of a first left side exit adjust clamp value, $EXAL_{CL1}$, and $EXAR_{CL2}$ is generally defined as a function of D and as a function of a first right side exit adjust clamp value, $EXAR_{CL1}$. In one specific embodiment, $EXAL_{CL2}=EXAL_{CL1}-D1$, and if $EXAL_{CL2}<D2$ then $EXAL_{CL2}=D2$ and if $EXAL_{CL2}>D3$ then $EXAL_{CL2}=D3$, where D1, D2 and D3 are constants. In this embodiment, $EXAR_{CL2}$ is similarly defined according to the equations $EXAR_{CL2}=EXAR_{CL1}-D1$, and if $EXAR_{CL2}<D2$ then $EXAR_{CL2}=D2$ and if $EXAR_{CL2}>D3$ then $EXAR_{CL2}=D3$. It will be appreciated that $EXAL_{CL2}$ and $EXAR_{CL2}$ may alternatively be defined according to other functions of D, $EXAL_{CL1}$ and $EXAR_{CL1}$, and/or according to functions of additional or different parameters, without detracting from the scope of the claims appended hereto. In any case, if the controller 88 determines step 545 that the PM mode is not being executed in the PM Active State 130, execution of the routine advances to step 549 where the controller 88 is operable to determine whether the patient exit (PE) mode is being executed in the PM Active State 130.

If the controller determines at step 549 that the PE mode is being executed in the PM Active state 130, execution of the routine advances to step 551 where the controller 88 is operable to set the scale factor, SC, to a fourth scale factor value, SC5. The controller 88 is further operable at step 551 to define equations for the second left side exit adjust clamp value, $EXAL_{CL2}$ and also for the second right side exit adjust clamp value, $EXAR_{CL2}$. In the illustrated embodiment, $EXAL_{CL2}$ and $EXAR_{CL2}$ are generally defined as a function of one or more constants, represented by the constant vector, E, and as a function of the corrected total patient weight, CTPW. In one specific embodiment, $EXAL_{CL2}=EXAR_{CL2}=(E1-CTPW)/$ E2 if CTPW<E3, and $EXAL_{CL2}=EXAR_{CL2}=(CTPW-E4)/(MAW-E5)$ if CTPW>E6, where E-E6 are constants and MAW is a maximum armed weight value. It will be appreciated that $EXAL_{CL2}$ and $EXAR_{CL2}$ may alternatively be defined according to other functions of E and CTPW, and/or according to functions of additional or different parameters, without detracting from the scope of the claims appended hereto. It will be further appreciated that any two or more of SC1, SC2, SC3, SC4 and SC5 may have identical values or they may instead all have different values. Likewise, any two or more of the constant vectors A, B, C, D and E may contain one or more identical constant values, or they may instead all contain different constant values. In any case, execution of the sensitivity determination routine advances from steps 533, 539, 541, 547, 551 and the "NO" branches of steps 543 and 549 to the return step 553.

The sensitivities of the first and second decision criteria of the Exit Mode routine of FIGS. 14A-14B are thus determined by the sensitivity determination routine of FIG. 14C. As the sensitivities of the first and second decision criteria increase, the movement required by the patient toward any edge of the bed 50 before any of the exit conditions are violated will decrease. Conversely, as the sensitivities of the first and second decision criteria decrease, the movement required by the patient toward any edge of the bed 50 before any of the exit conditions are violated will increase. When arming the system in the PM Movement/Exit Transition State 128 for subsequent execution of either of the patient exit (PE) or patient movement (PM) modes, the sensitivities of the first and second decision criteria are increased over what they would otherwise be when executing the PM or PE modes. This makes the first and second decision criteria very sensitive to movement of the patient toward any edge of the bed and thereby effectively defines the safe arming zone as a region of the mattress 60 that is remote from any edge of the bed 50 and therefore substantially central to the mattress 60. To arm the system for transition of the state machine 120 from the PM Movement/Exit Transition State 128 to the PM Active State 130, the patient will accordingly be required to be positioned approximately centrally on the mattress 60. If the patient is instead outside of the safe arming zone when attempting to arm the system, the local alarm will chirp some number of times and the state machine 120 will return to the PM Off State 122 as illustrated in the flowchart of FIGS. 10A-10C. In order to properly arm the system for transition of the state machine 120 from the PM Movement/Exit Transition State 128 to the PM Active State 130, it will be necessary for a caregiver to position or reposition the patient approximately centrally on the mattress 60.

Referring again to FIG. 14A, the exit mode routine advances from step 500 to step 501 where the controller 88 is operable to determine which load cells to monitor for potential exit conditions relating to one side or the other of the mattress 60. In the illustrated embodiment, the controller 88 is operable to determine whether RF>LF and RH>LF. If not, execution of the routine advances to step 502 where the controller 88 is operable to scan a subset of the exit condition threshold table having sets of exit condition threshold values defined at the left side 60d of the mattress 60. Thereafter at step 503, the controller 88 is operable to execute the first decision criterion by comparing the current left head load cell value, LH, with a scaled representation of the Ith left head load cell threshold value, $SC*LHT\_I$, in the scan, where $LHT\_I=LHTN(I)*(CTPW/CW)$, and where LHTN(I) is the LHTN value in the Ith set of exit condition threshold values of the exit condition threshold table, e.g., Table 1. The controller 88 is further operable at step 503 to compare the current left foot load cell value, LF, with a scaled representation of the Ith left foot load cell threshold value, $SC*LFT\_I$, in the scan, where $LFT\_I=LFTN(I)*(CTPW/CW)$, and where LFTN(I) is the LFTN value in the Ith set of exit condition threshold values of the exit condition threshold table, e.g., Table 1. In any case, if both conditions are met, i.e., if $LH>SC*LHT\_I$ and $LF>LFT\_I$, execution of the routine advances to step 544 where the controller 88 is operable to compare an exit counter to a counter limit, CL. If the exit counter is greater than CL, execution of the routine advances to step 546 where the controller 88 is operable to set a patient exiting zone flag, PEZ, to "true" to thereby indicate that the patient is not in the safe arming zone of the bed 50 as described hereinabove. Thereafter at step 547, the controller 88 is operable to determine whether the state machine 120 is currently operating in the PM Active State 130. If not, no alarms will be activated and execution of the routine instead advances to the return step 552. If, on the other hand, the controller 88 determines at step 547 that the state machine 120 is currently operating in the PM Active State 130, execution of the routine advances to step 548 where the controller 88 is operable to set the remote alarm flag to an active state and to set the local alarm flag to an active state. Thereafter at step 549 the state machine moves to the PM Alarm State 136, and the controller 88 is accordingly operable to execute the PM Alarm State routine of FIG. 12. If, at step 544, the controller 88 determines that the exit counter is not greater than the counter limit, CL, execution of the routine advances to step 550 where the controller 88 is operable to increment the exit counter. Thereafter, execution of the exit mode routine advances to the return step 552.

If, at step 503 the controller 88 determines that at least one of the illustrated conditions is not true, execution of the routine advances to step 504 where the controller 88 is operable to execute the second decision criterion by comparing the current left foot load cell value, LF, with a scaled representation of the Ith left foot load cell threshold value, $SC*LFT\_I$, in the scan, where $LFT\_I=LFTN(I)*(CTPW/CW)$, and LFTN(I) is the LFTN value in the Ith set of exit condition threshold values of the exit condition threshold table, e.g., Table 1. The controller 88 is then operable to set a foot variable, FOOT_I, equal to the current value of "I" if LF is greater than $SC*LFT\_I$. Thereafter at step 506, the controller 88 is likewise operable to compare the current left head load cell value, LH, with a scaled representation of the Ith left head load cell threshold value, $SC*LHT\_I$, in the scan, where $LHT\_I=LHTN(I)*(CTPW/CW)$, and LHTN(I) is the LHTN value in the Ith set of exit condition threshold values of the exit condition threshold table, e.g., Table 1. The controller 88 is then operable to set a head variable, HEAD_I, equal to the current value of "I" if LH is greater than $SC*LHT\_I$. Thereafter at step 508, the controller 88 is operable to compute a possible left side exit condition as an average of FOOT_I and HEAD_I, e.g., according to the equation $AVGI=(FOOT\_I-HEAD\_I)/2$. In an alternative embodiment of the exit mode routine, step 503 may be implemented after step 508 where the AVGI value is computed.

From step 508, execution of the routine advances to step 510 where the controller 88 is operable to compute a left-side exit adjust value, EXAL, where EXAL is inversely proportional to the amount of static load located at the foot end 64 of the bed 50. In the illustrated embodiment, the controller 88 is operable to compute EXAL according to the equation $EXAL=[(LHT\_AVGI-LH)/(RF-RFT\_AVGI)]/EXAC$, where $LHT\_AVGI=LHTN\_AVGI*CTPW/CW$, $RFT\_AVGI=RFTN\_AVGI*CTPW/CW$, EXAC is an exit adjust constant, and LHTN_AVGI and RFTN_AVGI are the LHTN and RFTN values in the Ith set of exit condition threshold values of the exit condition threshold table, e.g., Table 1. It will be understood that this formula for EXAL represents a specific implementation of a more general equation for EXAL for one specific type of hospital bed 50, i.e., the VersaCare bed described hereinabove. A more general EXAL formula that may be applied to other embodiments of the bed 50 is EXAL=[[(LHT_AVGI−LH)/(RF−RFT_AVGI)]+ [(RHT_AVGI−RH)/(LF−LFT_LVGI)]]/EXAC, where LHT_AVGI=LHTN_AVGI*CTPW/CW, RFT_AVGI=RFTN_AVGI*CTPW/CW, RHT_AVGI=RHTN_AVGI*CTPW/CW, LFT_AVGI=LFTN_AVGI*CTPW/CW, EXAC is the exit adjust constant, and LHTN_AVGI, RFTN_AVGI, RHTN_AVGI and LFTN_AVGI are the LHTN, RFTN, RHTN and LFTN values in the Ith set of exit condition threshold values of the exit condition threshold table, e.g., Table 1.

Execution of the routine advances from step 510 to step 512 where the controller 88 is operable to compute the percentage of LF relative to the corrected total patient weight, CTPW according to the equation LF %=LF/CTPW, and to then determine a first clamped left-side exit adjust value, $EXAL_{CL1}$, as a function of LF %. In one embodiment, the function of LF % is configured such that $EXAL_{CL1}$ is decreased as LF % increases. $EXAL_{CL1}$ may be alternatively or additionally determined as a function of AVGI, for example, according to the equation $EXAL_{CL1}=EXAL_{CL1}-K1*(AVGI-K2)$, where K1 and K2 are constants. $EXAL_{CL1}$ may be alternatively or additionally still determined as a function of the corrected total patient weight, CTPW, for example, according to the equation $EXAL_{CL1}=EXAL_{CL1}+K3*(CTPW-K4)$, where K3 and K4 are constants.

In any case, execution of the exit mode routine advances from step 512 to step 513 where the controller 88 is operable to compute the second clamped left side exit adjust value, $EXAL_{CL2}$, according to an appropriate one of the equations established by the sensitivity determination routine of FIG. 14C. Thereafter at step 514, the controller 88 is operable in one embodiment to compute the following values, TA=(LH−RH), TB=$EXAL_{CL2}$*(LHT_AVGI−RHT_AVGI), TC=LF−RF and TD=$EXAL_{CL2}$*(LFT_AVGI−RFT_AVGI), where LHT_AVGI, LFT_AVGI, RHT_AVGI, and RFT_AVGI correspond to the AVGIth set of LHTN, RHTN, LFTN and RFTN exit condition threshold values in the exit condition threshold table, e.g., Table 1, each multiplied by (CTPW*CW). In an alternative embodiment, the equations for TB and TD may omit $EXAL_{CL2}$ so that TB=(LHT_AVGI−RHT_AVGI) and TD=(LFT_AVGI−RFT_AVGI). In any case, execution of the routine advances to step 516 where the controller 88 is operable to compare the relationship (TA−TB)+(TC−TD) to zero. If the controller 88 determines at step 516 that (TA−TB)+(TC−TD)>0, a potential impending exit condition is identified and execution of the routine advances to step 544. If, at step 516, the controller 88 determines that (TA−TB)+(TC−TD) is not greater than zero, an impending exit condition is not identified and execution of the routine advances to step 554 where the controller 88 is operable to clear the exit counter. The controller 88 is operable thereafter at step 555 to set the patient exiting zone flag, PEZ, to "false", to thereby indicate that the patient is in the safe arming zone of the bed 50 as described hereinabove. Execution of the exit state routine advances from step 555 to the return step 552.

If, at step 500, the controller 88 determines that RF>LF AND RH>LF, execution of the routine advances to step 518 where the controller 88 is operable to scan a subset of the exit condition threshold table having sets of exit condition threshold values defined at the right side 60c of the mattress 60. Thereafter at step 519, the controller 88 is operable to execute the first decision criterion by comparing the current right head load cell value, RH, with a scaled representation of the Ith right head load cell threshold value, SC*RHT_I, in the scan, where RHT_I=RHTN(I)*(CTPW/CW), and where RHTN(I) is the RHTN value in the Ith set of exit condition threshold values of the exit condition threshold table, e.g., Table 1. The controller 88 is further operable at step 519 to compare the current right foot load cell value, RF, with a scaled representation of the Ith right foot load cell threshold value, SC*RFT_I, in the scan, where RFT_I=RFTN(I)*(CTPW/CW), and where RFTN(I) is the RFTN value in the Ith set of exit condition threshold values of the exit condition threshold table, e.g., Table 1. In any case, if both conditions are met, i.e., if RH>SC*RHT_I and RF>RFT_I, execution of the routine advances to step 544.

If, at step 519 the controller 88 determines that at least one of the illustrated conditions is not true, execution of the routine advances to step 520 where the controller 88 is operable to execute the second decision criterion by comparing the current right foot load cell value, RF, with a scaled representation of the Ith right foot load cell threshold value, SC*RFT_I, in the scan, where RFT_I=RFTN(I)*(CTPW/CW), and RFTN(I) is the RFTN value in the Ith set of exit condition threshold values of the exit condition threshold table, e.g., Table 1. The controller 88 is then operable to set a foot variable, FOOT_I, equal to the current value of "I" if RF is greater than SC*RFT_I. Thereafter at step 522, the controller 88 is likewise operable to compare the current left head load cell value, RH, with a scaled representation of the Ith right head load cell threshold value, SC*RHT_I, in the scan, where RHT_I=RHTN(I)* (CTPW/CW), and RHTN(I) is the RHTN value in the Ith set of exit condition threshold values of the exit condition threshold table, e.g., Table 1. The controller 88 is then operable to set a head variable, HEAD_I, equal to the current value of "I" if RH is greater than SC*RHT_I. Thereafter at step 524, the controller 88 is operable to compute a possible right side exit condition as an average of FOOT_I and HEAD_I e.g., according to the equation AVGI= (FOOT_I−HEAD_I)/2. In an alternative embodiment of the exit mode routine, step 519 may be implemented after step 524 where the AVGI value is computed.

From step 524, execution of the routine advances to step 526 where the controller 88 is operable to compute a right-side exit adjust value, EXAR, where EXAR is inversely proportional to the amount of static load located at the foot end 64 of the bed 50. In the illustrated embodiment, the controller 88 is operable to compute EXAR according to the equation EXAR=[(RHT_AVGI−RH)/(LF−LFT_AVGI)]/EXAC, where RHT_AVGI=RHTN_AVGI*CTPW/CW, LFT_AVGI=LFTN_AVGI*CTPW/CW, EXAC is an exit adjust constant, and RHTN_AVGI and LFTN_AVGI are the RHTN and LFTN values in the Ith set of exit condition threshold values of the exit condition threshold table, e.g., Table 1. It will be understood that this formula for EXAR represents a specific implementation of a more general equation for EXAR for one specific type of hospital bed 50, i.e., the VersaCare bed described hereinabove. A more general EXAR formula that may be applied to other embodiments of the bed 50 is EXAR=[[(RHT_AVGI−RH)/(LF−LFT_AVGI)]+[(LHT_AVGI−LH)/(RF−RFT_AVGI)]]/ EXAC, where RHT_AVGI=RHTN_AVGI*CTPW/CW, LFT_AVGI=LFTN_AVGI*CTPW/CW, LHT_AVGI=LHTN_AVGI*CTPW/CW, RFT_AVGI=RFTN_AVGI*CTPW/CW, EXAC is the exit adjust constant, and RHTN_AVGI, LFTN_AVGI, LHTN_AVGI and RFTN_AVGI are the RHTN, LFTN, LHTN and RFTN values in the Ith set of exit condition threshold values of the exit condition threshold table, e.g., Table 1.

Execution of the routine advances from step 526 to step 528 where the controller 88 is operable to compute the percentage of RF relative to the corrected total patient weight, CTPW according to the equation RF %=RF/CTPW, and to then determine a first clamped right-side exit adjust value, $EXAR_{CL1}$, as a function of RF %. In one embodiment, the function of RF % is configured such that $EXAR_{CL1}$ is decreased as RF % increases. $EXAR_{CL1}$ may be alternatively or additionally determined as a function of AVGI, for example, according to the equation $EXAR_{CL1}=EXAR_{CL1}-K1*(AVGI-K2)$, where K1 and K2 are constants. $EXAR_{CL1}$ may be alternatively or additionally still determined as a function of the corrected total patient weight, CTPW, for example, according to the equation $EXAR_{CL1}=EXAR_{CL1}+K3*(CTPW-K4)$, where K3 and K4 are constants.

Execution of the exit mode routine advances from step 528 to step 529 where the controller 88 is operable to determine the second clamped right-side exit adjust value, $EXAR_{CL2}$, according to an appropriate one of the equations established by the sensitivity determination routine of FIG. 14C Execution of the routine then advances from step 529 to step 530 where the controller 88 is operable to compute the following values, TA=(RH−LH), TB=$EXAR_{CL2}$*(RHT_AVGI−LHT_AVGI), TC=RF−LF and TD=$EXARCL_2$*(RFT_AVGI−LFT_AVGI), where LHT_AVGI, LFT_AVGI, RHT_AVGI, and RFT_AVGI correspond to the AVGIth set of LHTN, RHTN, LFTN and RFTN exit condition threshold values in the exit condition threshold table, e.g., Table 1, each multiplied by (CTPW*CW). In an alternative embodiment, the equations for TB and TD may omit $EXAR_{CL2}$ so that TB=(RHT_AVGI−LHT_AVG_I) and TD=(RFT_AVGI−LFT_AVGI). In any case, execution of the routine advances to step 532 where the controller 88 is operable to compare the relationship (TA−TB)+(TC−TD) to zero. If the controller 88 determines at step 532 that (TA−TB)+(TC−TD)>0, a potential impending exit condition is identified and execution of the routine advances to step 544. If, at step 532, the controller 88 determines that (TA−TB)+(TC−TD) is not greater than zero, an impending exit condition is not identified and execution of the routine advances to step 554.

Along with step 501, the controller 88 is operable to execute step 534 where the controller 88 is operable to determine which load cells to monitor for potential exit conditions relating to the head end 60a or the foot end 60b of the mattress 60. In the illustrated embodiment, the controller 88 is operable at step 534 to determine whether RF>RH AND LF>

LH. If so, execution of the routine advances to step 536 where the controller 88 is operable to scan a subset of the exit condition threshold table having sets of exit condition threshold values defined at the foot end 60b of the mattress 60. Thereafter at step 538, the controller 88 is operable to execute the first decision criterion by comparing the current right foot load cell value, RF, with a scaled representation of the Ith right foot load cell threshold value, SC*RFT_I, in the scan, where RFT_I=RFTN(I)*(CTPW/CW), and where RFTN(I) is the RFTN value in the Ith set of exit condition threshold values of the exit condition threshold table, e.g., Table 1. The controller 88 is further operable at step 538 to compare the current left foot load cell value, LF, with a scaled representation of the Ith left foot load cell threshold value, SC*LFT_I, in the scan, where LFT_I=LFTN(I)*(CTPW/CW), and where LFTN(I) is the LFTN value in the Ith set of exit condition threshold values of the exit condition threshold table, e.g., Table 1. If both conditions are met, i.e., if RF>SC*RFT_I and RH>SC*RHT_I, execution of the routine advances to step 544. If, at step 538 the controller 88 determines that at least one of the illustrated conditions is not true, execution of the routine advances to step 554.

If, at step 534, the controller 88 determines that at least one of the illustrated conditions is not true, execution of the routine advances to step 540 where the controller 88 is operable to scan a subset of the exit condition threshold table having sets of exit condition threshold values defined at the head end 60a of the mattress 60. Thereafter at step 542, the controller 88 is operable to execute the first decision criterion by comparing the current right head load cell value, RH, with a scaled representation of the Ith right head load cell threshold value, SC*RHT_I, in the scan, where RHT_I=RHTN(I)*(CTPW/CW), and where RHTN(I) is the RHTN value in the Ith set of exit condition threshold values of the exit condition threshold table, e.g., Table 1. The controller 88 is further operable at step 542 to compare the current left head load cell value, LH, with a scaled representation of the Ith left head load cell threshold value, SC*LHT_I, in the scan, where LHT_I=LHTN(I)*(CTPW/CW), and where LHTN(I) is the LHTN value in the Ith set of exit condition threshold values of the exit condition threshold table, e.g., Table 1. If both conditions are met, i.e., if RH>SC*RHT_I and LH>SC*LHT_I, execution of the routine advances to step 544. If, at step 538 the controller 88 determines that at least one of the illustrated conditions is not true, execution of the routine advances to step 554.

In one exemplary embodiment of the system 75, the controller 88 is configured, pursuant to the patient movement (PM) mode of the PM Active State 130, to identify excessive movement of the patient relative to a reference load cell distribution by comparing the current distribution of the patient's weight over the two or three of the load cells 68a-68d to a predefined collection of load cell movement threshold data. In the illustrated embodiment, this predefined collection of load cell movement data is provided in the form of a number of tables of a number of sets of load cell movement threshold values, although the collection of load cell movement data may alternatively provided in the form of one or more equations, graphs, charts or the like.

Figure 15:
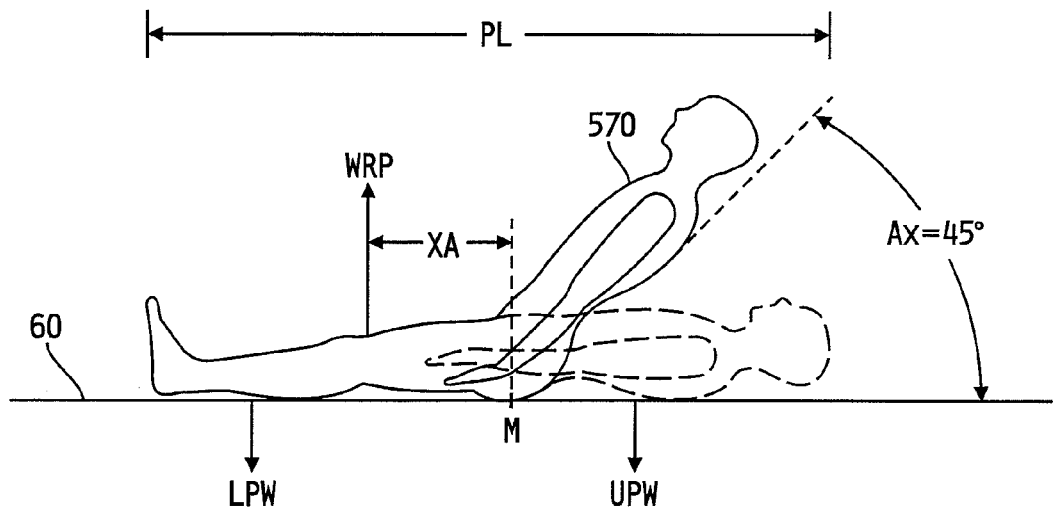
FIG. 15 is a diagram illustrating a mathematical model of vertical movement of a patient in the hospital bed of FIGS. 1A-1C.
Figure 16:
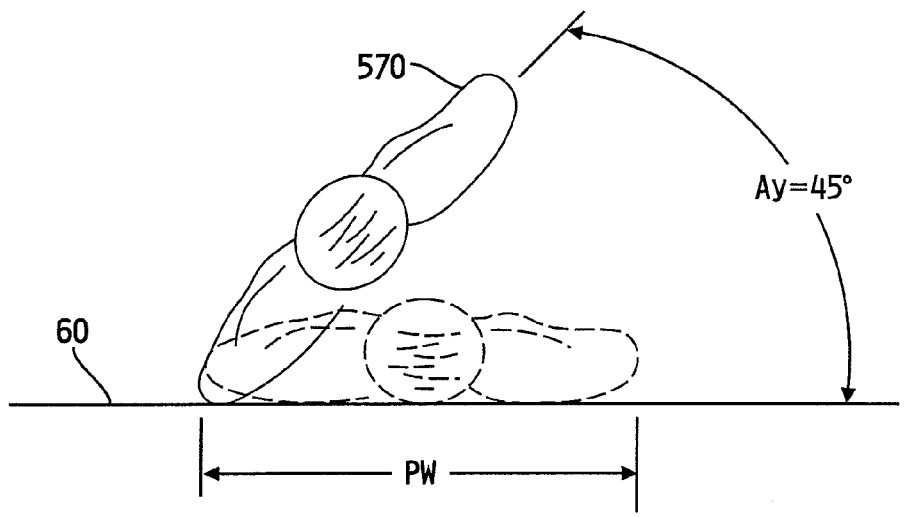
FIG. 16 is a diagram illustrated a mathematical model of horizontal movement of a patient in the hospital bed of FIGS. 1A-1C.
Figure 17:
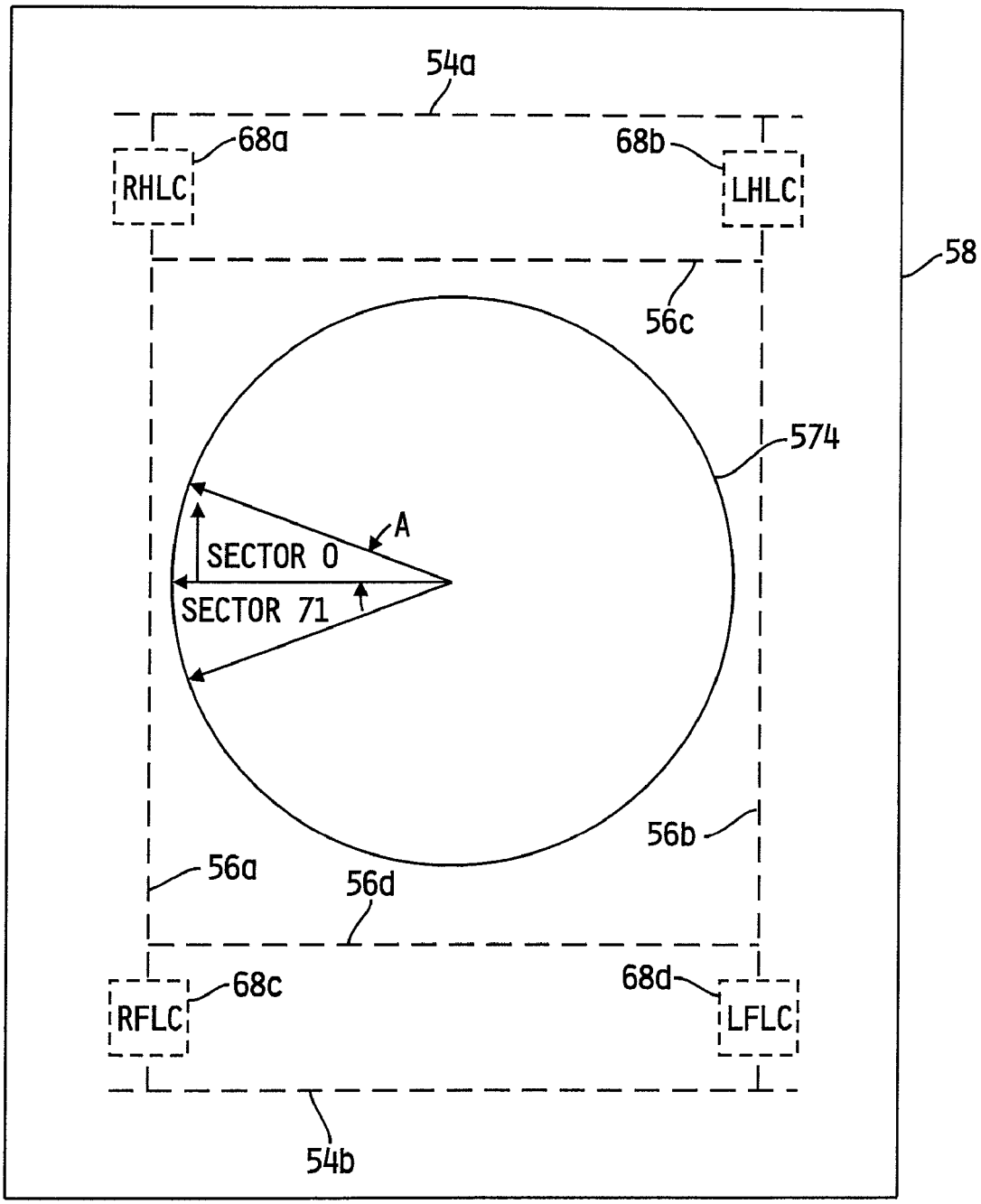
FIG. 17 is a block diagram illustrating one example construction of a movement condition threshold table for use by a patent movement routine called by the PM Active STATE software routine of FIGS. 11A-11C.

Referring now to FIGS. 15-17, a diagram of the bed 50 is shown illustrating one example implementation and construction of two such tables of load cell movement threshold values. In this example, load cell movement threshold data for the first load cell movement threshold table, Table 2, is established according to a model of patient movement within a hospital bed such as the hospital bed 50 illustrated and described hereinabove with respect to FIGS. 1A-1C. Referring specifically to FIG. 15, a patient 570 is shown elevating an upper body portion from a prone position to an incline position, with an angular displacement therebetween of approximately AX=45 degrees. UPW is defined as the portion of the corrected total patient weight, CTPW, attributable to the upper body portion of the patient 570, and LPW is defined as the portion of CTPW attributable to the lower body portion of the patient 570. WRP is defined as the reaction force of the mattress 60 to the patient's weight, CTPW, and XA is defined as the distance between M, the bending point of patient 570, and WRP. PL is defined as the length, or height, of the patient from head to feet. Assuming that LPW is approximately equal to UPW, and assuming that the length of the patient from the patient's waist to the patient's feet is 2*PL/3 and the length of the patient from the patient's waist to the top of the patient's head is PL/3, it can be shown via known physical principles that the patient's weight shifts a distance of approximately 0.024 PL, or approximately 2.4% of the patient's length in the X direction, which is parallel to the length of the patient, when the patient sits up from a prone position to about 45 degrees as illustrated in FIG. 15.

Referring specifically to FIG. 16, the patient 570 of width PW is shown rolling approximately 45 degrees to one side. Assuming PW=PL/4, it can be shown via known physical principles that the patient's weight shifts a distance of approximately 0.036 PL, or approximately 3.5% of the patient's length in the Y direction, which is transverse to the length of the patient, when the patient rolls sideways from a prone position, with the patient's back lying on the mattress 60, to a position of about 45 degrees from the prone position as illustrated in FIG. 16.

Patient movement in a hospital bed is modeled as a combination of the two different movement types illustrated in FIGS. 15 and 16. In other words, typical movement of a patient lying in a hospital bed is modeled as a combination of side-rolling and raising of the upper body portion. From the above relationships, the ratio of patient movement in the X direction relative to the Y direction is thus approximately 1.5:1.

Depending upon the bed type, the distance between the load cells 68a and 68c (or 68b and 68d) may be 2-3 times more than the distance between the load cells 68a and 68b (or 68c and 68d). Assuming that this distance ratio is 1:2, then it takes twice as much movement from the head end 60a toward the foot end 60b (or vice versa) of the mattress 60 as compared with movement from the side 60c to the side 60d (or vice versa) of the mattress 60 to get the same amount of weight distribution.

Combining these two effects, the ratio of redistribution of weight on the load cells 68a-68d is approximately 3:1 when the patient moves in the X direction relative to the Y direction. In the head-raising model, it was assumed that LPW:UPW=1:1, although it should be noted that when a sick patient exits a hospital bed the back is generally curved when the head is raised. A more realistic assumption for LPW:UPW is thus between 1:1 and 1:2, resulting in a net effective load cell redistribution ratio of approximately 4:1, which implies that the patient weight shift seen by the load cells 68a-68d will be approximately 4 times as great when the patient rolls approximately 45 degrees to the side as compared to when the patient sits up at approximately 45 degrees.

Implementing the above relationships in a patient movement model, the effect on the four load cells 68a-68d of patient movement in any direction is modeled as a combination of movement in the X direction (sine) and movement in the Y direction (cosine) according to an equation of the form PCLC=+/−((CTPW/4)*(1/S)*Cos(A))+/−((CTPW/4)*(1/S)*(¼)* Sin(A)), wherein PCLC corresponds to the percentage weight change seen by any of the four load cells 68a-68d, CTPW is the corrected total patient weight, "S" is a sensitivity value, and "A" is the angle of patient movement relative to a reference direction. CTPW/4 represents the approximated average of total weight seen by each of the four load cells, and the additional ¼ factor multiplying the sine function represents the 4:1 net effective load cell ratio just described.

Referring specifically to FIG. 17, the above equation is applied to the surface of the mattress 60 or mattress support frame 58, resulting in the following four equations relating the above PCLC relationship to the percentage weight change seen by each of the load cells RHLC, RFLC, LFLC and LHLC, $$PCRH=((CTPW/4)*(1/S)*\text{Cos}(A))+((CTPW/4)*(1/S)*(¼)*\text{Sin}(A)) \quad (1),$$

$$PCRF=((CTPW/4)*(1/S)*\text{Cos}(A))-((CTPW/4)*(1/S)*(1/4)*\text{Sin}(A)) \quad (2),$$

$$PCLF=-((CTPW/4)*(1/S)*\text{Cos}(A))-((CTPW/4)*(1/S)*(¼)*\text{Sin}(A)) \quad (3),$$

$$PCLH=-((CTPW/4)*(1/S)*\text{Cos}(A))+((CTPW/4)*(1/S)*(¼)*\text{Sin}(A)) \quad (4).$$

By applying equations (1)-(4) to an arbitrary point on the surface 65 of the mattress 60, patent movement in any direction about a periphery 580 of that arbitrary point may be monitored. Resolution of such patient movement monitoring is determined by the number of sectors defining a 360-degree virtual boundary about the arbitrary point, and the total number of sectors is determined by the increment value used for the angle "A." In the illustrated example, the angle "A" is advanced at 5-degree increments, thereby creating 72 sectors radiating outwardly from an arbitrary and unknown point. More or fewer sectors may be defined via an appropriate choice of increments of the angle, "A."

To establish threshold violation criteria for equations (1)-(4), the corrected total patient weight, CTPW, sensitivity, S, and constant values in these equations are represented by constants, K1 and K2, such that the above set of equations are reduced to the following set of calibration equations:

$$RHT=K1*\text{Cos}(A)+K2*\text{Sin}(A) \quad (5),$$

$$RFT=K1*\text{Cos}(A)-K2*\text{Sin}(A) \quad (6),$$

$$LFT=-K1*\text{Cos}(A)-K2*\text{Sin}(A) \quad (7),$$

$$LHT=-K1*\text{Cos}(A)+K2*\text{Sin}(A) \quad (8),$$

where PCRH, PCRF, PCLF and PCLH are replaced in equations (5)-(8) with corresponding threshold values, RHT, RFT, LFT and LHT.

The calibration equations (5)-(8) are used to generate a first one of the tables, Table 2, of load cell movement threshold values. More particularly, Table 2 is populated by a number of sets of movement threshold values forming the load cell movement threshold data, wherein equations (5)-(8) are used to define each set of movement threshold values for a given angle, "A." The following example of Table 2 illustrates a portion of a first collection of movement condition threshold value sets, wherein each set of the movement condition threshold values, RHT, RFT, LFT and LHT, is provided in the form of a percentage value. In the illustrated example, K1=132 and K2=33, although it will be understood that other values may be used. Specific values for K1 and K2 will typically depend upon the application, and may be determined experimentally. The K1 and K2 values may further be refined using one or more conventional optimization techniques. In any case, the example movement condition threshold table illustrated by Table 2 is populated with a total of 72 sets of movement condition threshold values (although only 10 such sets are shown) using angle increments of 5 degrees. It will be understood, however, that the data represented in Table 2, along with the particular manner in which it is generated, is provided only by way of example, and that Table 2 may alternatively be generated using other data types, other angle increment values, and more, fewer and/or different models and/or model parameters. Any such alternate implementation of the illustrated movement condition threshold table, graph, chart or one or more mathematical equations, is contemplated by this disclosure.

TABLE 2

| Angle/Sector | RHT (%) | RFT (%) | LFT (%) | LHT (%) |
|---|---|---|---|---|
| 0/0 | 132 | 132 | −132 | −132 |
| 5/1 | 134 | 129 | −134 | −129 |
| 10/2 | 136 | 124 | −136 | −124 |
| 15/3 | 136 | 119 | −36 | −119 |
| 20/4 | 135 | 113 | −135 | −113 |
| 25/5 | 134 | 106 | −34 | −106 |
| 30/6 | 131 | 98 | −131 | −98 |
| 45/7 | 127 | 89 | −127 | −89 |
| . | . | . | . | . |
| . | . | . | . | . |
| . | . | . | . | . |
| 350/70 | 124 | 136 | −124 | −136 |
| 355/71 | 129 | 134 | −129 | −134 |

TABLE 3

| LHTN (%) | LFTN (%) | RFTN (%) | RHTN (%) | Movement Detected |
|---|---|---|---|---|
| 25 | −25 | 0 | 0 | from head |
| −25 | 25 | 0 | 0 | from foot |
| 0 | 111 | −111 | 0 | from left |
| 0 | −111 | 111 | 0 | from right |
| 0 | 0 | 25 | −25 | from foot |
| 0 | 0 | −25 | 25 | from head |
| −111 | 0 | 0 | 111 | right roll |
| 111 | 0 | 0 | −111 | left roll |
| −35 | 0 | 35 | −1 | diagonal to right front sit up |
| −1 | 35 | 0 | −35 | diagonal to left front sit up |
| 25 | <10 | −25 | 0 | diagonal to left reverse slide |
| 0 | −25 | <10 | 25 | diagonal to right reverse slide |

Figure 18:
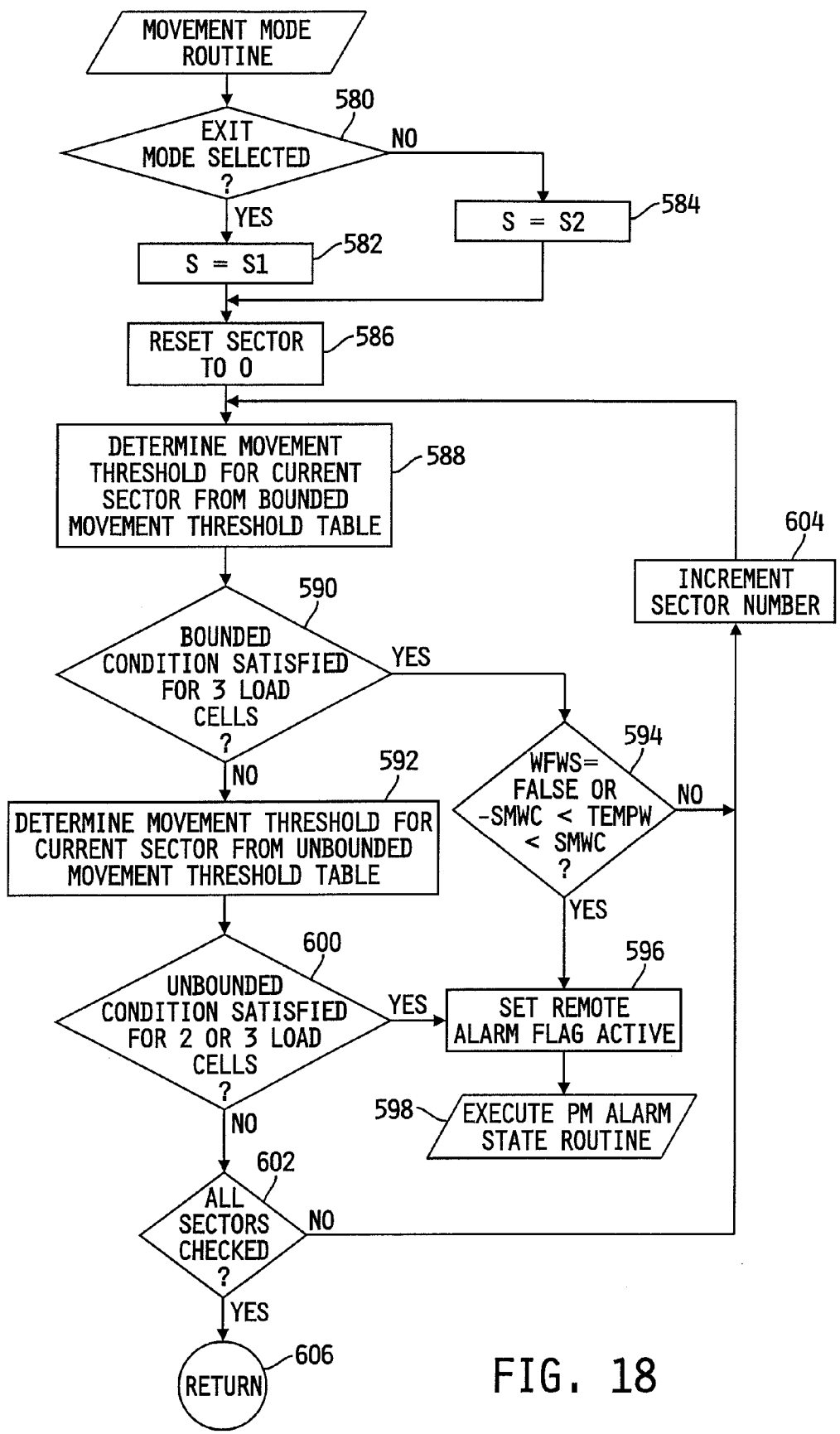
FIG. 18 is a flowchart illustrating an exemplary embodiment of the movement mode routine called by the PM Active State software routine of FIGS. 11A-11C.

If any three of the four percentage weight change values, PCRH, PCRF, PCLF and PCLH, computed by equations (1)-(4) are greater than corresponding three of the four percentage movement condition threshold values of any one set of movement condition threshold values of Table 2 for a given corrected total patient weight, CTPW, and sensitivity value, S, the controller 88 determines that a "bounded movement condition" is satisfied and the controller 88 is operable to activate an alarm as will be described more fully hereinafter with respect to the patient movement (PM) mode routine illustrated by example in FIG. 18. Optionally, the corrected total patient weight, CTPW, may be reduced by a specified weight value before calculating any of equations (1)-(4) for the purpose of reducing the thresholds, RHT, RFT, LFT, LHT, that would be expected in the case of light weight patients in the presence of relatively heavy equipment 482 on the bed 50. In any case, Table 2 may thus be referred to hereinafter as a "bounded movement condition threshold" table, data set or collection of data.

It may further be desirable to specify an upper boundary to avoid prematurely satisfying bounded conditions of neighboring sectors. As one specific example of an implementation using an upper boundary, UB, a given set of sector conditions may be satisfied by any three of the following four conditions:

LH has increased by at least 11% of CTPW but by no more than 11%+(UB/4) % since armed, LF has increased by at least 11% of CTPW but by no more than 11%+(UB/4) % since armed, RH has decreased by at least 11% of CTPW but by no more than 11%+(UB/4) % since armed, and RF has decreased by at least 11% of CTPW but by no more than 11%+(UB/4) % since armed.

If a patient changes position at a rate that is higher than the response time of the system 75, it is possible that certain ones of the bounded set of conditions may not detected. To address such possibilities, an unbounded set of conditions is also examined. The number of unbounded conditions will typically be small in any implementation, and any one collection of unbounded movement condition threshold sets may require only two or three load cell conditions to be satisfied. Thresholds are determined experimentally by considering a number, e.g., 12, of different directions in which the patient can move. Table 3 below illustrates a second collection of movement condition threshold value sets, wherein each set of the movement condition threshold values, RHTN, RFTN, LFTN and LHTN, is provided in the form of a normalized percentage value:

For each set of unbounded movement condition threshold values in Table 3, the controller is operable to compute unbounded movement condition threshold values, RHT, RFT, LFT and LHT, from the normalized movement condition threshold values, RHTN, RFTN, LFTN and LHTN, as a function of the corrected total patient weight, CTPW, and the sensitivity value, S, and to compare the computed unbounded movement condition threshold values with weight differentials between the current and reference weight values of corresponding ones of the various load cells. Each set of the unbounded movement condition threshold values are computed according to the equations:

$$LHT = LHTN^*(CTPW/4)^*(1/S) \qquad (9),$$

$$LFT = LFTN^*(CTPW/4)^*(1/S) \qquad (10),$$

$$RFT = RFTN^*(CTPW/4)^*(1/S) \qquad (11),$$

$$RHT = RHTN^*(CTPW/4)^*(1/S) \qquad (12).$$

The weight differentials between the current and reference weight values of the various load cells are computed by the controller 88 according to the equations:

$$LHWD = C^*(LH-RLH) \qquad (13),$$

$$LFWD = C^*(LF-RLF) \qquad (14),$$

$$RFWD = C^*(RF-RFR) \qquad (15),$$

$$RHWD = C^*(RH-RHR) \qquad (16),$$

where RLH, RLF, RFR and RHR are individual load cell reference weight values computed at various times during the PM Exit/Movement Transition State routine of FIGS. 10A-10B and the PM Active State routine of FIGS. 11A-11C, LH, LF, RF and RH are the current weight values measure by the corresponding load cells 68a-68d, "C" is a constant, e.g., 1000, and LHWD, LFWD, RFWD and RHWD are individual load cell weight differentials relative to the corresponding reference weight values. The controller 88 is operable to compare the individual load cell weight differentials computed according to equations (13)-(16) with each corresponding set of the computed unbounded movement condition threshold values computed according to equations (9)-(12) to determine whether an "unbounded movement condition" is satisfied. More specifically, the controller 88 is operable to determine that an unbounded movement condition is satisfied if at least two or three of the four weight differential values are greater than corresponding unbounded movement threshold values of any one set of unbounded movement threshold data if the unbounded movement threshold values are greater than zero, or are less than corresponding unbounded movement threshold values of any one set of unbounded movement threshold data if the unbounded movement threshold values are less than zero. Two exceptions to this rule apply as noted in Table 3, one for the "diagonal to left reverse slide" unbounded condition and one for the "diagonal to right reverse slide" unbounded condition. Otherwise, for sets of unbounded movement threshold values having two non-zero values, an unbounded movement condition is satisfied if the two non-zero weight differentials satisfy the inequality relative to the two unbounded movement threshold values. For sets of unbounded movement threshold values having three non-zero values, an unbounded movement condition is satisfied if the three non-zero weight differentials satisfy the inequality relative to the three unbounded movement threshold values. For example, using the first entry in Table 3, an unbounded condition is satisfied if LHWD>LHT and LFWD<LFT.

Referring now to FIG. 18, a flowchart is shown of one illustrative embodiment of a software algorithm or routine for executing the movement mode routine called by step 440 of the PM Active State routine illustrated in FIGS. 11A-11C. In the illustrated embodiment, the movement mode algorithm or routine begins at step 580 where the controller 88 is operable to determine whether the exit mode is currently selected. If so, execution of the routine advances to step 582 where the controller 88 is operable to set the sensitivity value, S, equal to a first sensitivity value, S1. If, at step 580, the controller 88 determines that the exit mode is not currently active, then the controller 88 is operable to set the sensitivity value, S, to a second sensitivity value, S2, wherein S1 is less than S2. In the illustrated embodiment, the sensitivity value, S, for the bounded movement condition threshold data collection, e.g., Table 2, is set lower, so that the movement mode routine is more sensitive, when the movement mode is selected via the movement mode selection switch 80 than when the exit mode is selected via the exit mode selection switch 84. Thus while both the exit and movement mode routines run in the exit and movement modes, the sensitivity value, S, of the movement mode routine is set to a lower value when the movement mode is selected via the selection switch 80. As examples, S1 may set to 1/29 and S2 may be set to 1/6-1/5, although it will be appreciated that other values of S1 and S2 may be used, and that S1 may alternatively be set less than or equal to S2.

In any case, execution of the movement mode routine advances from step 582, and from the "NO" branch of step 584, to step 586 where the controller 88 is operable to reset the sector to zero. Thereafter at step 588, the controller 88 is operable to determine a movement condition threshold value set for the current sector from the bounded movement threshold table, Table 2. Thereafter at step 590, the controller 88 is operable to determine whether the bounded condition is satisfied by the current load cell data, RH, RF, LF and LH, for at least three of the load cell threshold values, RHT, RFT, LFT and LHT of the movement condition threshold value set for the current sector by plugging RH, RF, LF and LH into the above equations and comparing the results with the movement condition threshold value set for the current sector. If the controller 88 determines at step 690 that for the current sector at least three of the equations (1)-(4) above produce corresponding current percent weight change values, PCRH, PCRF, PCLF and PCLH, that are greater than three corresponding entries in the bounded movement threshold table, Table 2, a bounded condition is satisfied. If the controller 88 determines at step 590 that a bounded condition is satisfied, execution of the routine advances to step 594 where the controller 88 is operable to determine whether the waiting for weight stabilization (WFWS) flag is "false" or the temporary weight value, TEMPW, computed at step 416 of the PM Active State routine of FIGS. 11A-11C is between positive and negative values of the sensitivity to weight change value, SMWC. If both conditions are satisfied, execution of the routine advances to step 596 where the controller 88 is operable to set the remote alarm flag active. Thereafter at step 598, execution of the routine advances to the step 598 where the state machine 120 moves to the PM Alarm State and the controller 88 is operable to execute the PM Alarm State routine of FIG. 12. If, at step 594, neither of the illustrated conditions is satisfied, execution of the routine advances to step 604 where the controller 88 is operable to increment the sector counter by incrementing the angle, "A", by the angle increment value, and then loop back to step 588.

If, at step 590 the controller 88 determines that the bounded condition is not satisfied for at least three of the four load cells, execution of the routine advances to step 592 where the controller 88 is operable to determine whether the unbounded condition is satisfied as described hereinabove. Thereafter at step 600, if the controller 88 determines that the unbounded condition is satisfied for at least two or three of the four load cells, execution of the routine advances to step 596 where the controller 88 is operable to set the remote alarm flag to an active state. If, at step 600 the controller 88 determines that the unbounded condition is not satisfied, execution of the routine advances to step 602 where the controller 88 is operable to determine whether all of the sectors have been checked. If not, execution of the routine advances to step 604 where the controller 88 is operable to increment the sector number by incrementing the angle, "A", by the angle increment value. If, at step 602 the controller 88 determines that all sectors have been checked, execution of the routine advances to return step 616.

Figure 19:
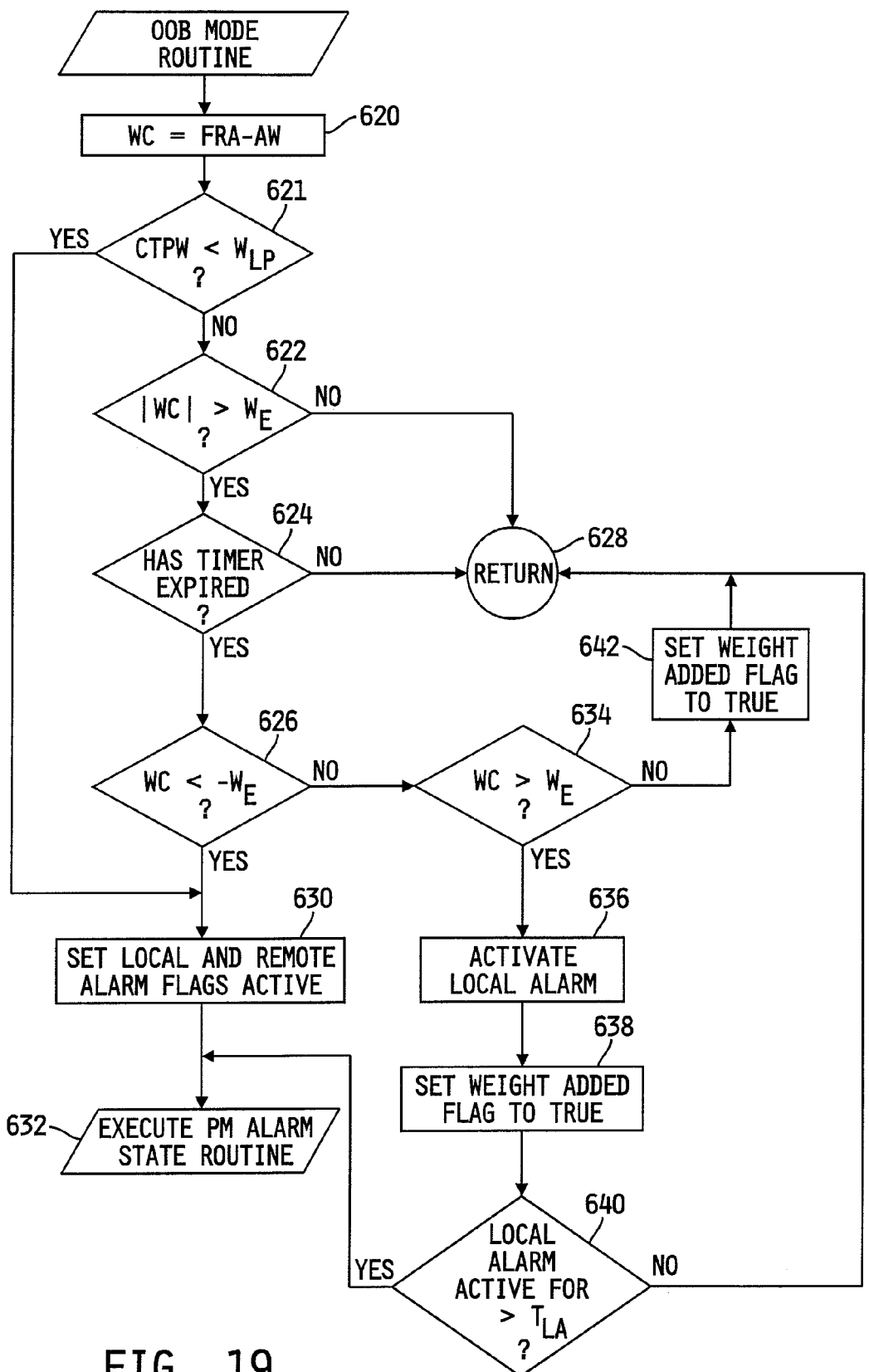
FIG. 19 is a flowchart illustrating an exemplary embodiment of the out-of-bed mode routine called by the PM Active State software routine of FIGS. 11A-11C.

Referring now to FIG. 19, a flowchart is shown of one illustrative embodiment of a software algorithm or routine for executing the out-of-bed (OOB) mode routine called by step 452 of the PM Active State routine illustrated in FIGS. 11A-11C. In the illustrated embodiment, the OOB mode algorithm or routine begins at step 620 where the controller 88 is operable to compute a weight change, WC, as a difference between the total patient weight fast running average, FRA, and the armed weight, AW. Alternatively, the controller 88 may be operable at step 620 to compute WC as a difference between the total patient weight slow running average, SRA, and the armed weight, AW, or the corrected total patient weight, CTPW, and the armed weight. In any case, execution of the routine advances to step 621 where the controller 88 is operable to compare the corrected total patient weight, CTPW, to a low patient weight value, $W_{LP}$. In one embodiment, $W_{LP}$ is 40 lbs., although other values may be used. In any case, if the controller 88 determines at step 621 that CTPW<$W_{LP}$, execution of the routine advances to step 630 where the controller 88 is operable to set the local alarm flag to an active state and to set the remote alarm flag to an active state. Thereafter at step 632 the state machine moves to the PM Alarm State 136, and the controller 88 is operable to execute the PM Alarm State routine of FIG. 12. In an alternative embodiment, the "YES" branch of step 621 may advance to step 624.

If, at step 621, the controller 88 determines that CTPW is not less than $W_{LP}$, execution of the routine advances to step 622 where the controller 88 is operable to compare the absolute weight change value, abs(WC), to an excess weight value, $W_E$. In one embodiment, $W_E$ is set equal to approximately 30 lbs., although other values of $W_E$ may be used. In any case, if the controller 88 determines at step 622 that the absolute value of the weight change, WC, exceeds the excess weight value, $W_E$, this indicates that the total patient weight has changed from the armed weight by an amount sufficient to warrant investigation of the weight change. After expiration of a weight settling timer at step 624, the controller 88 is operable at step 626 to determine whether the detected weight change is due to an addition or subtraction of weight from the weigh frame 56. The timeout value of the weight settling timer may be a constant value, or may instead by a dynamic variable that increases proportionally to CTPW, SRA or FRA. In any case execution of the OOB mode routine advances from the "NO" branches of steps 622 and 624 to the return step 628.

At step 626, the controller 88 is operable to compare the weight change, WC, to the excess weight value, $W_E$, and determine whether WC is less than $-W_E$. If so, this indicates that the patient has transferred at least a significant portion of the patient's weight to a support surface other than the weigh frame 56, and execution of the routine advances to step 630. If, at step 626, the controller 88 determines that the weight change value, WC, is not less than $-W_E$, execution of the routine advances to step 634 where the controller 88 is operable to determine whether WC>$W_E$. If so, execution of the routine advances to step 636 where the controller 88 is operable to activate a visual and/or audible local alarm, and thereafter to step 638 where the controller 88 is operable to set the weight added flag to "true." Following step 638, the controller 88 is operable at step 640 to determine whether the local alarm activated at step 636 has been active for longer than a local alarm time, $T_{LA}$. In one embodiment, $T_{LA}$ is approximately seven seconds, although other values may be used. In any case, if the controller 88 determines at step 640 that the local alarm activated at step 636 has been active for more than $T_{LA}$, execution of the routine advances to step 632. Otherwise, execution of the routine advances to the return step 628. If, at step 634, the controller 88 determines that WC is not greater than $W_E$, execution of the routine advances to step 642 where the controller 88 is operable to set the weight added flag to "true." Execution of the routine advances from step 642 to the return step 638.

Further details relating to one implementation of the OOB mode routine illustrated and described with respect to FIG. 19 are disclosed in U.S. Pat. No. 6,208,250, which is assigned to the assignee of the present invention, and the disclosure of which is incorporated herein by reference.

While the invention has been illustrated and described in detailed in the foregoing drawings and descriptions, the same is to be considered as illustrative and not restrictive in character, it being understood that only illustrative embodiments thereof have been shown and described and that all changes and modifications that come within the spirit of the invention are desired to be protected. For example, while the concepts illustrated and described herein have been disclosed in the context of a hospital bed 50 having a conventional mattress 60, they are also applicable to other types of hospital beds including, but not limited to, air mattress-based beds and the like. As one specific example, one or more of the concepts described herein may be used to control air pressures at different zones of an air mattress as a function of one or more of total patient weight, the distribution of total patient weight on each the plurality of load cells, and the like. As another example, the bed 50 has been illustrated and described as having four load cells 68a-68d, with one each positioned near or toward a different corner of the mattress support frame 58. Alternative embodiments of the bed 50 may include more or fewer load cells. In embodiments including fewer load cells, as few as three may be positioned about the periphery of the mattress support frame 58, and modifications to the various algorithms and routines described herein to accommodate a three load cell system would be a mechanical step for a skilled software programmer. As yet another example, while a number of patient monitoring modes have been described herein, e.g., exit, potential exit and/or movement monitoring modes, those skilled in the art will recognize other patient monitoring modes may be implemented either alone or in combination with other patient monitoring modes. As one specific example, it may be desirable to implement, either alone or in combination with another patient monitoring mode, a highly sensitive patient movement monitoring mode. Such a patient monitoring mode may be implemented using the concepts described hereinabove with respect to FIGS. 15-17 with an appropriate sensitivity value, S.

What is claimed is:

1. A patient support apparatus comprising
a frame,
an air mattress which is supported on a bed frame and which is configured to support an occupant, and
a system for controlling air pressure in a number of different zones of the air mattress, the system comprising a plurality of load cells coupled to the bed frame, each load cell being configured to produce a signal indicative of an amount of weight bearing upon that load cell, and a controller responsive to the signals produced by the plurality of load cells to determine a current distribution of occupant weight on each of the load cells, the controller being configured to control air pressure within any one or more of the number of different zones of the air mattress based on the current distribution of occupant weight on at least some of the plurality of load cells.

2. The patient support apparatus of claim 1, wherein the controller is configured to calculate a total weight of the occupant based on signals received from the plurality of load cells and air pressure within any one or more of the number of different zones of the air mattress is a function of the total weight.

3. The patient support apparatus of claim 1, wherein the controller is configured to monitor a position of a patient based on the signals produced by at least some of the plurality of load cells.

4. The patient support apparatus of claim 3, further comprising an alarm that is activated if a threshold condition is violated, the controller being configured to determine whether the threshold condition is violated based on the signals from at least some of the plurality of load cells and without calculating a center of gravity of the occupant.

5. The patient support apparatus of claim 4, wherein the alarm comprises at least one of a local alarm mounted to the bed frame and a remote alarm.

6. The patient support apparatus of claim 4, wherein the controller is configured to be selectively armed in at least two modes and the threshold condition is different depending upon which of the at least two modes is selected.

7. The patient support apparatus of claim 4, wherein the controller is configured to be selectively armed for activating the alarm when the threshold condition is violated and the controller is configured such that it can be armed only if the patient is within the safe arming zone as determined by the signals from at least some of the plurality of load cells.

8. The patient support apparatus of claim 1, wherein the controller is configured to determine whether the patient is moving toward a sitting up position based on the signals from at least some of the plurality of load cells.

9. The patient support apparatus of claim 1, wherein the controller is configured to determine whether the patient is rolling sideways from a prone position.

10. The patient support apparatus of claim 1, wherein a first plurality of sets of excessive patient movement conditions is stored in a memory of the controller, each of the first plurality of sets of excessive patient movement conditions defines first threshold values for each of the at least three load cells, the controller is configured to determine a total weight of the occupant on the bed, the controller is configured such that, for each of the first plurality of sets of excessive patient movement conditions, weight change values for at least some of the plurality of load cells is computed according to a patient movement model as a function of the total patient weight on the bed, and the controller is configured to determine that patient movement is excessive if at least some of the weight change values exceed corresponding ones of the first threshold values for at least one of the first plurality of sets of excessive patient movement conditions.

11. The patient support apparatus of claim 10, wherein the first threshold values comprise percentage weight values and the weight change values comprise percentage weight change values.

12. A patient support apparatus comprising
a frame,
an air mattress which is supported on the frame and which supports an occupant,
a plurality of load cells coupled to the bed frame, each load cell being configured to produce a signal indicative of an amount of weight bearing upon that load cell, and
a controller being responsive to the signals produced by the plurality of load cells to determine a current distribution of occupant weight on each of the load cells, the controller being configured to control air pressure within any one or more of the number of different zones of the air mattress based on the current distribution of occupant weight on at least some of the plurality of load cells, the controller also being configured to determine whether a patient position threshold condition is violated based on the signals from at least some of the plurality of load cells and without calculating a center of gravity of the occupant, the controller being configured to activate an alarm if the patient position threshold condition is violated.

13. The patient support apparatus of claim 12, wherein the alarm comprises at least one of a local alarm mounted to the bed frame and a remote alarm.

14. The patient support apparatus of claim 12, wherein the controller is configured to be selectively armed in at least two modes and the threshold condition is different depending upon which of the at least two modes is selected.

15. The patient support apparatus of claim 12, wherein the controller is configured to be selectively armed for activating the alarm when the threshold condition is violated and the controller is configured such that it can be armed only if the patient is within the safe arming zone as determined by the signals from at least some of the plurality of load cells.

16. The patient support apparatus of claim 12, wherein the controller is configured to determine whether the patient is moving toward a sitting up position based on the signals from at least some of the plurality of load cells.

17. The patient support apparatus of claim 12, wherein the controller is configured to determine whether the patient is rolling sideways from a prone position.

* * * * *